(12) United States Patent
Ito et al.

(10) Patent No.: US 12,084,436 B2
(45) Date of Patent: Sep. 10, 2024

(54) HETEROCYCLIC COMPOUND

(71) Applicant: Takeda Pharmaceutical Company Limited, Osaka (JP)

(72) Inventors: Masahiro Ito, Kanagawa (JP); Takeshi Yamamoto, Kanagawa (JP); Keiko Kakegawa, Kanagawa (JP); Hideyuki Sugiyama, Kanagawa (JP); Tohru Miyazaki, Kanagawa (JP); Yasuyoshi Arikawa, Kanagawa (JP); Tomohiro Okawa, Kanagawa (JP); Jinichi Yonemori, Kanagawa (JP); Osamu Kubo, Kanagawa (JP); Akinori Toita, Kanagawa (JP); Takuto Kojima, Kanagawa (JP); Fumiaki Kikuchi, Kanagawa (JP); Minoru Sasaki, Kanagawa (JP); Misaki Homma, Kanagawa (JP); Yasuhiro Imaeda, Kanagawa (JP); Hironobu Maezaki, Kanagawa (JP); Shiinobu Sasaki, Kanagawa (JP); Ayumu Sato, Kanagawa (JP); Hirotaka Kamitani, Kanagawa (JP); Yasutomi Asano, Kanagawa (JP); Hironori Kokubo, Kanagawa (JP); Masato Yoshikawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 621 days.

(21) Appl. No.: 17/426,971

(22) PCT Filed: Jan. 29, 2020

(86) PCT No.: PCT/JP2020/003063
§ 371 (c)(1),
(2) Date: Jul. 29, 2021

(87) PCT Pub. No.: WO2020/158762
PCT Pub. Date: Aug. 6, 2020

(65) Prior Publication Data
US 2022/0098180 A1 Mar. 31, 2022

(30) Foreign Application Priority Data
Jan. 30, 2019 (JP) .................. 2019-014893

(51) Int. Cl.
C07D 413/10 (2006.01)
C07D 271/06 (2006.01)
C07D 413/14 (2006.01)
C07D 417/14 (2006.01)

(52) U.S. Cl.
CPC ......... C07D 413/10 (2013.01); C07D 271/06 (2013.01); C07D 413/14 (2013.01); C07D 417/14 (2013.01)

(58) Field of Classification Search
CPC .. C07D 413/10; C07D 271/06; C07D 413/14; C07D 417/14
See application file for complete search history.

(56) References Cited

U.S. PATENT DOCUMENTS

| | | |
|---|---|---|
| 2017/0015655 A1 | 1/2017 | Kaieda et al. |
| 2018/0215743 A1 | 8/2018 | Lee et al. |
| 2018/0222896 A1 | 8/2018 | Kaieda et al. |
| 2018/0230113 A1 | 8/2018 | Lee et al. |
| 2018/0230114 A1 | 8/2018 | Lee et al. |
| 2018/0251437 A1 | 9/2018 | Lee et al. |
| 2018/0256572 A1 | 9/2018 | Yates |
| 2018/0263967 A1 | 9/2018 | Kaieda et al. |
| 2018/0273495 A1 | 9/2018 | Kim et al. |
| 2019/0008836 A1 | 1/2019 | Kaieda et al. |
| 2019/0135799 A1 | 5/2019 | Ito et al. |
| 2020/0171028 A1 | 6/2020 | Yates |

FOREIGN PATENT DOCUMENTS

| | | |
|---|---|---|
| WO | WO-2016/031815 A1 | 3/2016 |
| WO | WO2016176449 A1 * | 3/2016 |
| WO | WO-2017/014170 A1 | 1/2017 |
| WO | WO-2017/014321 A1 | 1/2017 |
| WO | WO-2017/018803 A1 | 2/2017 |
| WO | WO-2017/018804 A1 | 2/2017 |
| WO | WO-2017/018805 A1 | 2/2017 |
| WO | WO-2017/023133 A2 | 2/2017 |
| WO | WO-2017/033946 A1 | 3/2017 |
| WO | WO-2017/065473 A1 | 4/2017 |
| WO | WO-2018/165520 A1 | 9/2018 |
| WO | WO-2019/027054 A1 | 2/2019 |

OTHER PUBLICATIONS

Dubey et al., "Neurodegeneration and microtubule dynamics: death by a thousand cuts," Frontiers in Cellular Neuroscience, Sep. 9, 2015, 9(343):1-15.

(Continued)

*Primary Examiner* — Samantha L Shterengarts
*Assistant Examiner* — Karen Cheng
(74) *Attorney, Agent, or Firm* — Foley & Lardner LLP

(57) ABSTRACT

The present invention provides a heterocyclic compound having a HDAC inhibitory action, which is useful for the treatment of central nervous system diseases including neurodegenerative diseases, and the like, and a medicament comprising the compound.
The present invention relates to a compound represented by the formula (I):

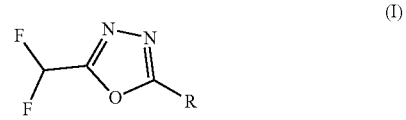

wherein each symbol is as described in the description, or a salt thereof.

16 Claims, No Drawings

(56) References Cited

OTHER PUBLICATIONS

Goedert et al., "Frontotemporal Dementia: Implications for Understanding Alzheimer Disease," Cold Spring Harbor Perspectives in Medicine, 2012 (online Nov. 22, 2011), 4:a006254, 1-21.
Hubbert et al., "HDAC6 is a microtube-associated deacetylase," Nature, May 23, 2002, 417:455-458.
Leroux, Michel R., "Tubulin acetyltransferase discovered: Ciliary role in the ancestral eukaryote expanded to neurons in metazoans," PNAS, Dec. 14, 2020, 107(50):21238-21239.
Morfini et al., "Fast Axonal Transport Misregulation and Alzheimer's Disease," NeuroMolecular Medicine, 2002, 2:89-99.
Selenica et al., "Histone deacetylase 6 inhibition improves memory and reduces total tau levels in a mouse model of tau deposition," Alzheimer's Research & Therapy, 2014, 6:12.

\* cited by examiner

HETEROCYCLIC COMPOUND

CROSS-REFERENCE TO RELATED APPLICATIONS

This application is the U.S. National Stage of PCT/JP2020/003063, filed Jan. 29, 2020, which claims priority to JP 2019-014893, filed Jan. 30, 2019.

TECHNICAL FIELD

The present invention relates to a heterocyclic compound having a histone deacetylase (hereinafter sometimes to be referred to as "HDAC") inhibitory activity, preferably a class II HDAC inhibitory activity, more preferably a HDAC6 inhibitory activity, which may be useful for the treatment of central nervous system diseases including neurodegenerative diseases (Alzheimer's disease, progressive supranuclear palsy, etc.) and the like, and a medicament comprising the compound and the like.

BACKGROUND OF THE INVENTION

Nerve axon is known to play an important role in transport of nutritional factor, neurotransmitter, organelle and the like in nerve cell, and axon function disorder, axonal degeneration and intracellular accumulation of axon binding protein tau are observed in various neurodegenerative diseases (Non-Patent Document 1 and Non-Patent Document 2). Diseases characterized by intracellular tau accumulation are collectively called pathologically as tauopathy, and they encompass Alzheimer's disease, progressive supranuclear palsy and the like (Non-Patent Document 3). HDAC6 is an enzyme which plays a role in deacetylation of axon component, tubulin (Non-Patent Document 4), and microtubule containing acetylated tubulin is known to contribute to stability (Non-Patent Document 5). In addition, it is reported that Tubastatin A having a HDAC6 inhibitory activity increases acetylation of tubulin in tauopathy mouse model, and shows therapeutic effectiveness (Non-Patent Document 6). Therefore, the above-mentioned reports suggest that HDAC6 inhibitor has the potential to be a therapeutic drug for Alzheimer's disease and progressive supranuclear palsy via stabilization of axon.

As heterocyclic compounds, for example, the following compound are known.

(1) Patent Document 1 discloses a compound represented by the following formula:

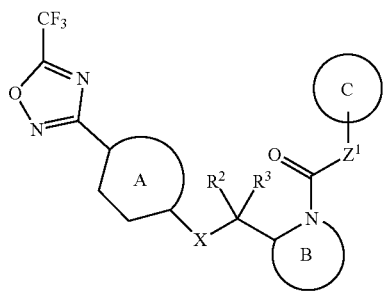

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(2) Patent Document 2 discloses a compound represented by the following formula:

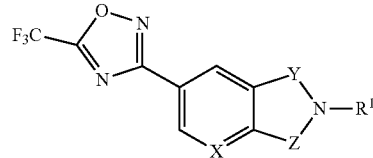

wherein each symbol is as defined in the document, which is a HDAC inhibitor, and is effective for the treatment of autoimmune diseases, inflammatory diseases, metabolic/ostecarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(3) Patent Document 3 discloses a compound represented by the following formula:

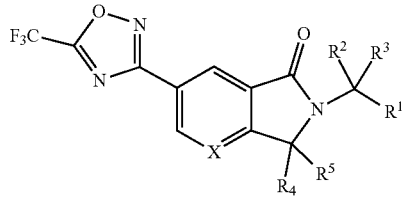

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(4) Patent Document 4 discloses a compound represented by the following formula:

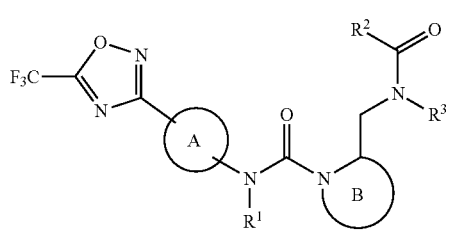

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(5) Patent Document 5 discloses a compound represented by the following formula:

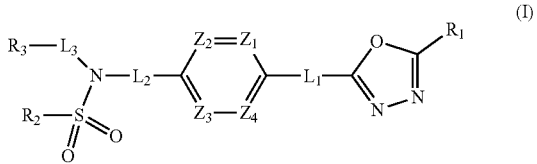

(I)

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(6) Patent Document 6 discloses a compound represented by the following formula:

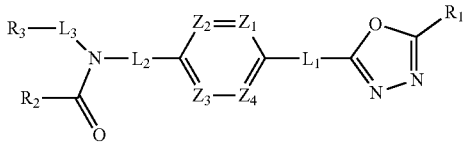

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(7) Patent Document 7 discloses a compound represented by the following formula:

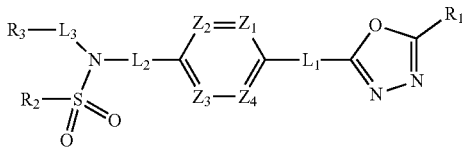

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(8) Patent Document 8 discloses a compound represented by the following formula:

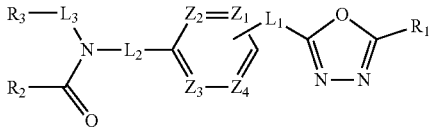

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(9) Patent Document 9 discloses a compound represented by the following formula:

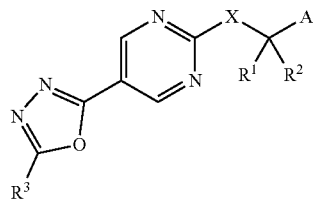

wherein each symbol is as defined in the document, which is a HDAC inhibitor, and is effective for the treatment of epilepsy, attentional deficit disorder, depression, anxiety, Alzheimer's disease, Parkinson's disease, Huntington's disease and the like.

(10) Patent Document 10 discloses a compound represented by the following formula:

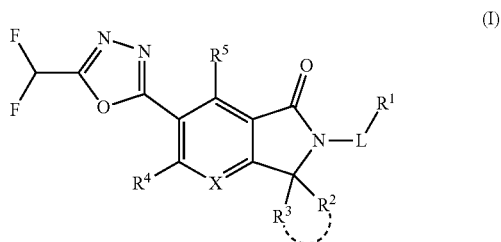

(I)

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

DOCUMENT LIST

Patent Document

Patent Document 1: WO 2016/031815
Patent Document 2: WO 2017/014321

Patent Document 3: WO 2017/014170
Patent Document 4: WO 2017/033946
Patent Document 5: WO 2017/018803
Patent Document 6: WO 2017/018804
Patent Document 7: WO 2017/018805
Patent Document 8: WO 2017/023133
Patent Document 9: WO 2018/165520
Patent Document 10: WO 2019/027054

Non-Patent Document

Non-Patent Document 1] Front Cell Neurosci. 9, 343, (2015).
Non-Patent Document 2] Neuromolecular Med. 2: 89-99, (2002).
Non-Patent Document 3] Cold Spring Harb Perspect Med. 2: a006254 (2012).
Non-Patent Document 4] Nature. 417: 455-458, (2002).
Non-Patent Document 5] Proc Natl Acad Sci USA. 107: 21238-21239, (2010).
Non-Patent Document 6] Alzheimers Res Ther. 6: 12, (2014).

SUMMARY OF THE INVENTION

Problems to be Solved by the Invention

The present invention aims to provide a heterocyclic compound having a HDAC inhibitory action, and useful for the treatment of central nervous system diseases including neurodegenerative diseases (Alzheimer's disease, progressive supranuclear palsy, etc.) and the like, and a medicament comprising the compound.

Means of Solving the Problems

The present inventors have conducted intensive studies to solve the above-mentioned problems, and have found that a compound represented by the following formula (I) has a superior HDAC inhibitory action, and completed the present invention based on these findings.

Accordingly, the present invention provides the following.

[1] A compound represented by the formula (I):

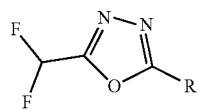

(I)

wherein R is
(a) a group represented by the formula:

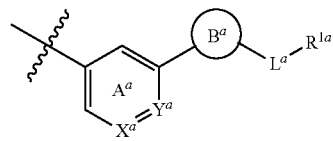

wherein
$X^a$ is $CR^{2a}$ wherein $R^{2a}$ is a hydrogen atom or a halogen atom, or N, $Y^a$ is $CR^{3a}$ wherein $R^{3a}$ is a hydrogen atom or a halogen atom, or N, Ring $A^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms, Ring $B^a$ is an optionally further substituted ring, $L^a$ is a bond, or a spacer having 1 to 3 atoms in the main chain, and $R^{1a}$ is an optionally substituted $C_{1-6}$ alkyl group or an optionally substituted cyclic group, (b) a group represented by the formula:

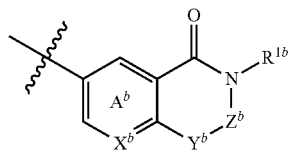

wherein
$X^b$ is $CR^{2b}$ wherein $R^{2b}$ is a hydrogen atom or a halogen atom, or N, Ring $A^b$ is (i) a benzene ring optionally further substituted by 1 or 2 halogen atoms, or (ii) a pyridine ring optionally further substituted by 1 or 2 halogen atoms, $Y^b$ is an oxygen atom or an optionally substituted methylene, $Z^b$ is $CR^{3b}R^{4b}$ wherein $R^{3b}$ and $R^{4b}$ are each independently a hydrogen atom, an optionally substituted $C_{1-6}$ alkyl group or an optionally substituted cyclic group, or $NR^{5b}$ wherein $R^{5b}$ is an optionally substituted $C_{1-6}$ alkyl group or an optionally substituted cyclic group, and $R^{1b}$ is a hydrogen atom, an optionally substituted $C_{1-6}$ alkyl group or an optionally substituted cyclic group, or (c) a group represented by the formula:

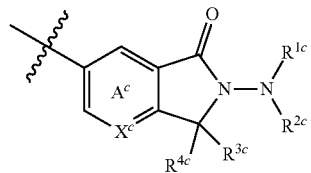

wherein
$X^c$ is $CR^{5c}$ wherein $R^{5c}$ is a hydrogen atom or a halogen atom, or N, Ring $A^c$ is (i) a benzene ring optionally further substituted by 1 or 2 halogen atoms, or (ii) a pyridine ring optionally further substituted by 1 or 2 halogen atoms, $R^{1c}$ and $R^{2c}$ are each independently a hydrogen atom or a substituent, and $R^{3c}$ and $R^{4c}$ are each independently a hydrogen atom, an optionally substituted $C_{1-6}$ alkyl group or an optionally substituted $C_{1-6}$ alkoxy group, or a salt thereof (hereinafter sometimes to be referred to as compound (I)).

[2] The compound or salt according to the above-mentioned [1], which is represented by the formula (I-a):

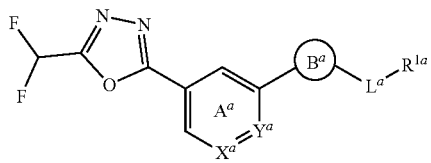

(I-a)

wherein
X$^a$ is CR$^{2a}$ wherein R$^{2a}$ is a hydrogen atom or a halogen atom, or N,
Y$^a$ is CR$^{3a}$ wherein R$^{3a}$ is a hydrogen atom or a halogen atom, or N,
Ring A$^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms,
Ring B$^a$ is an optionally further substituted ring,
L$^a$ is a bond, or a spacer having 1 to 3 atoms in the main chain, and
R$^{1a}$ is an optionally substituted C$_{1-6}$ alkyl group or an optionally substituted cyclic group.

[3] The compound or salt according to the above-mentioned [2], wherein
X$^a$ is CH, CF or N;
Y$^a$ is CH or N;
Ring A$^a$ is a benzene ring optionally substituted by one fluorine atom, or a pyridine ring, which is represented by formula:

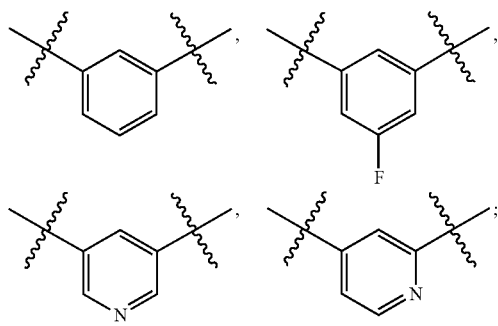

Ring B$^a$ is
(1) a 5- or 6-membered monocyclic aromatic heterocycle optionally substituted by 1 to 3 substituents selected from a halogen atom and a cyano group,
(2) a 5- or 6-membered non-aromatic heterocycle optionally substituted by 1 to 3 substituents selected from a C$_{1-6}$ alkyl group and an oxo group, or
(3) a 9- to 14-membered fused bicyclic non-aromatic heterocycle;
L$^a$ is
(1) a bond,
(2) —CH$_2$—,
(3) —CH(CH$_3$)—,
(4) —O—,
(5) —OCH$_2$—,
(6) —CH$_2$C(O)—,
(7) —OCH$_2$CH$_2$—,
(8) —CH$_2$C(O)NH— or
(9) —CH$_2$CH$_2$O—; and R$^{1a}$ is
(1) a C$_{1-6}$ alkyl group optionally substituted by 1 to 3 C$_{1-6}$ alkoxy groups,
(2) a C$_{3-6}$ cycloalkyl group optionally substituted by 1 to 3 halogen atoms,
(3) a C$_{6-10}$ aryl group optionally substituted by 1 to 3 substituents selected from
 (i) a halogen atom,
 (ii) a cyano group,
 (iii) an optionally halogenated C$_{1-6}$ alkyl group,
 (iv) a C$_{1-6}$ alkoxy group, and
 (v) an N-mono-C$_{1-6}$ alkyl-carbamoyl group,
(4) a 5- or 6-membered aromatic heterocyclic group optionally substituted by 1 to 3 substituents selected from
 (i) a halogen atom,
 (ii) a cyano group,
 (iii) a C$_{1-6}$ alkyl group, and
 (iv) a C$_{1-6}$ alkoxy group, or
(5) a 4- to 6-membered non-aromatic heterocyclic group optionally substituted by 1 to 3 substituents selected from
 (i) a C$_{1-6}$ alkyl group,
 (ii) a C$_{1-6}$ alkyl-carbonyl group,
 (iii) a C$_{1-6}$ alkoxy-carbonyl group, and
 (iv) an oxo group.

[4] 5-[(2-{4-[5-(Difluoromethyl)-1,3,4-oxadiazol-2-yl]pyridin-2-yl}-1H-imidazol-1-yl)methyl]-2-fluorobenzonitrile or a salt thereof,
2-{4-[5-(difluoromethyl)-1,3,4-oxadiazol-2-yl]pyridin-2-yl}-1-[(3-fluorophenyl)methyl]-1H-imidazole-5-carbonitrile or a salt thereof, or
4-[5-(difluoromethyl)-1,3,4-oxadiazol-2-yl]-2-{1-[(3-fluorophenyl)methyl]-1H-1,2,4-triazol-5-yl}pyridine or a salt thereof.

[5] The compound or salt according to the above-mentioned [1], which is represented by the formula (I-b):

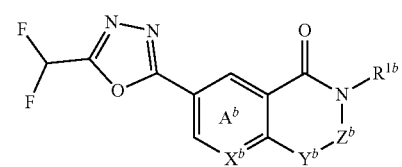

(I-b)

wherein
X$^b$ is CR$^{2b}$ wherein R$^{2b}$ is a hydrogen atom or a halogen atom, or N,
Ring A$^b$ is (i) a benzene ring optionally further substituted by 1 or 2 halogen atoms, or (ii) a pyridine ring optionally further substituted by 1 or 2 halogen atoms,
Y$^b$ is an oxygen atom or an optionally substituted methylene,
Z$^b$ is CR$^{3b}$R$^{4b}$ wherein R$^{3b}$ and R$^{4b}$ are each independently a hydrogen atom, an optionally substituted C$_{1-6}$ alkyl group or an optionally substituted cyclic group, or NR$^{5b}$ wherein R$^{5b}$ is an optionally substituted C$_{1-6}$ alkyl group or an optionally substituted cyclic group, and
R$^{1b}$ is a hydrogen atom, an optionally substituted C$_{1-6}$ alkyl group or an optionally substituted cyclic group.

[6] The compound or salt according to the above-mentioned [5], wherein
X$^b$ is CH or N;
Ring A$^b$ is (i) a benzene ring, or (ii) a pyridine ring;
Y$^b$ is an oxygen atom or methylene;

$Z^b$ is (1) a group represented by $CR^{3b'}R^{4b'}$ wherein
$R^{3b'}$ is
   (a) a hydrogen atom, or
   (b) a $C_{1-6}$ alkyl group optionally substituted by 1 to 3 $C_{1-6}$ alkoxy groups; and
$R^{4b'}$ is
   (a) a hydrogen atom,
   (b) a $C_{3-6}$ cycloalkyl group,
   (c) a $C_{6-10}$ aryl group optionally substituted by 1 to 3 substituents selected from
      (i) a halogen atom,
      (ii) a cyano group,
      (iii) an optionally halogenated $C_{1-6}$ alkyl group, and
      (iv) an optionally halogenated $C_{1-6}$ alkoxy group, or
   (d) a 5- or 6-membered aromatic heterocyclic group, or (2) a group represented by $NR^{5b'}$ wherein
$R^{5b'}$ is
   (a) an optionally halogenated $C_{1-6}$ alkyl group,
   (b) a $C_{3-6}$ cycloalkyl group optionally substituted by 1 to 3 halogen atoms,
   (c) a $C_{6-10}$ aryl group optionally substituted by 1 to 3 halogen atoms, or
   (d) a 5- or 6-membered non-aromatic heterocyclic group; and $R^{1b}$ is (1) a hydrogen atom, or
(2) a $C_{1-6}$ alkyl group optionally substituted by 1 to 3 substituents selected from
   (i) a halogen atom,
   (ii) a $C_{3-6}$ cycloalkyl group,
   (iii) a $C_{6-10}$ aryl group, and
   (iv) a $C_{1-6}$ alkoxy group (e.g., methoxy).

[7] 3-[5-(Difluoromethyl)-1,3,4-oxadiazol-2-yl]-7-(4-fluorophenyl)-6,7-dimethyl-7,8-dihydro-1,6-naphthyridin-5 (6H)-one or a salt thereof, 7-[5-(difluoromethyl)-1,3,4-oxadiazol-2-yl]-3-(4-fluorophenyl)-3,4-dihydrophthalazin-1(2H)-one or a salt thereof, or 7-[5-(difluoromethyl)-1,3,4-oxadiazol-2-yl]-2-ethyl-3-(4-fluorophenyl)-3,4-dihydrophthalazin-1(2H)-one or a salt thereof.

[8] The compound or salt according to the above-mentioned [1], which is represented by the formula (I-c):

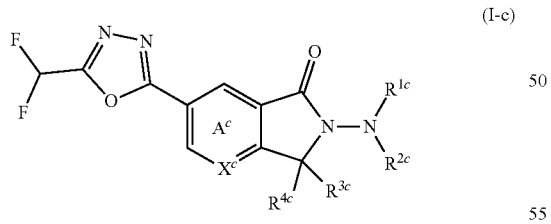

(I-c)

wherein
$X^c$ is $CR^{5c}$ wherein $R^{5c}$ is a hydrogen atom or a halogen atom, or N,
Ring $A^c$ is (i) a benzene ring optionally further substituted by 1 or 2 halogen atoms, or (ii) a pyridine ring optionally further substituted by 1 or 2 halogen atoms,
$R^{1c}$ and $R^{2c}$ are each independently a hydrogen atom or a substituent, and
$R^{3c}$ and $R^{4c}$ are each independently a hydrogen atom, an optionally substituted $C_{1-6}$ alkyl group or an optionally substituted $C_{1-6}$ alkoxy group.

[9] The compound or salt according to the above-mentioned [8], wherein
$X^c$ is CH, or N;
Ring $A^c$ is (i) a benzene ring, or (ii) a pyridine ring;
$R^{1c}$ is
(1) a hydrogen atom,
(2) a $C_{1-6}$ alkyl group optionally substituted by 1 to 3 substituents selected from
   (i) a $C_{6-10}$ aryl group optionally substituted by 1 to 3 halogen atoms,
   (ii) a 5- or 6-membered aromatic heterocyclic group optionally substituted by 1 to 3 $C_{3-6}$ cycloalkyl groups, and
   (iii) a 5- or 6-membered non-aromatic heterocyclic group,
(3) a $C_{1-6}$ alkyl-carbonyl group optionally substituted by 1 to 3 halogen atoms,
(4) a $C_{1-6}$ alkoxy-carbonyl group optionally substituted by 1 to 3 substituents selected from
   (i) a halogen atom,
   (ii) a $C_{1-6}$ alkoxy group, and
   (iii) a 5- or 6-membered aromatic heterocyclic group,
(5) a $C_{3-6}$ cycloalkoxy-carbonyl group optionally substituted by 1 to 3 $C_{1-6}$ alkoxy groups,
(6) a 5- or 6-membered non-aromatic heterocyclyloxy-carbonyl group, or
(7) a $C_{1-6}$ alkylsulfonyl group;
$R^{2c}$ is
(1) a $C_{1-6}$ alkyl group optionally substituted by 1 to 3 substituents selected from
   (i) a halogen atom,
   (ii) a $C_{3-6}$ cycloalkyl group optionally substituted by 1 to 3 halogen atoms,
   (iii) a $C_{6-10}$ aryl group optionally substituted by 1 to 3 substituents selected from
      (a) a halogen atom,
      (b) a hydroxy group,
      (c) an optionally halogenated $C_{1-6}$ alkyl group,
      (d) a $C_{1-6}$ alkoxy group optionally substituted by 1 to 3 $C_{1-6}$ alkoxy groups,
      (e) a $C_{1-6}$ alkoxy-carbonyl group,
      (f) a di-$C_{1-6}$ alkylamino group,
      (g) a $C_{1-6}$ alkyl-carbonylamino group,
      (h) a 5- or 6-membered aromatic heterocyclic group,
      (i) a 5- or 6-membered non-aromatic heterocyclic group, and
      (j) a 5- or 6-membered aromatic heterocyclyloxy group,
   (iv) a $C_{7-16}$ aralkyloxy group,
   (v) a $C_{1-6}$ alkoxy-carbonyl group,
   (vi) a 5- or 6-membered aromatic heterocyclic group optionally substituted by 1 to 3 substituents selected from
      (a) a halogen atom, and
      (b) a $C_{3-6}$ cycloalkyl group,
   (vii) a 5- or 6-membered non-aromatic heterocyclic group, and
   (viii) a 8- to 14-membered fused polycyclic aromatic heterocyclic group,
(2) a $C_{3-6}$ cycloalkyl group optionally substituted by 1 to 3 halogen atoms,
(3) a $C_{6-10}$ aryl group optionally substituted by 1 to 5 halogen atoms,
(4) a 5- or 6-membered aromatic heterocyclic group optionally substituted by 1 to 3 halogen atoms,
(5) a 5- or 6-membered non-aromatic heterocyclic group, or (6) a $C_{1-6}$ alkoxy-carbonyl group; and $R^{3c}$ and $R^{4c}$ are both hydrogen atoms.

[10] 6-[5-(Difluoromethyl)-1,3,4-oxadiazol-2-yl]-2-{[(4-fluorophenyl)methyl][(oxan-4-yl)methyl]amino}-2,3-dihydro-1H-isoindol-1-one or a salt thereof, 2-{[(5-chloropyridin-3-yl)methyl] (methyl)amino}-6-[5-(difluoromethyl)-1,3,4-oxadiazol-2-yl]-2,3-dihydro-1H-isoindol-1-one or a salt thereof, or 2-{[(3,3-difluorocyclobutyl)methyl] (methyl)amino}-6-[5-(difluoromethyl)-1,3,4-oxadiazol-2-yl]-2,3-dihydro-1H-isoindol-1-one or a salt thereof.

[11] A medicament comprising the compound or salt according to the above-mentioned [1].

[12] The medicament according to the above-mentioned [11], which is a histone deacetylase 6 inhibitor.

[13] The medicament according to the above-mentioned [11], which is an agent for the prophylaxis or treatment of Alzheimer's disease or progressive supranuclear palsy.

[14] The compound or salt according to the above-mentioned [1] for use in the prophylaxis or treatment of Alzheimer's disease or progressive supranuclear palsy.

[15] A method for inhibiting histone deacetylase 6 in a mammal, which comprises administering an effective amount of the compound or salt according to the above-mentioned [1] to the mammal.

[16] A method for preventing or treating Alzheimer's disease or progressive supranuclear palsy in a mammal, which comprises administering an effective amount of the compound or salt according to the above-mentioned [1] to the mammal.

[17] Use of the compound or salt according to the above-mentioned [1] for the manufacture of an agent for the prophylaxis or treatment of Alzheimer's disease or progressive supranuclear palsy.

Effect of the Invention

Compound (I) has a HDAC inhibitory activity, and may be useful for the treatment of central nervous system diseases including neurodegenerative diseases (Alzheimer's disease, progressive supranuclear palsy, etc.) and the like.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, ischexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthic, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxycarbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),

(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a Cy-1 aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, so tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH═CH—, —CH$_2$—CH═CH—, —CH═CH—CH$_2$—, —C(CH$_3$)$_2$—CH═CH—, —CH═CH—C(CH$_3$)$_2$—, —CH$_2$—CH═CH—CH$_2$—, —CH$_2$—CH$_2$—CH═CH—, —CH═CH—CH$_2$—CH$_2$—, —CH═CH—CH═CH—, —CH═CH—CH$_2$—CH$_2$—CH$_2$— and —CH$_2$—CH$_2$—CH$_2$—CH═CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C—CH$_2$—CH$_2$—CH$_2$— and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazcle, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, so thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydroindazole, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

The definition of each symbol used in the formula (I) is explained.

In the formula (I), R is (a) a group represented by the formula:

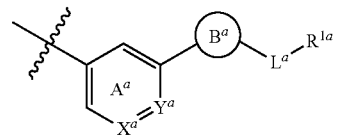

wherein $X^a$ is $CR^{2a}$ wherein $R^{2a}$ is a hydrogen atom or a halogen atom, or N, $Y^a$ is $CR^{3a}$ wherein $R^{3a}$ is a hydrogen atom or a halogen atom, or N, Ring $A^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms, Ring $B^a$ is an optionally further substituted ring, $L^a$ is a bond, or a spacer having 1 to 3 atoms in the main chain, and $R^{1a}$ is an optionally substituted $C_{1-6}$ alkyl group or an optionally substituted cyclic group, (b) a group represented by the formula:

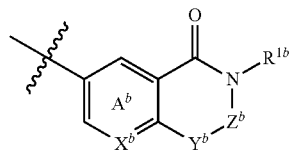

wherein $X^b$ is $CR^{2b}$ wherein $R^{2b}$ is a hydrogen atom or a halogen atom, or N, Ring $A^b$ is (i) a benzene ring optionally further substituted by 1 or 2 halogen atoms, or (ii) a pyridine ring optionally further substituted by 1 or 2 halogen atoms, $Y^b$ is an oxygen atom or an optionally substituted methylene, $Z^b$ is $CR^{3b}R^{4b}$ wherein $R^{3b}$ and $R^{4b}$ are each independently a hydrogen atom, an optionally substituted $C_{1-6}$ alkyl group or an optionally substituted cyclic group, or $NR^{5b}$ wherein $R^{5b}$ is an optionally substituted $C_{1-6}$ alkyl group or an optionally substituted cyclic group, and $R^{1b}$ is a hydrogen atom, an optionally substituted $C_{1-6}$ alkyl group or an optionally substituted cyclic group, or (c) a group represented by the formula:

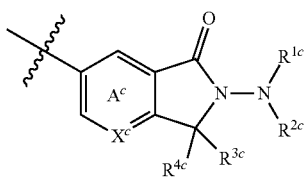

wherein
- $X^c$ is $CR^{5c}$ wherein $R^{5c}$ is a hydrogen atom or a halogen atom, or N,
- Ring $A^c$ is (i) a benzene ring optionally further substituted by 1 or 2 halogen atoms, or (ii) a pyridine ring optionally further substituted by 1 or 2 halogen atoms,
- $R^{1c}$ and $R^{2c}$ are each independently a hydrogen atom or a substituent, and
- $R^{3c}$ and $R^{4c}$ are each independently a hydrogen atom, an optionally substituted $C_{1-6}$ alkyl group or an optionally substituted $C_{1-6}$ alkoxy group.

That is, compound (I) is composed of the following compound (I-a), compound (I-b) and compound (I-c). Compound (I-a), compound (I-b) and compound (I-c) are collectively referred to as compound (I).

Compound (I-a)

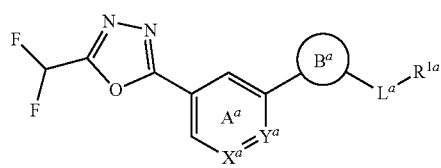

wherein each symbol is as defined above.

Compound (I-b)

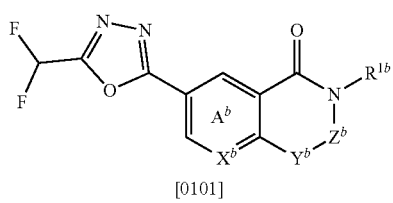

[0101]

wherein each symbol is as defined above.

Compound (I-c)

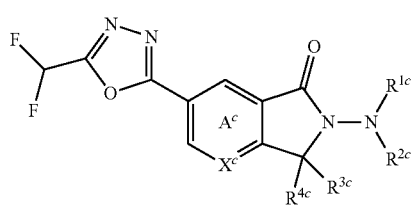

wherein each symbol is as defined above.

Hereinafter, compound (I-a), compound (I-b) and compound (I-c) are explained in detail.

Compound (I-a)

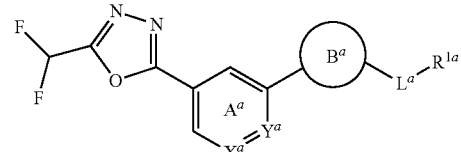

wherein each symbol is as defined above.

$X^a$ is $CR^{2a}$ wherein $R^{2a}$ is a hydrogen atom or a halogen atom, or N.

$X^a$ is preferably CH, CF or N.

$X^a$ is particularly preferably CH.

$Y^a$ is $CR^{3a}$ wherein $R^{3a}$ is a hydrogen atom or a halogen atom, or N.

$Y^a$ is preferably CH or N.

$Y^a$ is particularly preferably N.

Ring $A^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms.

Ring $A^a$ is preferably (i) a benzene ring optionally further substituted by 1 or 2 halogen atoms, or (ii) a pyridine ring optionally further substituted by 1 or 2 halogen atoms, more preferably (i) a benzene ring optionally further substituted by 1 or 2 halogen atoms (preferably a fluorine atom), or (ii) a pyridine ring. Specifically, Ring $A^a$ is preferably a benzene ring optionally substituted by one fluorine atom, or a pyridine ring, which is represented by the formula:

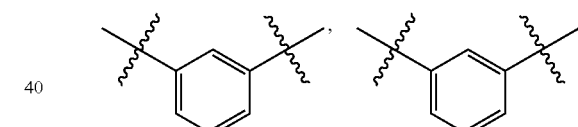

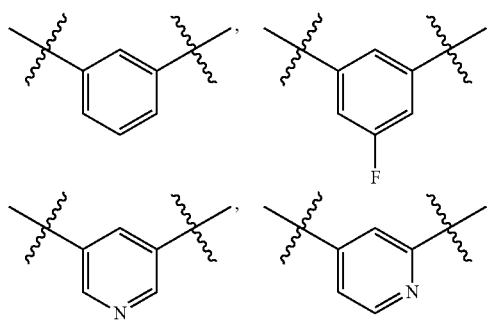

Ring $A^a$ is particularly preferably a pyridine ring represented by the formula:

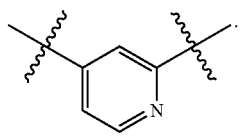 [SMILES: *c1ccnc(*)c1]

Ring $B^a$ is an optionally further substituted ring. Examples of the "substituent" of the "optionally further substituted ring" for Ring $B^a$ include those exemplified as Substituent Group A and an oxo group. Ring $B^a$ optionally has 1 to 3 substituents at substitutable position(s). Preferable examples of the substituent include a halogen atom (e.g., a chlorine atom, a bromine atom), a cyano group, a $C_{1-6}$ alkyl group (e.g., methyl) and an oxo group.

Examples of the ring of the "optionally further substituted ring" for Ring $B^a$ include a hydrocarbon ring, an aromatic heterocycle and a non-aromatic heterocycle.

Preferable examples thereof include
(1) a 5- or 6-membered monocyclic aromatic heterocycle (e.g., imidazole, pyrazole, triazole, pyridine, pyrimidine),
(2) a 5- or 6-membered non-aromatic heterocycle (e.g., oxazolidine, morpholine, dihydropyridine), and
(3) a 9- to 14-membered fused bicyclic non-aromatic heterocycle (e.g., tetrahydroindazole).

Ring $B^a$ is preferably
(1) a 5- or 6-membered monocyclic aromatic heterocycle (e.g., imidazole, pyrazole, triazole, pyridine, pyrimidine) optionally substituted by 1 to 3 substituents selected from a halogen atom (e.g., a chlorine atom, a bromine atom) and a cyano group,
(2) a 5- or 6-membered non-aromatic heterocycle (e.g., oxazolidine, morpholine, dihydropyridine) optionally substituted by 1 to 3 substituents selected from a $C_{1-6}$ alkyl group (e.g., methyl) and an oxo group, or
(3) a 9- to 14-membered fused bicyclic non-aromatic heterocycle (e.g., tetrahydroindazole).

Ring $B^a$ is more preferably a 5- or 6-membered monocyclic aromatic heterocycle (e.g., imidazole, pyrazole, triazole, pyridine, pyrimidine) optionally substituted by 1 to 3 substituents selected from a halogen atom (e.g., a chlorine atom, a bromine atom) and a cyano group.

$L^a$ is a bond, or a spacer having 1 to 3 atoms in the main chain.

Examples of the "spacer having 1 to 3 atoms in the main chain" for $L^a$ include —CH$_2$—, —NH—, —O—, —S—, —C(O)—, —S(O)—, S(O)$_2$—; —CH$_2$CH$_2$—, —CH=CH—, —C≡C—, —NHCH$_2$—, —CH$_2$NH—, —OCH$_2$—, —CH$_2$O—, —SCH$_2$—, —CH$_2$S—, —C(O) CH$_2$—, —CH$_2$C(O)—, —C(O)NH—, —NHC(O)—, —S(O)CH$_2$—, —CH$_2$S(O)—, —S(O)$_2$CH$_2$—, —CH$_2$S(O)$_2$—, —S(O)$_2$NH—, —NHS(O)$_2$—; —CH$_2$CH$_2$CH$_2$—, —CH=CH—CH$_2$—, —CH=CH—CH$_2$—, —C≡C—CH$_2$—, —CH$_2$—C≡C—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, —CH$_2$CH$_2$S—, —S(O) CH$_2$CH$_2$—, —CH$_2$S(O)CH$_2$—, —CH$_2$CH$_2$S(O)—, —S(O)$_2$ CH$_2$CH$_2$—, —CH$_2$S(O)$_2$CH$_2$—, —CH$_2$CH$_2$S(O)$_2$—, —CH$_2$C(O)NH—, —C(O) NHCH$_2$—, —CH$_2$NHC (O)—, —NHC(O)CH$_2$—, —CH$_2$S(O)$_2$NH—, —S(O)$_2$ NHCH$_2$—, —CH$_2$NHS(O)$_2$—, —NHS(O)$_2$CH$_2$—; and the like, and it is optionally substituted by 1 to 3 $C_{1-6}$ alkyl groups. In each spacer, the left bond is bonded to Ring $B^a$, and the right bond is bonded to $R^{1a}$, $L^a$ is preferably
(1) a bond,
(2) —CH$_2$—,
(3) —CH(CH$_3$)—,
(4) —O—,
(5) —OCH$_2$—,
(6) —CH$_2$C(O)—,
(7) —OCH$_2$CH$_2$—,
(8) —CH$_2$C(O)NH— or
(9) —CH$_2$CH$_2$O—.

$L^a$ is particularly preferably —CH$_2$—.

$R^{1a}$ is an optionally substituted $C_{1-6}$ alkyl group or an optionally substituted cyclic group.

$R^{1a}$ is preferably
(1) a $C_{1-6}$ alkyl group (e.g., methyl, ethyl) optionally substituted by 1 to 3 $C_{1-6}$ alkoxy groups (e.g., methoxy),
(2) a $C_{3-6}$ cycloalkyl group (e.g., cyclopropyl, cyclohexyl) optionally substituted by 1 to 3 halogen atoms (e.g., a fluorine atom),
(3) a $C_{6-10}$ aryl group (e.g., phenyl) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl),
    (iv) a $C_{1-6}$ alkoxy group (e.g., methoxy), and
    (v) an N-mono-$C_{1-6}$ alkyl-carbamoyl group (e.g., methylcarbamoyl),
(4) a 5- or 6-membered aromatic heterocyclic group (e.g., pyrazolyl, oxazolyl, isoxazolyl, oxadiazolyl, thiazolyl, pyridyl, pyrimidinyl, pyridazinyl, pyrazinyl) optionally substituted by 1 to 3 substituents selected from
    (i) a halogen atom (e.g., a fluorine atom, a chlorine atom),
    (ii) a cyano group,
    (iii) a $C_{1-6}$ alkyl group (e.g., methyl), and
    (iv) a $C_{1-6}$ alkoxy group (e.g., methoxy), or
(5) a 4- to 6-membered non-aromatic heterocyclic group (e.g., oxetanyl, pyrrolidinyl, tetrahydrofuranyl, piperidinyl, tetrahydropyranyl) optionally substituted by 1 to 3 substituents selected from
    (i) a $C_{1-6}$ alkyl group (e.g., methyl),
    (ii) a $C_{1-6}$ alkyl-carbonyl group (e.g., acetyl),
    (iii) a $C_{1-6}$ alkoxy-carbonyl group (e.g., tert-butoxycarbonyl), and
    (iv) an oxo group.

$R^{1a}$ is more preferably a $C_{6-10}$ aryl group (e.g., phenyl) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl),
    (iv) a $C_{1-6}$ alkoxy group (e.g., methoxy), and
    (v) an N-mono-$C_{1-6}$ alkyl-carbamoyl group (e.g., methylcarbamoyl).

Compound (I-a) is preferably a compound wherein
$X^a$ is CH, CF or N;
$Y^a$ is CH or N;
Ring $A^a$ is a benzene ring optionally substituted by one fluorine atom, or a pyridine ring, which is represented by the formula:

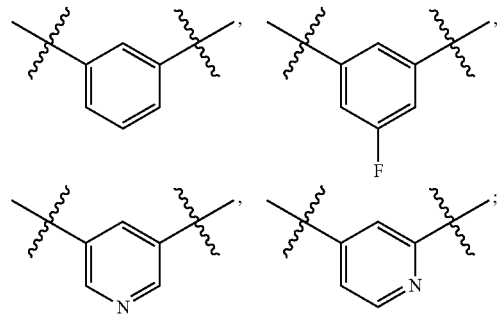

Ring $B^a$ is
(1) a 5- or 6-membered monocyclic aromatic heterocycle (e.g., imidazole, pyrazole, triazole, pyridine, pyrimidine) optionally substituted by 1 to 3 substituents selected from a halogen atom (e.g., a chlorine atom, a bromine atom) and a cyano group,
(2) a 5- or 6-membered non-aromatic heterocycle (e.g., oxazolidine, morpholine, dihydropyridine) optionally substituted by 1 to 3 substituents selected from a $C_{1-6}$ alkyl group (e.g., methyl) and an oxo group, or
(3) a 9- to 14-membered fused bicyclic non-aromatic heterocycle (e.g., tetrahydroindazole);

$L^a$ is
(1) a bond,
(2) —$CH_2$—,
(3) —$CH(CH_3)$—,
(4) —O—,
(5) —$OCH_2$—,
(6) —$CH_2C(O)$—,
(7) —$OCH_2CH_2$—,
(8) —$CH_2C(O)NH$— or
(9) —$CH_2CH_2O$—; and $R^{1a}$ is
(1) a $C_{1-6}$ alkyl group (e.g., methyl, ethyl) optionally substituted by 1 to 3 $C_{1-6}$ alkoxy groups (e.g., methoxy),
(2) a $C_{3-6}$ cycloalkyl group (e.g., cyclopropyl, cyclohexyl) optionally substituted by 1 to 3 halogen atoms (e.g., a fluorine atom),
(3) a $C_{6-10}$ aryl group (e.g., phenyl) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl),
    (iv) a $C_{1-6}$ alkoxy group (e.g., methoxy), and
    (v) an N-mono-$C_{1-6}$ alkyl-carbamoyl group (e.g., methylcarbamoyl),
(4) a 5- or 6-membered aromatic heterocyclic group (e.g., pyrazolyl, oxazolyl, isoxazolyl, oxadiazolyl, thiazolyl, pyridyl, pyrimidinyl, pyridazinyl, pyrazinyl) optionally substituted by 1 to 3 substituents selected from
    (i) a halogen atom (e.g., a fluorine atom, a chlorine atom),
    (ii) a cyano group,
    (iii) a $C_{1-6}$ alkyl group (e.g., methyl), and
    (iv) a $C_{1-6}$ alkoxy group (e.g., methoxy), or
(5) a 4- to 6-membered non-aromatic heterocyclic group (e.g., oxetanyl, pyrrolidinyl, tetrahydrofuranyl, piperidinyl, tetrahydropyranyl) optionally substituted by 1 to 3 substituents selected from
    (i) a $C_{1-6}$ alkyl group (e.g., methyl),
    (ii) a $C_{1-6}$ alkyl-carbonyl group (e.g., acetyl),
    (iii) a $C_{1-6}$ alkoxy-carbonyl group (e.g., tert-butoxycarbonyl), and
    (iv) an oxo group.

Specific examples of compound (I-a) include compounds of Example 1a to Example 47a, Example 49a, Example 53a to Example 68a and Example 70a to Example 95a.

Compound (I-a) is more preferably
5-[(2-{4-[5-(difluoromethyl)-1,3,4-oxadiazol-2-yl]pyridin-2-yl}-1H-imidazol-1-yl)methyl]-2-fluorobenzonitrile or a salt thereof (Example 1a),
2-{4-[5-(difluoromethyl)-1,3,4-oxadiazol-2-yl]pyridin-2-yl}-1-[(3-fluorophenyl)methyl]-1H-imidazole-5-carbonitrile or a salt thereof (Example 82a), or
4-[5-(difluoromethyl)-1,3,4-oxadiazol-2-yl]-2-{1-[(3-fluorophenyl)methyl]-1H-1,2,4-triazol-5-yl}pyridine or a salt thereof (Example 85a).

Compound (I-b)

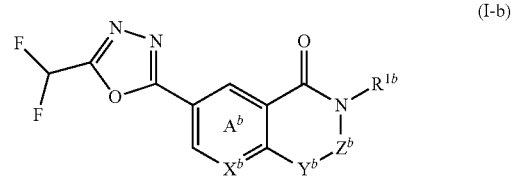

wherein each symbol is as defined above.

$X^b$ is $CR^{2b}$ wherein $R^{2b}$ is a hydrogen atom or a halogen atom, or N.

$X^b$ is preferably CH or N.

Ring $A^b$ is (i) a benzene ring optionally further substituted by 1 or 2 halogen atoms, or (ii) a pyridine ring optionally further substituted by 1 or 2 halogen atoms.

Ring $A^b$ is preferably (i) a benzene ring, or (ii) a pyridine ring.

$Y^b$ is an oxygen atom or an optionally substituted methylene.

$Y^b$ is preferably an oxygen atom or methylene.

$Y^b$ is particularly preferably methylene.

$Z^b$ is $CR^{3b}R^{4b}$ wherein $R^{3b}$ and $R^{4b}$ are each independently a hydrogen atom, an optionally substituted $C_{1-6}$ alkyl group or an optionally substituted cyclic group, or $NR^{5b}$ wherein $R^{5b}$ is an optionally substituted $C_{1-6}$ alkyl group or an optionally substituted cyclic group.

$Z^b$ is preferably
(1) a group represented by $CR^{3b'}R^{4b'}$ wherein
    $R^{3b'}$ is
    (a) a hydrogen atom, or
    (b) a $C_{1-6}$ alkyl group (e.g., methyl) optionally substituted by 1 to 3 $C_{1-6}$ alkoxy groups (e.g., methoxy), and $R^{4b'}$ is
    (a) a hydrogen atom,
    (b) a $C_{3-6}$ cycloalkyl group (e.g., cyclohexyl),
    (c) a $C_{6-10}$ aryl group (e.g., phenyl) optionally substituted by 1 to 3 substituents selected from
        (i) a halogen atom (e.g., a fluorine atom, a chlorine atom),
        (ii) a cyano group,
        (iii) an optionally halogenated $C_{1-6}$ alkyl group (e.g., methyl, trifluoromethyl), and
        (iv) an optionally halogenated $C_{1-6}$ alkoxy group (e.g., methoxy, trifluoromethoxy), or
    (d) a 5- or 6-membered aromatic heterocyclic group (e.g., pyridyl)), or
(2) a group represented by $NR^{5b'}$ wherein
    $R^{5b'}$ is
    (a) an optionally halogenated $C_{1-6}$ alkyl group (e.g., 2,2,2-trifluoroethyl),
    (b) a $C_{3-6}$ cycloalkyl group (e.g., cyclohexyl) optionally substituted by 1 to 3 halogen atoms (e.g., a fluorine atom),
    (c) a $C_{6-10}$ aryl group (e.g., phenyl) optionally substituted by 1 to 3 halogen atoms (e.g., a fluorine atom, a chlorine atom), or
    (d) a 5- or 6-membered non-aromatic heterocyclic group (e.g., tetrahydropyranyl)).

$Z^b$ is more preferably
(1) a group represented by $CR^{3b''}R^{4b''}$ wherein
  $R^{3b''}$ is a $C_{1-6}$ alkyl group (e.g., methyl) optionally substituted by 1 to 3 $C_{1-6}$ alkoxy groups (e.g., methoxy),
  $R^{4b''}$ is a $C_{6-10}$ aryl group (e.g., phenyl) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl), and
    (iv) an optionally halogenated $C_{1-6}$ alkoxy group (e.g., methoxy, trifluoromethoxy)), or
(2) a group represented by $NR^{5b''}$ wherein
  $R^{5b''}$ is a $C_{6-10}$ aryl group (e.g., phenyl) optionally substituted by 1 to 3 halogen atoms (e.g., a fluorine atom, a chlorine atom)).

$R^{1b}$ is a hydrogen atom, an optionally substituted $C_{1-6}$ alkyl group or an optionally substituted cyclic group.

$R^{1b}$ is preferably
(1) a hydrogen atom, or
(2) a $C_{1-6}$ alkyl group (e.g., methyl, ethyl) optionally substituted by 1 to 3 substituents selected from
  (i) a halogen atom (e.g., a fluorine atom),
  (ii) a $C_{3-6}$ cycloalkyl group (e.g., cyclopropyl),
  (iii) a $C_{6-10}$ aryl group (e.g., phenyl), and
  (iv) a $C_{1-6}$ alkoxy group (e.g., methoxy).

Compound (I-b) is preferably a compound wherein
$X^b$ is CH or N;
Ring $A^b$ is (i) a benzene ring, or (ii) a pyridine ring;
$Y^b$ is an oxygen atom or methylene;
$Z^b$ is
(1) a group represented by $CR^{3b'}R^{4b'}$ wherein
  $R^{3b'}$ is
    (a) a hydrogen atom, or
    (b) a $C_{1-6}$ alkyl group (e.g., methyl) optionally substituted by 1 to 3 $C_{1-6}$ alkoxy groups (e.g., methoxy),
  $R^{4b'}$ is
    (a) a hydrogen atom,
    (b) a $C_{3-6}$ cycloalkyl group (e.g., cyclohexyl),
    (c) a $C_{6-10}$ aryl group (e.g., phenyl) optionally substituted by 1 to 3 substituents selected from
      (i) a halogen atom (e.g., a fluorine atom, a chlorine atom),
      (ii) a cyano group,
      (iii) an optionally halogenated $C_{1-6}$ alkyl group (e.g., methyl, trifluoromethyl), and
      (iv) an optionally halogenated $C_{1-6}$ alkoxy group (e.g., methoxy, trifluoromethoxy), or
    (d) a 5- or 6-membered aromatic heterocyclic group (e.g., pyridyl)), or
(2) a group represented by $NR^{5b'}$ wherein
  $R^{5b'}$ is
    (a) an optionally halogenated $C_{1-6}$ alkyl group (e.g., 2,2,2-trifluoroethyl),
    (b) a $C_{3-6}$ cycloalkyl group (e.g., cyclohexyl) optionally substituted by 1 to 3 halogen atoms (e.g., a fluorine atom),
    (c) a $C_{6-10}$ aryl group (e.g., phenyl) optionally substituted by 1 to 3 halogen atoms (e.g., a fluorine atom, a chlorine atom), or
    (d) a 5- or 6-membered non-aromatic heterocyclic group (e.g., tetrahydropyranyl)); and $R^{1b}$ is
(1) a hydrogen atom, or
(2) a $C_{1-6}$ alkyl group (e.g., methyl, ethyl) optionally substituted by 1 to 3 substituents selected from
  (i) a halogen atom (e.g., a fluorine atom),
  (ii) a $C_{3-6}$ cycloalkyl group (e.g., cyclopropyl),
  (iii) a $C_{6-10}$ aryl group (e.g., phenyl), and
  (iv) a $C_{1-6}$ alkoxy group (e.g., methoxy).

Specific examples of compound (I-b) include compounds of Example 1b to Example 56b.

Compound (I-b) is more preferably
3-[5-(difluoromethyl)-1,3,4-oxadiazol-2-yl]-7-(4-fluorophenyl)-6,7-dimethyl-7,8-dihydro-1,6-naphthyridin-5(6H)-one or a salt thereof (Example 1b),
7-[5-(difluoromethyl)-1,3,4-oxadiazol-2-yl]-3-(4-fluorophenyl)-3,4-dihydrophthalazin-1(2H)-one or a salt thereof (Example 2b), or
7-[5-(difluoromethyl)-1,3,4-oxadiazol-2-yl]-2-ethyl-3-(4-fluorophenyl)-3,4-dihydrophthalazin-1(2H)-one or a salt thereof Example 46b Compound (I-c)

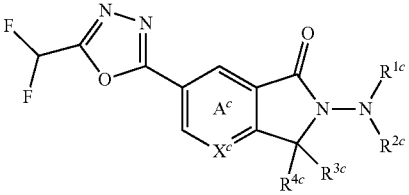

(I-c)

wherein each symbol is as defined above.

$X^c$ is $CR^{5c}$ wherein $R^{5c}$ is a hydrogen atom or a halogen atom, or N.

$X^c$ is preferably CH, or N.

$X^c$ is particularly preferably CH.

Ring $A^c$ is (i) a benzene ring optionally further substituted by 1 or 2 halogen atoms, or (ii) a pyridine ring optionally further substituted by 1 or 2 halogen atoms.

Ring $A^c$ is preferably (i) a benzene ring, or (ii) a pyridine ring.

Ring $A^c$ is particularly preferably a benzene ring.

$R^{1c}$ and $R^{2c}$ are each independently a hydrogen atom or a substituent.

$R^{1c}$ is preferably
(1) a hydrogen atom,
(2) a $C_{1-6}$ alkyl group (e.g., methyl, ethyl) optionally substituted by 1 to 3 substituents selected from
  (i) a $C_{6-10}$ aryl group (e.g., phenyl) optionally substituted by 1 to 3 halogen atoms (e.g., a fluorine atom),
  (ii) a 5- or 6-membered aromatic heterocyclic group (e.g., pyrazolyl) optionally substituted by 1 to 3 $C_{3-6}$ cycloalkyl groups (e.g., cyclopropyl), and
  (iii) a 5- or 6-membered non-aromatic heterocyclic group (e.g., tetrahydropyranyl),
(3) a $C_{1-6}$ alkyl-carbonyl group (e.g., ethylcarbonyl) optionally substituted by 1 to 3 halogen atoms (e.g., a fluorine atom),
(4) a $C_{1-6}$ alkoxy-carbonyl group (e.g., methoxycarbonyl, ethoxycarbonyl, tert-butoxycarbonyl) optionally substituted by 1 to 3 substituents selected from (i) a halogen atom (e.g., a fluorine atom),
(ii) a $C_{1-6}$ alkoxy group (e.g., methoxy), and
(iii) a 5- or 6-membered aromatic heterocyclic group (e.g., pyridyl), (5) a $C_{3-6}$ cycloalkoxy-carbonyl group (e.g., cyclohexyloxycarbonyl) optionally substituted by 1 to 3 $C_{1-6}$ alkoxy groups (e.g., methoxy), (6) a 5- or 6-membered non-aromatic heterocyclyloxycarbonyl group (e.g., tetrahydrofuranyloxycarbonyl, tetrahydropyranyloxycarbonyl), or (7) a $C_{1-6}$ alkylsulfonyl group (e.g., ethylsulfonyl).

$R^{1c}$ is more preferably (1) a $C_{1-6}$ alkyl group (e.g., methyl, ethyl) optionally substituted by 1 to 3 substituents selected from
  (i) a $C_{6-10}$ aryl group (e.g., phenyl) optionally substituted by 1 to 3 halogen atoms (e.g., a fluorine atom),
  (ii) a 5- or 6-membered aromatic heterocyclic group (e.g., pyrazolyl) optionally substituted by 1 to 3 $C_{3-6}$ cycloalkyl groups (e.g., cyclopropyl), and
  (iii) a 5- or 6-membered non-aromatic heterocyclic group (e.g., tetrahydropyranyl), or (2) a $C_{1-6}$ alkoxy-carbonyl group (e.g., methoxycarbonyl, ethoxycarbonyl, tert-butoxycarbonyl) optionally substituted by 1 to 3 substituents selected from
  (i) a halogen atom (e.g., a fluorine atom),
  (ii) a $C_{1-6}$ alkoxy group (e.g., methoxy), and
  (iii) a 5- or 6-membered aromatic heterocyclic group (e.g., pyridyl).

$R^{2c}$ is preferably (1) a $C_{1-6}$ alkyl group (e.g., methyl, ethyl, propyl, isobutyl) optionally substituted by 1 to 3 substituents selected from
  (i) a halogen atom (e.g., a fluorine atom),
  (ii) a $C_{3-6}$ cycloalkyl group (e.g., cyclobutyl, cyclohexyl) optionally substituted by 1 to 3 halogen atoms (e.g., a fluorine atom),
  (iii) a $C_{6-10}$ aryl group (e.g., phenyl) optionally substituted by 1 to 3 substituents selected from
    (a) a halogen atom (e.g., a fluorine atom, a chlorine atom),
    (b) a hydroxy group,
    (c) an optionally halogenated $C_{1-6}$ alkyl group (e.g., difluoromethyl),
    (d) a $C_{1-6}$ alkoxy group (e.g., methoxy, ethoxy) optionally substituted by 1 to 3 $C_{1-6}$ alkoxy groups (e.g., methoxy),
    (e) a $C_{1-6}$ alkoxy-carbonyl group (e.g., methoxycarbonyl),
    (f) a di-$C_{1-6}$ alkylamino group (e.g., dimethylamino),
    (g) a $C_{1-6}$ alkyl-carbonylamino group (e.g., acetylamino),
    (h) a 5- or 6-membered aromatic heterocyclic group (e.g., pyrazinyl),
    (i) a 5- or 6-membered non-aromatic heterocyclic group (e.g., morpholinyl), and
    (j) a 5- or 6-membered aromatic heterocyclyloxy group (e.g., pyrazinyloxy),
  (iv) a $C_{7-16}$ aralkyloxy group (e.g., benzyloxy),
  (v) a $C_{1-6}$ alkoxy-carbonyl group (e.g., ethoxycarbonyl),
  (vi) a 5- or 6-membered aromatic heterocyclic group (e.g., pyrazolyl, pyridyl) optionally substituted by 1 to 3 substituents selected from
    (a) a halogen atom (e.g., a fluorine atom, a chlorine atom), and
    (b) a $C_{3-6}$ cycloalkyl group (e.g., cyclopropyl),
  (vii) a 5- or 6-membered non-aromatic heterocyclic group (e.g., tetrahydropyranyl), and
  (viii) a 8- to 14-membered fused polycyclic aromatic heterocyclic group (e.g., imidazopyridyl, isoquinolyl), (2) a $C_{3-6}$ cycloalkyl group (e.g., cyclopropyl, cyclohexyl) optionally substituted by 1 to 3 halogen atoms (e.g., a fluorine atom), (3) a $C_{6-10}$ aryl group (e.g., phenyl) optionally substituted by 1 to 5 halogen atoms (e.g., a fluorine atom, a chlorine atom), (4) a 5- or 6-membered aromatic heterocyclic group (e.g., pyridyl) optionally substituted by 1 to 3 halogen atoms (e.g., a fluorine atom), (5) a 5- or 6-membered non-aromatic heterocyclic group (e.g., tetrahydropyranyl), or (6) a $C_{1-6}$ alkoxy-carbonyl group (e.g., tert-butoxycarbonyl).

$R^{2c}$ is more preferably a $C_{1-6}$ alkyl group (e.g., methyl, ethyl, propyl, isobutyl) optionally substituted by 1 to 3 substituents selected from
  (i) a halogen atom (e.g., a fluorine atom),
  (ii) a $C_{3-6}$ cycloalkyl group (e.g., cyclobutyl, cyclohexyl) optionally substituted by 1 to 3 halogen atoms (e.g., a fluorine atom),
  (iii) a $C_{6-10}$ aryl group (e.g., phenyl) optionally substituted by 1 to 3 substituents selected from
    (a) a halogen atom (e.g., a fluorine atom, a chlorine atom),
    (b) a hydroxy group,
    (c) an optionally halogenated $C_{1-6}$ alkyl group (e.g., difluoromethyl),
    (d) a $C_{1-6}$ alkoxy group (e.g., methoxy, ethoxy) optionally substituted by 1 to 3 $C_{1-6}$ alkoxy groups (e.g., methoxy),
    (e) a $C_{1-6}$ alkoxy-carbonyl group (e.g., methoxycarbonyl),
    (f) a di-$C_{1-6}$ alkylamino group (e.g., dimethylamino),
    (g) a $C_{1-6}$ alkyl-carbonylamino group (e.g., acetylamino),
    (h) a 5- or 6-membered aromatic heterocyclic group (e.g., pyrazinyl),
    (i) a 5- or 6-membered non-aromatic heterocyclic group (e.g., morpholinyl), and
    (j) a 5- or 6-membered aromatic heterocyclyloxy group (e.g., pyrazinyloxy),
  (iv) a $C_{7-16}$ aralkyloxy group (e.g., benzyloxy),
  (v) a $C_{1-6}$ alkoxy-carbonyl group (e.g., ethoxycarbonyl),
  (vi) a 5- or 6-membered aromatic heterocyclic group (e.g., pyrazolyl, pyridyl) optionally substituted by 1 to 3 substituents selected from
    (a) a halogen atom (e.g., a fluorine atom, a chlorine atom), and
    (b) a $C_{3-6}$ cycloalkyl group (e.g., cyclopropyl),
  (vii) a 5- or 6-membered non-aromatic heterocyclic group (e.g., tetrahydropyranyl), and
  (viii) a 8- to 14-membered fused polycyclic aromatic heterocyclic group (e.g., imidazopyridyl, isoquinolyl).

$R^{3c}$ and $R^{4c}$ are each independently a hydrogen atom, an optionally substituted $C_{1-6}$ alkyl group or an optionally substituted $C_{1-6}$ alkoxy group.

$R^{3c}$ and $R^{4c}$ are preferably both hydrogen atoms.

Compound (I-c) is preferably a compound wherein
$X^c$ is CH, or N;
Ring $A^c$ is (i) a benzene ring, or (ii) a pyridine ring;

R¹ᶜ is
(1) a hydrogen atom,
(2) a $C_{1-6}$ alkyl group (e.g., methyl, ethyl) optionally substituted by 1 to 3 substituents selected from
   (i) a $C_{6-10}$ aryl group (e.g., phenyl) optionally substituted by 1 to 3 halogen atoms (e.g., a fluorine atom),
   (ii) a 5- or 6-membered aromatic heterocyclic group (e.g., pyrazolyl) optionally substituted by 1 to 3 $C_{3-6}$ cycloalkyl groups (e.g., cyclopropyl), and
   (iii) a 5- or 6-membered non-aromatic heterocyclic group (e.g., tetrahydropyranyl),
(3) a $C_{1-6}$ alkyl-carbonyl group (e.g., ethylcarbonyl) optionally substituted by 1 to 3 halogen atoms (e.g., a fluorine atom),
(4) a $C_{1-6}$ alkoxy-carbonyl group (e.g., methoxycarbonyl, ethoxycarbonyl, tert-butoxycarbonyl) optionally substituted by 1 to 3 substituents selected from
   (i) a halogen atom (e.g., a fluorine atom),
   (ii) a $C_{1-6}$ alkoxy group (e.g., methoxy), and
   (iii) a 5- or 6-membered aromatic heterocyclic group (e.g., pyridyl),
(5) a $C_{3-6}$ cycloalkoxy-carbonyl group (e.g., cyclohexyloxycarbonyl) optionally substituted by 1 to 3 $C_{1-6}$ alkoxy groups (e.g., methoxy),
(6) a 5- or 6-membered non-aromatic heterocyclyloxycarbonyl group (e.g., tetrahydrofuranyloxycarbonyl, tetrahydropyranyloxycarbonyl), or
(7) a $C_{1-6}$ alkylsulfonyl group (e.g., ethylsulfonyl);

R²ᶜ is
(1) a $C_{1-6}$ alkyl group (e.g., methyl, ethyl, propyl, isobutyl) optionally substituted by 1 to 3 substituents selected from
   (i) a halogen atom (e.g., a fluorine atom),
   (ii) a $C_{3-6}$ cycloalkyl group (e.g., cyclobutyl, cyclohexyl) optionally substituted by 1 to 3 halogen atoms (e.g., a fluorine atom),
   (iii) a $C_{6-10}$ aryl group (e.g., phenyl) optionally substituted by 1 to 3 substituents selected from
      (a) a halogen atom (e.g., a fluorine atom, a chlorine atom),
      (b) a hydroxy group,
      (c) an optionally halogenated $C_{1-6}$ alkyl group (e.g., difluoromethyl),
      (d) a $C_{1-6}$ alkoxy group (e.g., methoxy, ethoxy) optionally substituted by 1 to 3 $C_{1-6}$ alkoxy groups (e.g., methoxy),
      (e) a $C_{1-6}$ alkoxy-carbonyl group (e.g., methoxycarbonyl),
      (f) a di-$C_{1-6}$ alkylamino group (e.g., dimethylamino),
      (g) a $C_{1-6}$ alkyl-carbonylamino group (e.g., acetylamino),
      (h) a 5- or 6-membered aromatic heterocyclic group (e.g., pyrazinyl),
      (i) a 5- or 6-membered non-aromatic heterocyclic group (e.g., morpholinyl), and
      (j) a 5- or 6-membered aromatic heterocyclyloxy group (e.g., pyrazinyloxy),
   (iv) a $C_{7-16}$ aralkyloxy group (e.g., benzyloxy),
   (v) a $C_{1-6}$ alkoxy-carbonyl group (e.g., ethoxycarbonyl),
   (vi) a 5- or 6-membered aromatic heterocyclic group (e.g., pyrazolyl, pyridyl) optionally substituted by 1 to 3 substituents selected from
      (a) a halogen atom (e.g., a fluorine atom, a chlorine atom), and
      (b) a $C_{3-6}$ cycloalkyl group (e.g., cyclopropyl),
   (vii) a 5- or 6-membered non-aromatic heterocyclic group (e.g., tetrahydropyranyl), and
   (viii) a 8- to 14-membered fused polycyclic aromatic heterocyclic group (e.g., imidazopyridyl, isoquinolyl),
(2) a $C_{3-6}$ cycloalkyl group (e.g., cyclopropyl, cyclohexyl) optionally substituted by 1 to 3 halogen atoms (e.g., a fluorine atom),
(3) a $C_{6-10}$ aryl group (e.g., phenyl) optionally substituted by 1 to 5 halogen atoms (e.g., a fluorine atom, a chlorine atom),
(4) a 5- or 6-membered aromatic heterocyclic group (e.g., pyridyl) optionally substituted by 1 to 3 halogen atoms (e.g., a fluorine atom),
(5) a 5- or 6-membered non-aromatic heterocyclic group (e.g., tetrahydropyranyl), or
(6) a $C_{1-6}$ alkoxy-carbonyl group (e.g., tert-butoxycarbonyl); and R³ᶜ and R⁴ᶜ are both hydrogen atoms.

Specific examples of compound (I-c) include compounds of Example 1c to Example 19c, Example 21c to Example 66c and Example 68c to Example 71c.

Compound (I-c) is more preferably
6-[5-(difluoromethyl)-1,3,4-oxadiazol-2-yl]-2-{[(4-fluorophenyl)methyl][(oxan-4-yl)methyl]amino}-2,3-dihydro-1H-isoindol-1-one or a salt thereof (Example 2c),
2-{[(5-chloropyridin-3-yl)methyl](methyl)amino}-6-[5-(difluoromethyl)-1,3,4-oxadiazol-2-yl]-2,3-dihydro-1H-isoindol-1-one or a salt thereof (Example 60c), or
2-{[(3,3-difluorocyclobutyl)methyl](methyl)amino}-6-[5-(difluoromethyl)-1,3,4-oxadiazol-2-yl]-2,3-dihydro-1H-isoindol-1-one or a salt thereof (Example 64c).

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of compound (I) is explained below.

The raw material compound and reagent used and the compound obtained in each step in the following production method may be each in a form of a salt, and examples of such salt include those similar to the salts of compound (I) and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like; amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like; esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogencarbonate, cesium carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as reagents.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, a method using diphenylphosphorylazide, triphenylphosphine and azodicarboxylate, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSC HCl) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride, trichloroisocyanuric acid and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, a electrophile (e.g., an alkyl halide etc.) and a base (e.g., an organic base, an inorganic base, a metal alkoxide, a metal amide etc.) are used as reagents.

When cyanidation reaction is carried out in each step, examples of the reagent to be used include metal cyanides such as copper cyanide, potassium cyanide and the like.

Compound (I) can be produced according to the following production methods shown below. Each symbol in the formulas of the schemes is as defined above, unless otherwise specified. $P^1$ is a "protecting group for an amino group". Examples of the "protecting group for an amino group" include a [2-(triethylsilyl)ethoxy]methyl group and the like, in addition to the protecting group for an amino group which is exemplified above. Hal is a halogen atom (e.g., a chlorine atom, a bromine atom, an iodine atom). LG is a leaving group (e.g., a halogen atom (a chlorine atom, a bromine atom, an iodine atom), or a $C_{1-6}$ alkylsulfonyloxy group (e.g., methylsulfonyloxy), etc.). M is an optionally substituted metal atom (e.g., magnesium bromide, trimethylstannyl).

Moreover, compound (I) can be produced by carrying out protection reaction, deprotection reaction, amidation reaction, sulfonamidation reaction, urea formation reaction, carbamoylation reaction, alkylation reaction, Mitsunobu reaction, hydrogenation reaction, oxidation reaction, reduction reaction, halogenation reaction, coupling reaction, nucleophilic addition reaction by a carbo anion, Grignard reaction, deoxofluorination reaction, dehydration reaction and the like singly or two or more thereof in combination.

Production of Compound (I-a)

Production Method A-1

Among compound (I-a), the below-mentioned compound (I-aa) (compound (I-a) wherein Ring $B^a$ is an imidazole ring having $-L^a-R^{1a}$ at the 1-position), compound (I-ab) (compound (I-a) wherein Ring $B^a$ is an imidazole ring having $-L^a-R^{1a}$ at the 1-position and a halogen atom at the 5-position) and compound (I-ac) (compound (I-a) wherein Ring $B^a$ is an imidazole ring having $-L^a-R^{1a}$ at the 1-position and a cyano group at the 5-position) can be produced according to the following method.

(Scheme 1)

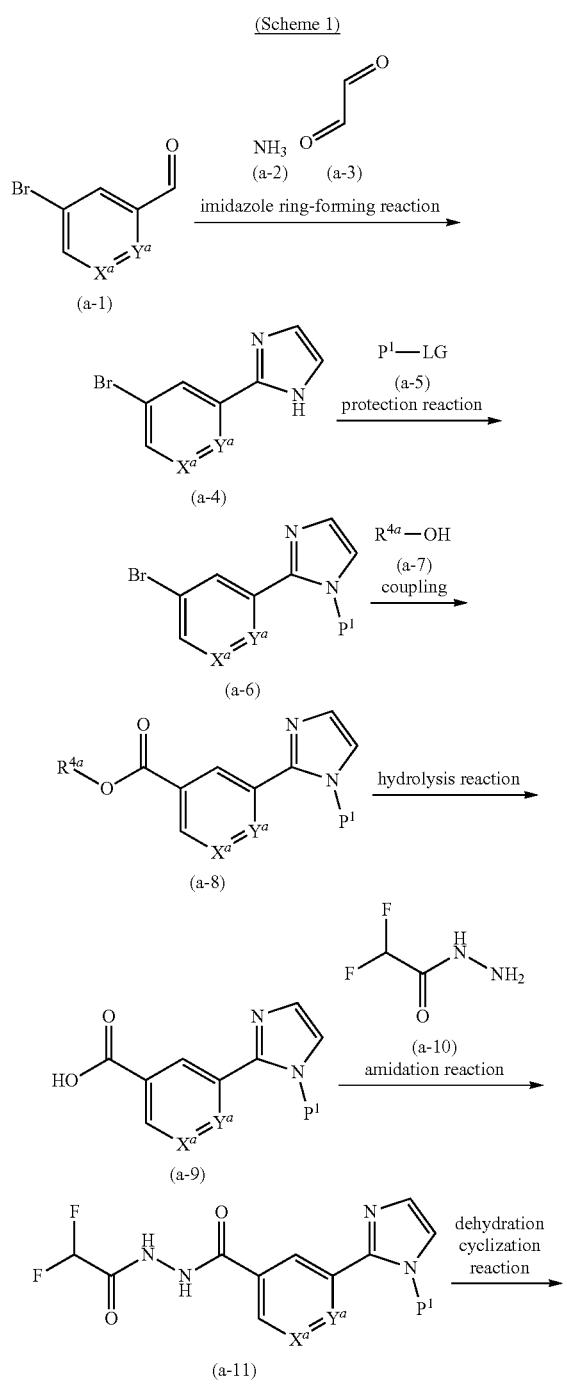

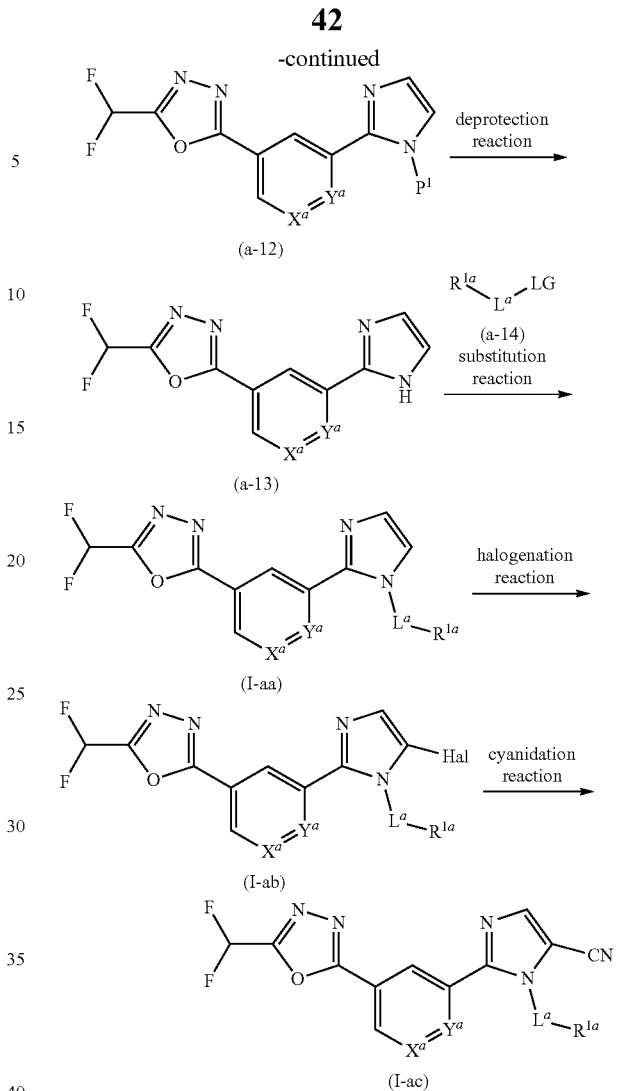

wherein $R^{4a}$ is an optionally substituted $C_{1-6}$ alkyl group (e.g., a methyl group, an ethyl group), and the other symbols are as defined above.

Compound (a-4) can be produced by subjecting compound (a-1) to an imidazole ring-forming reaction. Examples of the reagent to be used include a combination of ammonia (a-2) and glyoxal (a-3), and the like.

Compound (a-6) can be produced by subjecting compound (a-4) to a protection reaction with compound (a-5).

Compound (a-8) can be produced by coupling compound (a-6) with compound (a-7) under carbon monoxide atmosphere, using a palladium catalyst and a base. Examples of the palladium catalyst include 1,1'-bis(diphenylphosphino)ferrocenepalladium(II) chloride and the like. Examples of the base include triethylamine.

Compound (a-9) can be produced by subjecting compound (a-8) to a hydrolysis reaction.

Compound (a-11) can be produced by subjecting compound (a-9) to an amidation reaction with compound (a-10).

Compound (a-12) can be produced by subjecting compound (a-11) to a dehydration cyclization reaction. A combination of the Burgess reagent or p-toluenesulfonyl chloride and a base is used as reagents. Examples of the base include the above-mentioned organic bases (e.g., N,N-diisopropylethylamine, triethylamine, etc.).

Compound (a-13) can be produced by subjecting compound (a-12) to a deprotection reaction. Examples of the reagent to be used include boron trifluoride etherate and the like.

Compound (I-aa) can be produced by subjecting compound (a-13) to a substitution reaction with compound (a-14) in the presence of a base. Examples of the base include the above-mentioned inorganic bases (e.g., cesium carbonate, etc.).

Compound (I-ab) can be produced by subjecting compound (I-aa) to a halogenation reaction. Examples of the reagent to be used include N-bromosuccinimide (NBS) and the like.

Compound (I-ac) can be produced by subjecting compound (I-ab) to a cyanidation reaction. Examples of the reagent to be used include copper cyanide and the like.

Production Method A-2

Among compound (I-a), the below-mentioned compound (I-ad) (compound (I-a) wherein $B^a$ ring is a 2-oxo-1,2-dihydropyridine ring having $R^{5a}$ at the 1-position and $OR^{1a}$ at the 4-position) can be produced according to the following method.

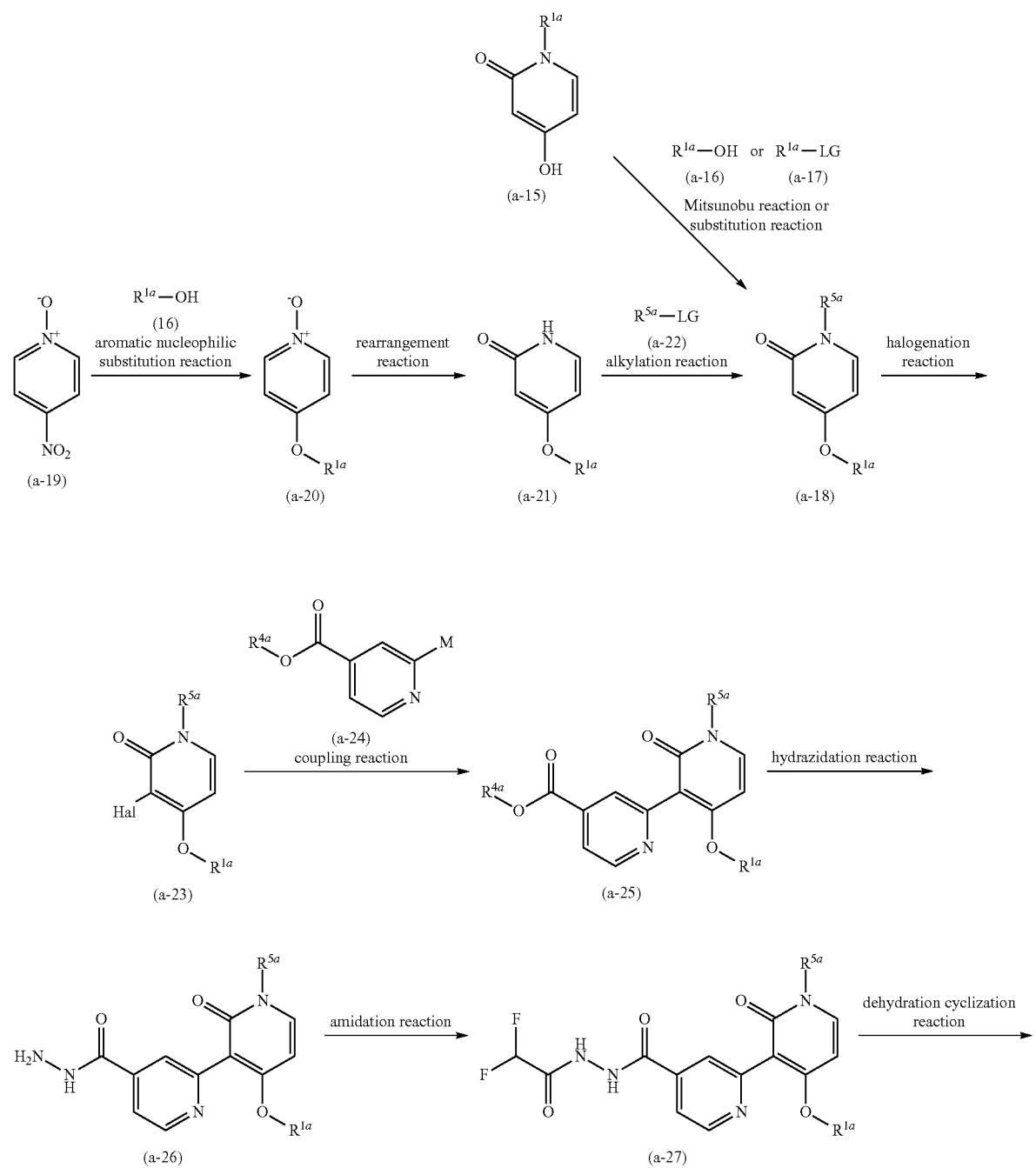

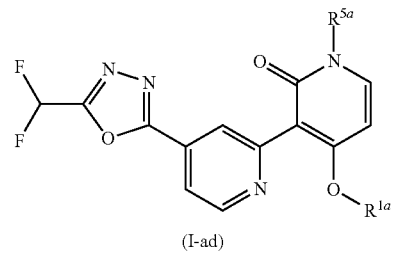

(I-ad)

wherein $R^{5a}$ is an optionally substituted $C_{1-6}$ alkyl group (e.g., methyl, ethyl), and the other symbols are as defined above.

Compound (a-18) can be produced by subjecting compound (a-15) to the Mitsunobu reaction with compound (a-16). Examples of the reagent to be used include a combination of diethyl azodicarboxylate (DEAD) and triphenylphosphine and the like.

In addition, compound (a-18) can also be produced by subjecting compound (a-15) to a substitution reaction with compound (a-17) in the presence of a base. Examples of the base include the above-mentioned alkali metal hydrides (e.g., sodium hydride, etc.).

Moreover, compound (a-18) can also be produced via compound (a-20) and compound (a-21) from compound (a-19) as a raw material. Compound (a-20) can be produced by subjecting compound (a-19) to an aromatic nucleophilic substitution reaction with compound (a-16) in the presence of a base. Examples of the base include the above-mentioned inorganic bases (e.g., potassium carbonate, etc.). Compound (a-21) can be produced by subjecting compound (a-20) to a rearrangement reaction. Examples of the reagent to be used include anhydrides (e.g., acetic anhydride, trifluoroacetic anhydride, etc.). Compound (a-18) can be produced by subjecting compound (a-21) to an alkylation reaction with compound (a-22) in the presence of a base. Examples of the base include the above-mentioned inorganic bases (e.g., potassium carbonate, etc.).

Compound (a-23) can be produced by subjecting compound (a-18) to a halogenation reaction. Examples of the reagent to be used include N-iodosuccinimide (NIS) and the like.

Compound (a-25) can be produced by subjecting compound (a-23) to a coupling reaction with compound (a-24) using a palladium catalyst. Examples of the palladium catalyst include tetrakis(triphenylphosphine)palladium(0) and the like. Examples of the optionally substituted metal atom for M include a trimethylstannyl group and the like.

Compound (a-26) can be produced by subjecting compound (a-25) to a hydrazidation reaction. Examples of the hydrazidating agent include hydrazine monohydrate and the like.

Compound (a-27) can be produced by subjecting compound (a-26) to an amidation reaction.

Compound (I-ad) can be produced by subjecting compound (a-27) to a dehydration cyclization reaction.

Compound (a-1), compound (a-2), compound (a-3), compound (a-5), compound (a-7), compound (a-10), compound (a-14), compound (a-15), compound (a-16), compound (a-17), compound (a-19), compound (a-22) and compound (a-24) used as raw materials in the above-mentioned production methods may be a commercially available product, or can be produced according to a method known per se.

Production of Compound (I-b)
Production Method B-1

Among compound (I-b), the below-mentioned compound (I-ba) (compound (I-b) wherein $X^b$ is N, $Y^b$ is $CH_2$, and $Z^b$ is $CR^{3b}R^{4b}$) can be produced according to the following method.

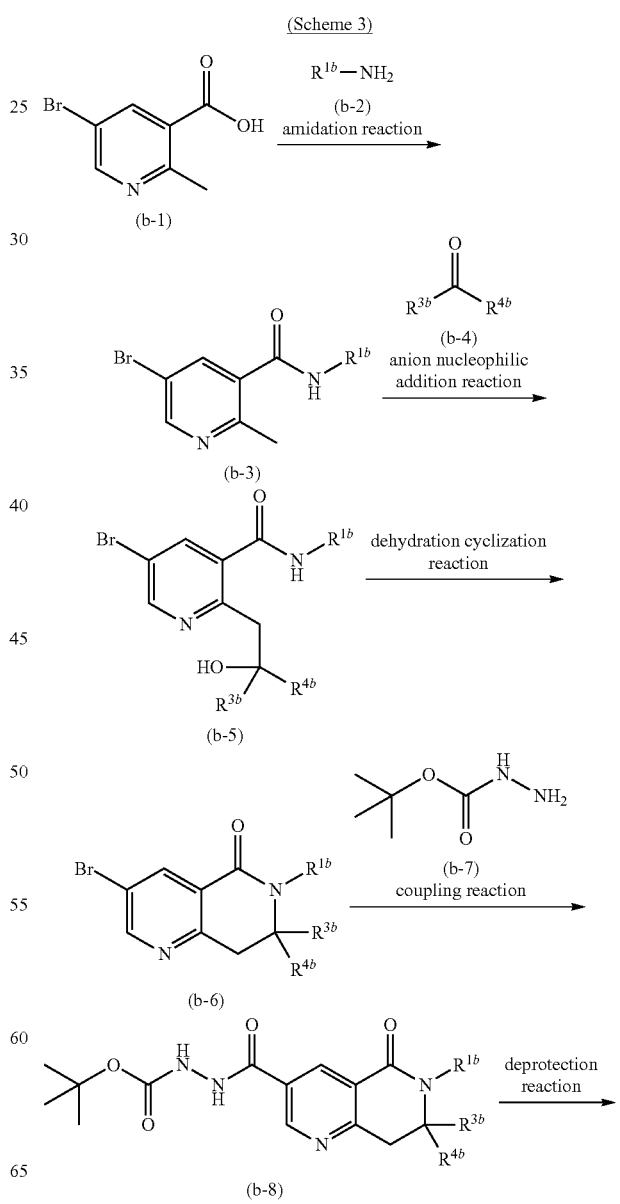

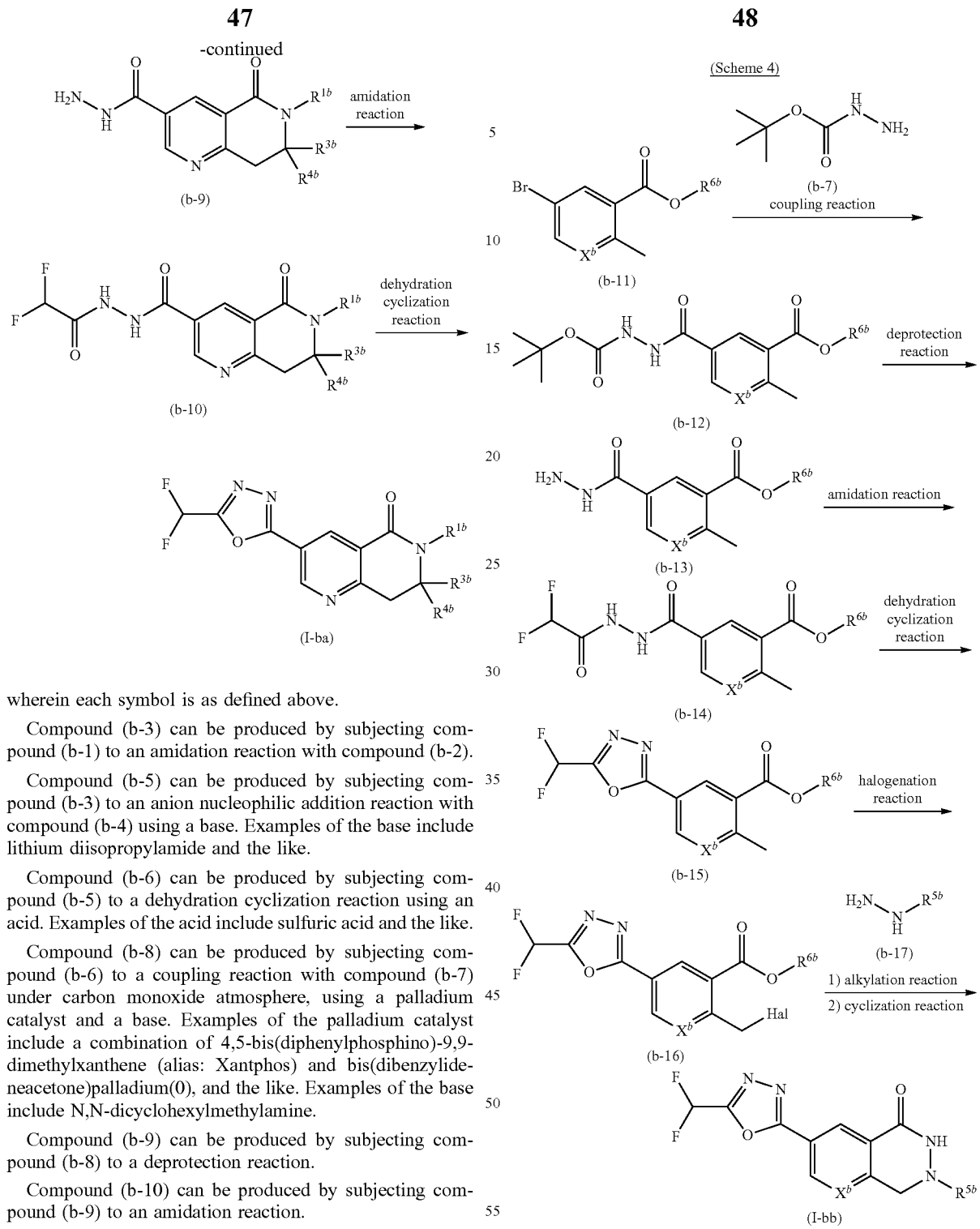

(Scheme 4)

wherein each symbol is as defined above.

Compound (b-3) can be produced by subjecting compound (b-1) to an amidation reaction with compound (b-2).

Compound (b-5) can be produced by subjecting compound (b-3) to an anion nucleophilic addition reaction with compound (b-4) using a base. Examples of the base include lithium diisopropylamide and the like.

Compound (b-6) can be produced by subjecting compound (b-5) to a dehydration cyclization reaction using an acid. Examples of the acid include sulfuric acid and the like.

Compound (b-8) can be produced by subjecting compound (b-6) to a coupling reaction with compound (b-7) under carbon monoxide atmosphere, using a palladium catalyst and a base. Examples of the palladium catalyst include a combination of 4,5-bis(diphenylphosphino)-9,9-dimethylxanthene (alias: Xantphos) and bis(dibenzylideneacetone)palladium(0), and the like. Examples of the base include N,N-dicyclohexylmethylamine.

Compound (b-9) can be produced by subjecting compound (b-8) to a deprotection reaction.

Compound (b-10) can be produced by subjecting compound (b-9) to an amidation reaction.

Compound (I-ba) can be produced by subjecting compound (b-10) to a dehydration cyclization reaction. A combination of the Burgess reagent or p-toluenesulfonyl chloride and a base is used as reagents. Examples of the base include the above-mentioned organic bases (e.g., N,N-diisopropylethylamine, triethylamine, etc.).

Production Method B-2

Among compound (I-b), the below-mentioned compound (I-bb) (compound (I-b) wherein $R^{1b}$ is a hydrogen atom, $Y^b$ is $CH_2$, and $Z^b$ is $NR^{5b}$) can be produced according to the following method.

wherein $R^{6b}$ is an optionally substituted $C_{1-6}$ alkyl group (e.g., methyl, ethyl), and the other symbols are as defined above.

Compound (b-12) can be produced by subjecting compound (b-11) to a coupling reaction with compound (b-7) using a palladium catalyst and a base, under carbon, monoxide atmosphere. Examples of the palladium catalyst include a combination of 4,5-bis(diphenylphosphino)-9,9-dimethylxanthene (alias: Xantphos) and bis(dibenzylideneacetone)palladium(0) and the like. Examples of the base include N,N-dicyclohexylmethylamine.

Compound (b-13) can be produced by subjecting compound (b-12) to a deprotection reaction.

Compound (b-14) can be produced by subjecting compound (b-13) to an amidation reaction.

Compound (b-15) can be produced by subjecting compound (b-14) to a dehydration cyclization reaction. A combination of the Burgess reagent or p-toluenesulfonyl chloride and a base is used as reagents. Examples of the base include the above-mentioned organic bases (e.g., N,N-diisopropylethylamine, triethylamine, etc.).

Compound (b-16) can be produced by subjecting compound (b-15) to a halogenation reaction. Examples of the reagent to be used include N-bromosuccinimide (NBS) and the like.

Compound (I-bb) can be produced by subjecting compound (b-16) to an alkylation reaction with compound (b-17), followed by a cyclization reaction. The cyclization reaction follows the alkylation reaction, but it may be progressed step by step. In the latter case, the cyclization reaction can be progressed under a basic condition. Examples of the base include triethylamine and the like.

Compound (b-1), compound (b-2), compound (b-4), compound (b-7) and compounds (b-11) and (b-17) used as raw materials in the above-mentioned production methods may be a commercially available product, or can be produced according to a method known per se.

Production of Compound (I-c)

Production Method C-1

Among compound (I-c), the below-mentioned compound (I-ca) (compound (I-c) wherein $R^{2c}$, $R^{3c}$ and $R^{4c}$ are hydrogen atoms) and compound (I-cb) (compound (I-c) wherein $R^{2c}$ is $CHR^{7c}R^{8c}$ (the $CHR^{7c}R^{8c}$ corresponds to a part of the substituent defined by $R^{2c}$), and $R^{3c}$ and $R^{4c}$ are hydrogen atoms) can be produced according to the following method.

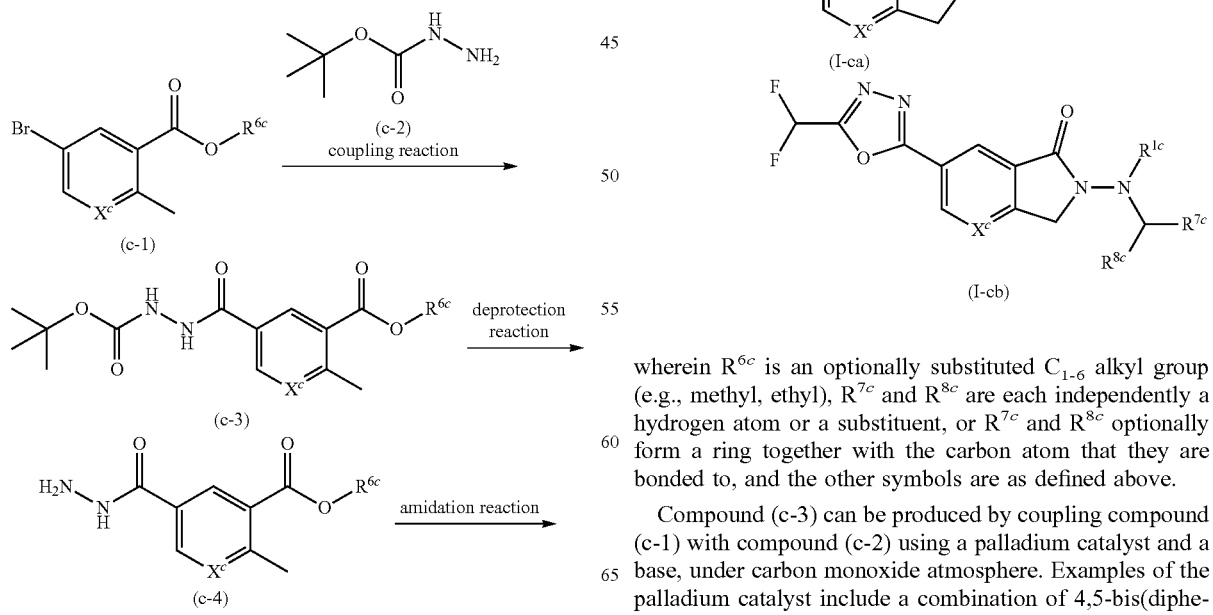

wherein $R^{6c}$ is an optionally substituted $C_{1-6}$ alkyl group (e.g., methyl, ethyl), $R^{7c}$ and $R^{8c}$ are each independently a hydrogen atom or a substituent, or $R^{7c}$ and $R^{8c}$ optionally form a ring together with the carbon atom that they are bonded to, and the other symbols are as defined above.

Compound (c-3) can be produced by coupling compound (c-1) with compound (c-2) using a palladium catalyst and a base, under carbon monoxide atmosphere. Examples of the palladium catalyst include a combination of 4,5-bis(diphenylphosphino)-9,9-dimethylxanthene (alias: Xantphos) and bis(dibenzylideneacetone)palladium(0), and the like. Examples of the base include N,N-dicyclohexylmethylamine.

Compound (c-4) can be produced by subjecting compound (c-3) to a deprotection reaction.

Compound (c-5) can be produced by subjecting compound (c-4) to an amidation reaction.

Compound (c-6) can be produced by subjecting compound (c-5) to a dehydration cyclization reaction. A combination of the Burgess reagent or p-toluenesulfonyl chloride and a base is used as reagents. Examples of the base include the above-mentioned organic bases (e.g., N,N-diisopropylethylamine, triethylamine, etc.).

Compound (c-7) can be produced by subjecting compound (c-6) to a halogenation reaction. Examples of the reagent to be used include N-bromosuccinimide (NBS) and the like.

Compound (c-9) can be produced by subjecting compound (c-7) to an alkylation reaction with compound (c-8), followed by a cyclization reaction. The cyclization reaction follows the alkylation reaction, but it may be progressed step by step. In the latter case, the cyclization reaction can be progressed under a basic condition. Examples of the base include triethylamine and the like.

Compound (I-ca) can be produced by subjecting compound (c-9) to a deprotection with an acid. Examples of the acid include hydrochloric acid, trifluoroacetic acid and the like.

Compound (I-cb) can be produced by subjecting compound (I-ca) to a reductive amination reaction with compound (c-10). Examples of the reducing agent to be used include triethylsilane, sodium cyanoborohydride and the like.

Production Method C-2

Among compound (I-c), the below-mentioned compound (I-cc) (compound (I-c) wherein $R^{1c}$ is $CHR^{9c}R^{10c}$ (the $CHR^{9c}R^{10c}$ corresponds to a part of the substituent defined by $R^{1c}$), $R^{2c}$ is $CHR^{7c}R^{8c}$ (the $CHR^{7c}R^{8c}$ corresponds to a part of the substituent defined by $R^{2c}$), and $R^{3c}$ and $R^{4c}$ are hydrogen atoms) can be produced according to the following method.

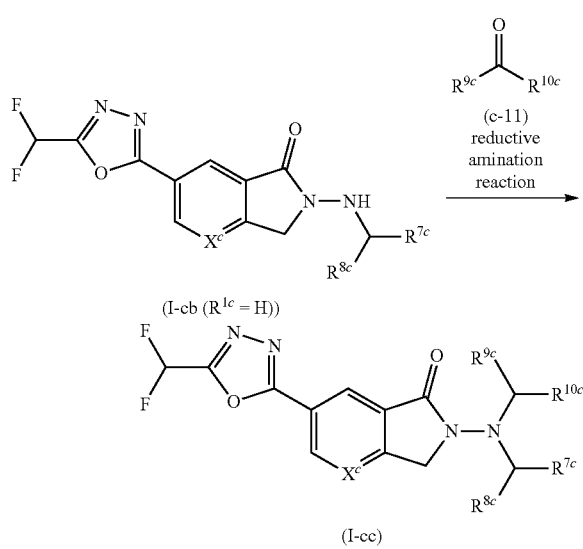

wherein $R^{9c}$ and $R^{10c}$ are each independently a hydrogen atom or a substituent, or $R^{9c}$ and $R^{10c}$ optionally form a ring together with the carbon atom that they are bonded to, and the other symbols are as defined above.

Compound (I-cc) can be produced by subjecting compound (I-cb ($R^{1c}$=H)), i.e., compound (I-cb) wherein $R^{1c}$ is a hydrogen atom, to a reductive amination reaction with compound (c-11). Examples of the reducing agent to be used include triethylsilane, sodium cyanoborohydride and the like.

Production Method C-3

Among compound (I-c), the below-mentioned compound (I-cd) (compound (I-c) wherein $R^{1c}$ is $CO_2R^{1c}$ (the $CO_2R^{1c}$ corresponds to a part of the substituent defined by $R^{1c}$), $R^{2c}$ is $CHR^{7c}R^{8c}$ (the $CHR^{7c}R^{8c}$ corresponds to a part of the substituent defined by $R^{2c}$), and $R^{3c}$ and $R^{4c}$ are hydrogen atoms) can be produced according to the following method.

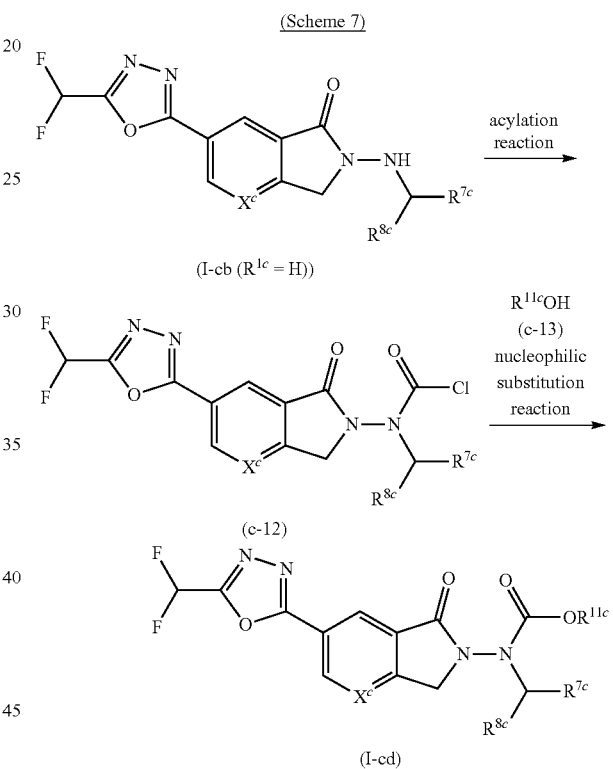

wherein $R^{11c}$ are each independently an optionally substituted hydrocarbon group, and the other symbols are as defined above.

Compound (c-12) can be produced by subjecting compound (I-cb ($R^{1c}$=H)), i.e., compound (I-cb) wherein $R^{1c}$ is a hydrogen atom, to an acylation reaction. Examples of the acylating agent to be used include triphosgene and the like.

Compound (I-cd) can be produced by subjecting compound (c-12) to a nucleophilic substitution reaction with compound (c-13) using a base. Examples of the base to be used include potassium tert-butoxide and the like.

Compound (c-1), compound (c-2), compound (c-8), compound (c-10), compound (c-11) and compound (c-13) used as raw materials in the above-mentioned production methods may be a commercially available product, or can be produced according to a method known per se.

Compound (I) contains a stereoisomer depending on the kind of a substituent, and each stereoisomer and a mixture thereof are encompassed in the present invention.

Compound (I) may be a hydrate or a non-hydrate.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution such as preparative high performance liquid chromatography (preparative HPLC), supercritical fluid chromatography (preparative SFC) and the like.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, isopropyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method may have high purity, high quality, and low hygroscopicity, may not be denatured even after a long-term preservation under general conditions, and may be expected to be superior in the stability. In addition, it may be also superior in the biological properties (e.g., pharmacokinetics (absorption, distribution, metabolism, excretion), efficacy expression etc.) and may be extremely useful as a medicament.

Compound (I) may be a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2$H, $^3$H, $^{11}$C, $^{14}$C, $^{18}$F, $^{35}$S, $^{125}$I) and the like. The compound labeled or substituted with an isotope may be used, for example, as a tracer (PET tracer) used in positron emission tomography (PET), and useful in the field of medical diagnosis and the like.

Compound (I) also encompasses a deuterium conversion form wherein $^1$H is converted to $^2$H(D).

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability). The cocrystal or a salt thereof can be produced according to a cocrystallization a method known per se.

Compound (I) may also be used as a PET tracer.

Since the compound of the present invention has a superior HDAC inhibitory action, preferably class II HDAC inhibitory action, more preferably HDAC6 inhibitory action, it may be also useful as safe medicaments based on such action.

For example, the medicament of the present invention containing the compound of the present invention may be expected to show low toxicity (e.g., acute toxicity, chronic toxicity, genetic toxicity, reproductive toxicity, cardiotoxicity, carcinogenicity), and used for a mammal (e.g., mouse, rat, hamster, rabbit, cat, dog, bovine, sheep, monkey, human) as a prophylactic or therapeutic agent for HDAC-associated diseases, preferably class II HDAC-associated diseases, more preferably HDAC6-associated diseases, more specifically, the diseases described in (1)-(7) below.

Particularly, the compound of the present invention may be expected to show low genetic toxicity, and therefore, the medicament of the present invention may be expected to show low genetic toxicity.

(1) inflammatory diseases (e.g., acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, diabetic nephropathy, uveitis, suppurative hidradenitis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, Addison's disease, abnormal immunoresponse, arthritis, dermatitis, radiodermatitis, primary biliary cirrhosis etc.), (3) ostecarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, metastasis melanoma, Kaposi's sacroma, vascular proliferation, cachexia, metastasis of the breast cancer, cancer (e.g., colorectal cancer (e.g., familial colorectal cancer, hereditary non-polyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor fibrous histiocytoma, leiomyosarcoma, rhabdomyosarcoma, cancer of unknown primary), leukemia (e.g., acute leukemia (e.g., acute lymphatic leukemia, acute myelocytic leukemia etc.), chronic leukemia (e.g., chronic lymphatic leukemia, chronic myelocytic leukemia etc.), myelodysplastic syndrome), uterine sarcoma (e.g., mixed mesodermal tumor, uterine leiomyosarcoma, endometrial stromal tumor etc.), myelofibrosis etc.], (5) neurodegenerative diseases and/or central diseases (i) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autistic spectrum syndrome, fragile X syndrome, Rett syndrome, adjustment disorder, bipolar disorder, neurosis, schizophrenia (e.g., positive symptom, negative symptom, cognitive symptom), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, hreditary sastic praplegia], (ii) neurodegenerative diseases [e.g., Alzheimer's disease, dementia of Alzheimer type, Alzheimer-type senile dementia, Parkinson's disease, muscular dystrophy, Parkinson's disease associated with dementia, Huntington's disease, multi-infarct dementia, frontotemporal lobar degeneration [progressive supranuclear palsy, corticobasal degeneration, frontotemporal dementia and parkinsonism linked to MAPT mutation (FTDP-17), frontotemporal dementia, Pick's disease, argyrophilic grain dementia etc.], Parkinson's type dementia, Niemann-Pick syndrome, Down's disease, vascular dementia, postencephalitic parkinsonism, Lewy body dementia, Rubinstein-Taybi syndrome, Charcot-Marie-Tooth disease, HIV dementia, amyotrophic lateral sclerosis (ALS), motor neurogenesis disease (MND), Creutzfeldt-Jakob disease or prion disease, cerebral palsy, multiple sclerosis, Riley-Day syndrome], (iii) age-related cognition memory disorders [e.g., age-related memory disorders, senile dementia], (iv) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (v) respiratory depression caused by anesthetics, traumatic disease, or neurodegenerative disease and the like, (vi) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, peptic ulcer, diarrhea, constipation, postoperative ileus, (vii) pain, (6) chronic heart failure or acute heart failure, acute decompensated heart failure, ischemic heart disease, cardiomyopathy, myocarditis, valvular disease, (7) peripheral neuropathy and the like.

The medicament of the present invention may be preferably used as an agent for the prophylaxis or treatment of autoimmune disease, inflammatory disease, osteoarticular degenerative disease, neurodegenerative disease, central disease, neoplastic disease, or peripheral neuropathy, more preferably inflammatory bowel disease (preferably Crohn's disease or ulcerative colitis), systemic lupus erythematosus, rheumatoid arthritis, psoriasis, Sjogren's syndrome, Behcet's syndrome, multiple sclerosis, graft versus host disease, Alzheimer's disease (preferably dementia of Alzheimer type), schizophrenia, dementia with Lewy Bodies, frontotemporal lobar degeneration [progressive supranuclear palsy, corticobasal degeneration, frontotemporal dementia and parkisonism linked to MAPT mutation (FTDP-17), frontotemporal dementia, Pick's disease, argyrophilic grain dementia etc.], Parkinson's disease, Huntington's disease, Rubinstein-Taybi Syndrome, muscular dystrophy, Rett Syndrome, amyotrophic lateral sclerosis, Charcot-Marie-Tooth disease, depression, hereditary spastic praplegia, Riley-Day syndrome, Castleman's disease, leukemia, uterine leiomyosarcoma, prostate cancer, colon cancer, multiple myeloma, cachexia or myelofibrosis, chronic heart failure or acute heart failure, acute decompensated heart failure, ischemic heart disease, cardiomyopathy, myocarditis, valvular disease, peripheral neuropathy and the like.

The medicament of the present invention may be more preferably used as an agent for the prophylaxis or treatment of Alzheimer's disease, frontotemporal lobar degeneration [progressive supranuclear palsy, corticobasal degeneration, frontotemporal dementia and parkinsonism linked to MAPT mutation (FTDP-17), frontotemporal dementia, Pick's disease, argyrophilic grain dementia etc.] and the like, particularly Alzheimer's disease or progressive supranuclear palsy.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention may be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, so oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and administration to the lesion).

The content of the compound of the present invention in the medicament of the present invention is about 0.01 to 100% by weight of the entire medicament. The dose of the medicament of the present invention may vary depending on administration subject, administration route, disease and the like. For example, for oral administration to patients (body weight about 60 kg) with neurodegenerative disease (for example Alzheimer's disease, progressive supranuclear palsy, etc.), about 0.01 mg/kg body weight-about 50 mg/kg body weight, preferably about 0.05 mg/kg body weight-about 25 mg/kg body weight, more preferably about 0.1 mg/kg body weight-about 2 mg/kg body weight of an active ingredient (compound (I)) may be administered once to several portions per day.

Examples of the pharmaceutically acceptable carrier include various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, and light anhydrous silicic acid.

Examples of the lubricant include magnesium stearate, calcium stearate, talc, and colloidal silica.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of the disintegrant include starch, carboxymethylcellulose, carboxymethylcellulose calcium, carboxymethylstarch sodium, and L-hydroxypropylcellulose.

Examples of the solvent include water for injection, alcohol, propylene glycol, Macrogol, sesame oil, corn oil, and olive oil.

Examples of the solubilizing agent include polyethylene glycol, propylene glycol, D-mannitol, benzyl benzoate, ethanol, trisaminomethane, cholesterol, triethanolamine, and sodium carbonate, sodium citrate.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of the isotonic agent include glucose, D-sorbitol, sodium chloride, glycerin, and D-mannitol.

Examples of the buffering agent include buffer solutions such as phosphates, acetates, carbonates, and citrates.

Examples of the soothing agent include benzyl alcohol.

Examples of the preservative include parahydroxybenzoates, chlorobutanol, benzyl alcohol, phenylethyl alcohol, dehydroacetic acid, and sorbic acid.

Examples of the antioxidant include sulfites, ascorbic acid, and α-tocopherol.

For the prophylaxis or treatment of various diseases, the compound of the present invention may also be used together with other drug (hereinafter, to be referred to as concomitant drug). In the following, a medicament to be used when the compound of the present invention is used together with other drug is referred to as "the combination agent of the present invention".

For example, when the compound of the present invention is used as a HDAC inhibitor, preferably a class II HDAC inhibitor, more preferably a HDAC6 inhibitor, it may be used together with the following drugs.

tranquilizer (diazepam, lorazepam, clorazepate dipotassium, oxazepam, chlordiazepoxide, medazepam, oxazolam, cloxazolam, clotiazepam, bromazepam, etizolam, fludiazepam, hydroxyzine, nitrazepam, triazolam, alprazolam etc.), antipsychotic (chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, clozapine, trifluoperazine dihydrochloride, fluphenazine hydrochloride, olanzapine, quetiapine fumarate, risperidone, aripiprazole, bromperidol, spiperone, reserpine, clocapramine hydrochloride, sulpiride, zotepine, tiotixene etc.), antiepileptic drug (phenytoin, ethosuximide, acetazolamide, chlordiazepoxide, trimethadione, carbamazepine, phenobarbital, primidone, sulthiame, sodium valproate, clonazepam, diazepam, nitrazepam etc.), antidepressant and therapeutic drug for manic psychosis [tricyclic or tetracyclic antidepressant drug (imipramine hydrochloride, clomipramine hydrochloride, desipramine hydrochloride, amitriptyline hydrochloride, nortriptyline hydrochloride, amoxapine, mianserin hydrochloride, maprotiline hydrochloride, etc.), noxiptiline, phenelzine, sulpiride, trazodone hydrochloride, lithium carbonate, selective serotonin reuptake inhibitor (fluvoxamine maleate, fluoxetine hydrochloride, citalopram hydrobromide, sertraline hydrochloride, paroxetine hydrochloride, paroxetine hydrochloride hydrate, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, setiptiline maleate, 5-HT$_{1A}$ agonist (buspirone hydrochloride, tandospirone citrate, osemozotan hydrochloride) etc.]

benzodiazepine (clonazepam etc.), L-type calcium channel inhibitor (pregabalin etc.), 5-HT$_{1A}$ agonist (buspirone hydrochloride, tandospirone citrate, osemozotan hydrochloride etc.), 5-HT$_3$ antagonist (cyamemazine etc.), heart nonselective β inhibitor (propranolol hydrochloride, oxiprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), drug that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, type II carbonic anhydrase inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioids antagonist, opioids agonist, uridine, nicotinic acid receptor agonists, thyroid hormone (T3, T4), TSH, TRH, MAO inhibitor (phenelzine sulfate, tranylcypromine sulfate, moclobemide etc.), $5\text{-}HT_{2A}$ antagonist, $5\text{-}HT_{2A}$ inverse agonist, COMT inhibitor (entacapone, etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug forfibromyalgia, therapeutic drug for headache, therapeutic drug for insomnia (etizolam, zopiclone, triazolam, xolpidem, ramelteon, indiplon etc.), therapeutic drug for quitting smoking, therapeutic drug for myasthenia gravis, therapeutic drug for cerebral infarction, therapeutic drug for manic psychosis, therapeutic drug for hypersomnia, therapeutic drug for pain, therapeutic drug for dysthymia, therapeutic drug for dysautonomia, therapeutic drug for male and female sexual dysfunction, therapeutic drug for migraine, therapeutic drug for pathological gambling, therapeutic drug for restless legs syndrome, therapeutic drug for substance dependence, therapeutic drug for alcohol-related disease, therapeutic drug for irritable bowel syndrome, therapeutic drug for Alzheimer's disease (donepezil, galanthamine, memantine, rivastigmine, etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, amantadine hydrochloride, bromocriptine mesilate, trihexyphenidyl hydrochloride, selegiline hydrochloride, combination thereof etc.), therapeutic drug for Parkinson's disease associated with dementia (rivastigmine), therapeutic drug for Lewy body dementia (donepezil), therapeutic drug for ALS (riluzole, neurotrophic factor, etc.), therapeutic drug for hyperlipidemia such as cholesterol-lowering drug (statin series (pravastatin sodium, atorvastatin, simvastatin, rosuvastatin, etc.), fibrate (clofibrate etc.), squalene synthase inhibitor), therapeutic drug for abnormal behavior or dementia-related wandering (sedative drug, antianxiety drug, etc.), apoptosis inhibitor, antiobesity drug, antidiabetic drug, therapeutic drug for hypertension, therapeutic drug for hypotension, therapeutic drug for rheumatism (DMARD), anticancer drug, therapeutic drug for hypoparathyroidism (PTH), calcium receptor antagonist, sex hormone or derivative thereof (progesterone, estradiol, estradiol benzoate etc.), neuron differentiation accelerator, neurogeneration promotor, non-steroidal anti-inflammatory drug (meloxicam, tenoxicam, indomethacin, ibuprofen, celecoxib, rofecoxib, aspirin etc.), steroid (dexamethasone, cortisone acetate, etc.), anti-cytokine drug (TNF inhibitor, MAP kinase inhibitor, etc.), antibody medicament, nucleic acid or nucleic acid derivative, aptamer and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present so invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel, and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of 1H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

Elemental analysis value (Anal.) is described as calculated value (Calcd) and actual measured value (Found).

Powder X-RAY diffraction pattern was measured using Cu-Kα characteristic radiation from Rigaku Ultima IV, and characteristic peaks were described.

In Examples, the following abbreviations are used.
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
AIBN: 2,2'-azobis(isobutyronitrile)
CPME: cyclopentyl methyl ether
DME: 1,2-dimethoxyethane
DIPEA: N,N-diisopropylethylamine
DMF: N,N-dimethylformamide
DMSO: dimethyl sulfoxide
EDCI: 1-ethyl-3-(3-dimethylaminopropyl)carbodiimide
HATU: O-(7-azabenzotriazole-1-yl)-N,N,N',N'-tetramethyluronium hexafluorophosphorate
HOBt: 1-hydroxybenzotriazole
NBS: N-bromosuccinimide
NIS: N-iodosuccinimide
Pd(dppf)$Cl_2$: [1,1'-bis(diphenylphosphino)ferrocene]dichloropalladium(II)
SEM-Cl: (2-chloromethoxyethyl)trimethylsilane
TEA: triethylamine
TFA: trifluoroacetic acid
THF: tetrahydrofuran
MecOH: methanol
EtOH: ethanol
WSC HCl: 1-ethyl-3-(3-dimethylaminopropyl)carbodiimide hydrochloride
XANTPHOS: (9,9-dimethyl-9H-xanthene-4,5-diyl)bis(diphenylphosphine)

Example 1a

5-[(2-{4-[5-(difluoromethyl)-1,3,4-oxadiazol-2-yl]pyridin-2-yl}-1H-imidazol-1-yl)methyl]-2-fluorobenzonitrile A) 4-bromo-2-(1H-imidazol-2-yl)pyridine To a mixture of 4-bromopyridine-2-carbaldehyde (5 g) and MecOH (50 mL) were added 40% aqueous glyoxal solution (4.91 mL) and aqueous ammonia (20 mL) at 0° C., and the mixture was stirred at room temperature for 4 hr. The reaction solution was concentrated, and the residue was purified by silica gel column chromatography (MeOH/methylene chloride) to give the title compound (3.5 g).
MS: [M+H]$^+$ 223.9.

B) 4-bromo-2-(1-{[2-(trimethylsilyl)ethoxy]methyl}-1H-imidazol-2-yl)pyridine

To a mixture of 4-bromo-2-(1H-imidazol-2-yl)pyridine (5.0 g) and DMF (30 mL) was gradually added sodium hydride (60% oil 1.35 g) at 0° C., and the mixture was stirred for 30 min. SEM-Cl (5.93 mL) was gradually added to the reaction solution at 0° C., and the mixture was stirred at room temperature for 16 hr. To the reaction solution was added ice water, and the mixture was extracted with ethyl acetate. The organic layer was washed with saturated brine, dried over anhydrous sodium sulfate, and concentrated under reduced pressure to give the title compound as a crude product (6.9 g).

MS: [M+H]$^+$ 353.7.

C) ethyl 2-(1-{[2-(trimethylsilyl)ethoxy]methyl}-1H-imidazol-2-yl)pyridine-4-carboxylate To a mixture of 4-bromo-2-(1-{[2-(trimethylsilyl)ethoxy]methyl}1-H-imidazol-2-yl)pyridine (1.0 g) and EtOH (40 mL) were added TEA (1.6 mL) and Pd(dppf)Cl$_2$ (0.2 g), and the reaction solution was stirred under carbon monoxide (200 psi) atmosphere at 90° C. for 16 hr. The reaction solution was filtered, and the filtrate was concentrated under reduced pressure. The residue was purified by silica gel column chromatography (ethyl acetate/hexane) to give the title compound (0.5 g).

MS: [M+H]$^+$ 348.1.

D) 2-(1-{[2-(trimethylsilyl)ethoxy]methyl}-1H-imidazol-2-yl)pyridine-4-carboxylic Acid To a solution of ethyl 2-(1-{[2-(trimethylsilyl)ethoxy]methyl}-1H-imidazol-2-yl)pyridine-4-carboxylate (400 mg) in THF-water (10 mL, 5:1) was added lithium hydroxide (159 mg) at room temperature. The mixture was stirred for 18 hr, and the reaction solution was concentrated under reduced pressure. To the residue was added water, and the mixture was adjusted to pH 5-6 with 6 N hydrochloric acid at 0° C. The obtained solid was collected by filtration to give the title compound (300 mg).

MS: [M+H]$^+$320.0.

E) 2,2-difluoro-N'-{[2-(1-{[2-(trimethylsilyl)ethoxy]methyl}-1H-imidazol-2-yl)pyridin-4-yl]carbonyl}acetohydrazide To the mixture of 2-(1-{[2-(trimethylsilyl)ethoxy]methyl}-1H-imidazol-2-yl)pyridine-4-carboxylic acid (3.0 g) and DMF (20 mL) were added TEA (3.2 mL), EDCI (2.7 g) and HOBT (1.9 g), and the mixture was stirred at room temperature for 15 min. To the reaction solution was added 2,2-difluoroacetyl hydrazide (1.24 g), and the mixture was stirred for 5 hr. The reaction solution was poured into water, and extracted with ethyl acetate. The organic layer was washed with water and saturated brine, dried over anhydrous magnesium sulfate, and concentrated under reduced pressure to give the title compound (1.4 g).

MS: [M+H]$^+$ 411.6.

F) 4-[5-(difluoromethyl)-1,3,4-oxadiazol-2-yl]-2-(1-{[2-(trimethylsilyl)ethoxy]methyl}-1H-imidazol-2-yl)pyridine To the mixture of 2,2-difluoro-N'-{[2-(1-{[2-(trimethylsilyl)ethoxy]methyl}-1H-imidazol-2-yl)pyridin-4-yl]carbonyl}acetohydrazide (600 mg) and CH$_3$CN (10 mL) were added p-toluenesulfonyl chloride (418 mg) and TEA (0.6 mL) at room temperature. The reaction solution was stirred at 50° C. for 2 hr, and the reaction solution was concentrated under reduced pressure. The residue was diluted with water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (260 mg).

MS: [M+H]$^+$ 394.1.

G) 4-[5-(difluoromethyl)-1,3,4-oxadiazol-2-yl]-2-(1H-imidazol-2-yl)pyridine

To a mixture of 4-[5-(difluoromethyl)-1,3,4-oxadiazol-2-yl]-2-(1-{[2-(trimethylsilyl)ethoxy]methyl}-1H-imidazol-2-yl)pyridine (1.0 g) and dichloromethane (30 mL) was added dropwise 98% boron trifluoride diethyl ether complex (3.2 mL) at 0° C. The reaction solution was stirred for 1 hr, and diluted with aqueous sodium carbonate solution. The reaction solution was extracted with dichloromethane, and the organic layer was washed with water and saturated brine, dried over anhydrous magnesium sulfate, and concentrated under reduced pressure. The obtained solid was washed with pentane to give the title compound (400 mg).

MS: [M+H]$^+$ 264.0.

H) 5-[(2-{4-[5-(difluoromethyl)-1,3,4-oxadiazol-2-yl]pyridin-2-yl}-1H-imidazol-1-yl)methyl]-2-fluorobenzonitrile To a mixture of 5-(bromomethyl)-2-fluorobenzonitrile (172 mg), 4-[5-(difluoromethyl)-1,3,4-oxadiazol-2-yl]-2-(1H-imidazol-2-yl)pyridine (176 mg) and DMF (2.0 ml) was added cesium carbonate (218 mg) at room temperature. The mixture was stirred overnight at room temperature, and concentrated. The residue was purified by silica gel column chromatography (NH, ethyl acetate/hexane) to give the title compound (160 mg).

$^1$H NMR (400 MHz, DMSO-d$_6$) δ 5.84-5.99 (2H, m), 7.13-7.27 (1H, m), 7.41-7.74 (4H, m), 7.80-7.88 (1H, m), 7.92-7.96 (1H, m), 8.61-8.71 (1H, m), 8.80-8.90 (1H, m).

Example 8a

2-{3-[5-(difluoromethyl)-1,3,4-oxadiazol-2-yl]-5-fluorophenyl}-3-[(oxan-4-yl)oxy]pyridine A) 3-(benzyloxy)-2-bromopyridine To a mixture of 2-bromopyridin-3-ol (5 g), potassium carbonate (5.96 g) and DMF (20 ml) was added benzyl bromide (5.41 g) at room temperature. The mixture was stirred at room temperature for 17 hr, and the mixture was poured into water, and extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (6.68 g).

MS: [M+H]$^+$ 264.0.

B) tert-butyl 2-(3-bromo-5-fluorobenzoyl)hydrazine-1-carboxylate

To a mixture of 3-bromo-5-fluorobenzoic acid (5.10 g), tert-butyl hydrazinecarboxylate (3.70 g), 1H-benzotriazol-1-ol monohydrate (5.24 g) and DMF (46 mL) was added WSC HCl (6.59 g) at room temperature. The mixture was stirred at room temperature for 17 hr, and added dropwise to water at room temperature. The obtained solid was collected by filtration to give the title compound (7.67 g).

MS: [M−H]$^−$ 330.8.

C) 3-bromo-5-fluorobenzhydrazide Hydrochloride

To tert-butyl 2-(3-bromo-5-fluorobenzoyl)hydrazine-1-carboxylate (7.67 g) was added 4 M hydrogen chloride CPME solution (100 mL) at 0° C. The mixture was stirred at room temperature for 4 hr. The obtained solid was collected by filtration to give the title compound (6.00 g).
MS: [M+H]$^+$ 233.0.

D) 2-(3-bromo-5-fluorophenyl)-5-(difluoromethyl)-1,3,4-oxadiazole

To a mixture of 3-bromo-5-fluorobenzhydrazide hydrochloride (6.00 g), DIPEA (19.5 mL) and THF (200 mL) was added difluoroacetic anhydride (4.2 mL) at 0° C. The mixture was stirred at room temperature for 3 hr, and 4-methylbenzenesulfonyl chloride (8.50 g) was added thereto at room temperature. The mixture was stirred at room temperature for 17 hr, and the reaction solution was partitioned between ethyl acetate-water. The organic layer was washed with 5% aqueous citric acid solution, saturated aqueous sodium hydrogencarbonate solution and saturated aqueous ammonium chloride solution, dried over anhydrous magnesium sulfate, and concentrated under reduced pressure. The residue was purified by silica gel column chromatography (ethyl acetate/hexane) to give the title compound (4.15 g).
$^1$H NMR (400 MHz, DMSO-d$_6$) δ 7.57 (1H, t, J=51.1 Hz), 7.93 (1H, ddd, J=8.8, 2.4, 1.5 Hz), 7.97 (1H, ddd, J=8.3, 2.4, 2.3 Hz), 8.05 (1H, t, J=1.3 Hz).

E) 2-(difluoromethyl)-5-[3-fluoro-5-(4,4,5,5-tetramethyl-1,3,2-dioxaborolan-2-yl)phenyl]-1,3,4-oxadiazole A mixture of 2-(3-bromo-5-fluorophenyl)-5-(difluoromethyl)-1,3,4-oxadiazole (504 mg), 4,4,4',4',5,5,5',5'-octamethyl-2,2'-bi-1,3,2-dioxaborolane (649 mg), Pd(dppf)Cl$_2$ (63 mg), potassium acetate (817 mg) and DME (4.2 mL) was irradiated with microwave at 120° C. for 45 min. The reaction solution was purified by silica gel column chromatography (ethyl acetate/hexane) to give the title compound (723 mg).
MS: [M+H]$^+$ 341.1.

F) 3-(benzyloxy)-2-{3-[5-(difluoromethyl)-1,3,4-oxadiazol-2-yl]-5-fluorophenyl}pyridine A mixture of 2-(difluoromethyl)-5-[3-fluoro-5-(4,4,5,5-tetramethyl-1,3,2-dioxaborolan-2-yl)phenyl]-1,3,4-oxadiazole (118 mg), 3-(benzyloxy)-2-bromopyridine (94.5 mg), 4-(di-tert-butylphosphino)-N,N-dimethylaniline-dichloropalladium (2:1) (17.8 mg), 2.6 M cesium fluoride aqueous solution (432 μL) and DME (2.16 mL) was irradiated with microwave at 80° C. for 45 min. The mixture was partitioned between ethyl acetate and water, and the organic layer was separated, dried over anhydrous magnesium sulfate, and concentrated under reduced pressure. The residue was purified by silica gel column chromatography (ethyl acetate/hexane) to give the title compound (97.6 mg).
MS: [M+H]$^+$ 398.1.

G) 2-{3-[5-(difluoromethyl)-1,3,4-oxadiazol-2-yl]-5-fluorophenyl}pyridin-3-ol A mixture of 3-(benzyloxy)-2-{3-[5-(difluoromethyl)-1,3,4-oxadiazol-2-yl]-5-fluorophenyl}pyridine (0.474 g), 10% palladium on carbon (0.114 g), EtOH (15 mL) and THF (5 mL) was stirred under normal hydrogen atmosphere at room temperature for 15 hr. The catalyst was removed by filtration, and the filtrate was concentrated under reduced pressure to give the title compound (0.374 g).
MS: [M+H]$^+$ 308.1.

H) 2-{3-[5-(difluoromethyl)-1,3,4-oxadiazol-2-yl]-5-fluorophenyl}-3-[(oxan-4-yl)oxy]pyridine To a mixture of tetrahydro-2H-pyran-4-ol (30.9 mg), DIAD (57 μL), triphenylphosphine (78.3 mg) and THF (3 mL) was added 2-{3-[5-(difluoromethyl)-1,3,4-oxadiazol-2-yl]-5-fluorophenyl}pyridin-3-ol (59.6 mg) at room temperature. The mixture was stirred at room temperature for 17 hr. The reaction solution was supported on silica gel, and purified by silica gel column chromatography (ethyl acetate/hexane) to give the title compound (21.6 mg).
$^1$H NMR (400 MHz, DMSO-d$_6$) δ 1.62-1.72 (2H, m), 1.98-2.07 (2H, m), 3.52 (2H, ddd, J=11.7, 8.4, 3.2 Hz), 3.79 (2H, ddd, J=11.7, 5.9, 3.9 Hz), 4.84 (1H, tt, J=7.8, 3.8 Hz), 7.58 (1H, t, J=51.3 Hz), 7.46 (1H, dd, J=8.6, 4.4 Hz), 7.78 (1H, dd, J=8.6, 1.0 Hz), 7.91 (1H, ddd, J=8.6, 2.4, 1.5 Hz), 8.13 (1H, ddd, J=10.5, 2.4, 1.5 Hz), 8.34 (1H, dd, J=4.5, 1.2 Hz), 8.66 (1H, t, J=1.5 Hz).

Example 19a

(5R)-5-benzyl-4-{4-[5-(difluoromethyl)-1,3,4-oxadiazol-2-yl]pyridin-2-yl}morpholin-3-one

A) (5R)-5-benzyl morpholin-3-one

To a mixture of (2R)-2-amino-3-phenylpropan-1-ol (1.51 g), TEA (1.307 g) and THF (120 mL) was added chloroacetyl chloride (1.39 g) at 0° C. The mixture was stirred at room temperature for 2 hr, and the reaction solution was partitioned between ethyl acetate-water. The organic layer was washed with saturated brine, dried over anhydrous magnesium sulfate, and concentrated under reduced pressure. The residue was dissolved in THF (100 mL), and sodium hydride (0.800 g) was added thereto at 0° C. The mixture was stirred at room temperature for 2 hr, and the reaction solution was added to ice water, and extracted with ethyl acetate. The organic layer was dried over anhydrous magnesium sulfate, and concentrated under reduced pressure. The residue was purified by silica gel column chromatography (ethyl acetate/MeOH) to give the title compound (1.30 g).
MS: [M+H]$^+$ 192.2.

B) methyl 2-[(3R)-3-benzyl-5-oxomorpholin-4-yl]pyridine-4-carboxylate

A mixture of methyl 2-chloroisonicotinate (305 mg), (5R)-5-benzyl morpholin-3-one (374 mg), palladium acetate (24 mg), XANTPHOS (86 mg), cesium carbonate (875 mg) and DME (10 mL) was irradiated with microwave at 100° C. for 3 hr. The reaction solution was partitioned between ethyl acetate-water, and the organic layer was washed with saturated brine, dried over anhydrous magnesium sulfate, and concentrated under reduced pressure. The residue was purified by silica gel column chromatography (ethyl acetate/hexane) to give the title compound (425 mg).
MS: [M+H]$^+$ 327.2.

C) 2-{[(2R)-1-(carboxymethoxy)-3-phenylpropan-2-yl]amino}pyridine-4-carboxylic Acid To a mixture of methyl 2-[(3R)-3-benzyl-5-oxomorpholin-4-yl]pyridine-4-carboxylate (425 mg), THF (4.0 mL) and MeOH (4.0 mL) was added 1 M aqueous sodium hydroxide solution (4.0 mL) at room temperature. The mixture was stirred at room temperature for 15 hr. The reaction solution was diluted with water, neutralized with 1 M hydrochloric acid (4.0 mL), and extracted with ethyl acetate-THF (5:1). The organic layer was separated, and concentrated under reduced pressure. The residue was dried by azeotropy with toluene under reduced pressure to give the title compound (285 mg).
MS: [M+H]$^+$ 331.2.

D) 2-[(3R)-3-benzyl-5-oxomorpholin-4-yl]-N'-(difluoroacetyl)pyridine-4-carbohydrazide To a mixture of 2-{[(2R)-1-(carboxymethoxy)-3-phenylpropan-2-yl]amino}pyridine-4-carboxylic acid (126 mg), HATU (459 mg) and DMF (10 mL) was added DIPEA (167 mg) at room temperature. The mixture was stirred at room temperature for 1 hr, and 2,2-difluoroacetohydrazide (45 mg) was added thereto at room temperature. The mixture was stirred at room temperature for 15 hr, and the reaction solution was partitioned between ethyl acetate-water. The organic layer was washed with saturated brine, dried over anhydrous magnesium sulfate, and concentrated under reduced pressure. The residue was purified by silica gel column chromatography (ethyl acetate/hexane) to give the title compound (156 mg).
MS: [M+H]$^+$ 405.2.

E) (5R)-5-benzyl-4-{4-[5-(difluoromethyl)-1,3,4-oxadiazol-2-yl]pyridin-2-yl}morpholin-3-one To a mixture of 2-[(3R)-3-benzyl-5-oxomorpholin-4-yl]-N'-(difluoroacetyl)pyridine-4-carbohydrazide (289 mg), 4-methylbenzenesulfonyl chloride (199.1 mg) and acetonitrile (14 mL) was added DIPEA (255 mg) at 0° C. The mixture was stirred at room temperature for 3 hr, and the reaction solution was partitioned between ethyl acetate-water. The organic layer was washed with saturated brine, dried over anhydrous magnesium sulfate, and concentrated under reduced pressure. The residue was purified by silica gel column chromatography (ethyl acetate/hexane) to give the title compound (55.3 mg). $^1$H NMR (400 MHz, CDCl$_3$) δ 3.01 (1H, dd, J=13.2, 5.6 Hz), 3.06 (1H, dd, J=13.2, 9.3 Hz), 3.79 (1H, ddd, J=12.2, 2.9, 0.7 Hz), 3.99 (1H, dt, J=12.2, 1.2 Hz), 4.33 (1H, d, J=17.4 Hz), 4.53 (1H, dd, J=17.1, 1.0 Hz), 5.04-5.11 (1H, m), 6.94 (1H, t, J=51.6 Hz), 7.16-7.31 (5H, m), 7.84 (1H, dd, J=4.9, 1.5 Hz), 8.71 (1H, t, J=1.1 Hz), 8.72 (1H, dd, J=5.0, 0.9 Hz).

Example 47a

2-(difluoromethyl)-5-(3-fluoro-5-{5-[(oxan-4-yl)oxy]-1H-pyrazol-1-yl}phenyl)-1,3,4-oxadiazole

A) (3-fluoro-5-iodophenyl)hydrazine Hydrochloride

To a mixture of 3-fluoro-5-iodoaniline (10.00 g) and conc. hydrochloric acid (50 mL) was added a cooled mixture of sodium nitrite (3.49 g) and water (10 mL) at 0° C. The mixture was stirred at 0° C. for 1 hr, and a mixture of tin(II) chloride dihydrate (28.56 g) and conc. hydrochloric acid (15 mL) was added dropwise thereto at 0° C. The mixture was stirred at 0° C. for 1.5 hr, and the mixture was stored in the refrigerator at 10° C. or below for 17 hr while kept stand. The precipitate was collected by filtration, washed with cold water and pentane, and dried to give the title compound (7.5 g). 1H NMR (DMSO-d$_6$, 400 MHz) δ 6.81-6.84 (1H, m), 7.10-7.17 (2H, m), 8.75 (1H, brs), 10.40 (2H, brs).

B) ethyl 1-(3-fluoro-5-iodophenyl)-5-hydroxy-1H-pyrazole-4-carboxylate

To a mixture of (3-fluoro-5-iodophenyl)hydrazine hydrochloride (8.00 g), potassium carbonate (5.26 g) and EtOH (40 mL) was added diethyl (ethoxymethylene)malonate (6.86 mL) at room temperature. The mixture was stirred at 80° C. for 18 hr, and the reaction solution was concentrated under reduced pressure. The obtained residue was dissolved in ethyl acetate, and the solution was acidified with 1 M hydrochloric acid. The organic layer was washed with water and saturated brine, dried over anhydrous sodium sulfate, and concentrated under reduced pressure. The residue was purified by silica gel column chromatography to give the title compound (5.4 g).
MS: [M+H]$^+$ 376.6.

C) 1-(3-fluoro-5-iodophenyl)-1H-pyrazol-5-ol

To a mixture of ethyl 1-(3-fluoro-5-iodophenyl)-5-hydroxy-1H-pyrazole-4-carboxylate (5.40 g) and MeOH (35 mL) was added 10% aqueous sodium hydroxide solution (57 mL) at 0° C. The mixture was stirred at room temperature for 3 hr, and refluxed for 48 hr. The reaction solution was cooled to room temperature, and concentrated under reduced pressure. The residue was diluted with water, and the mixture was neutralized with 1 M hydrochloric acid, and extracted with ethyl acetate. The organic layer was separated, washed with water and saturated brine, dried over anhydrous sodium sulfate, and concentrated under reduced pressure. The residue was purified by silica gel column chromatography (dichloromethane/MeOH) to give the title compound (1.50 g).
MS: [M+H]$^+$ 305.0.

D) 1-(3-fluoro-5-iodophenyl)-5-[(oxan-4-yl)oxy]-1H-pyrazole

To a mixture of triphenylphosphine (0.65 g) and THF (5 mL) was added DIAD (0.48 mL) at 0° C., the mixture was stirred at 0° C. for 20 min, and 1-(3-fluoro-5-iodophenyl)-1H-pyrazol-5-ol (0.50 g) and tetrahydro-2H-pyran-4-ol (0.25 g) were added thereto under ice-cooling. The mixture was stirred at room temperature for 24 hr, the reaction solution was concentrated under reduced pressure, and the residue was purified by silica gel column chromatography (ethyl acetate/hexane) to give the title compound (0.28 g).
MS: [M+H]$^+$ 388.8.

E) tert-butyl 2-(3-fluoro-5-{5-[(oxan-4-yl)oxy]-1H-pyrazol-1-yl}benzoyl)hydrazine-1-carboxylate To a mixture of 1-(3-fluoro-5-iodophenyl)-5-[(oxan-4-yl)oxy]-1H-pyrazole (0.27 g), tert-butyl carbazate (0.14 g), N-cyclohexyl-N-methylcyclohexanamine (0.20 g) and CPME (10 mL) were added Pd$_2$(dba)$_3$ (0.03 g) and XANTPHOS (0.04 g) under argon atmosphere. The mixture was stirred under carbon monoxide atmosphere at 80° C. for 16 hr. The reaction solution was concentrated under reduced pressure, and the residue was purified by silica gel column chromatography (ethyl acetate/hexane) to give the title compound (0.23 g).

MS: [M+H]$^+$ 421.2.

F) 3-fluoro-5-{5-[(oxan-4-yl)oxy]-1H-pyrazol-1-yl}benzhydrazide

To a mixture of tert-butyl 2-(3-fluoro-5-{5-[(oxan-4-yl)oxy]-1H-pyrazol-1-yl}benzoyl)hydrazine-1-carboxylate (0.32 g) and dichloromethane (5 mL) was added trifluoroacetic acid (0.58 mL) under ice-cooling. The mixture was stirred at room temperature for 4 hr, and the reaction solution was concentrated. The obtained residue was neutralized with saturated aqueous sodium hydrogencarbonate solution, and extracted with ethyl acetate. The organic layer was separated, washed with water and saturated brine, dried over anhydrous sodium sulfate, and concentrated under reduced pressure to give the title compound (0.22 g).

MS: [M+H]$^+$ 321.0.

G) 2-(difluoromethyl)-5-(3-fluoro-5-{5-[(oxan-4-yl)oxy]-1H-pyrazol-1-yl}phenyl)-1,3,4-oxadiazole To a mixture of 3-fluoro-5-{5-[(oxan-4-yl)oxy]-1H-pyrazol-1-yl}benzhydrazide (0.23 g) and THF (5 mL) were added DIPEA (0.45 mL) and difluoroacetic anhydride (2.33 mL) under ice-cooling. The mixture was stirred at room temperature for 4 hr, the reaction solution was concentrated under reduced pressure, and the residue was purified by silica gel column chromatography (ethyl acetate/hexane) to give the title compound (0.12 g).

1H NMR (400 MHz, DMSO) δ 1.75-1.77 (2H, m), 1.98-2.15 (2H, m), 3.53-3.58 (2H, m), 3.83-3.84 (2H, m), 4.65-4.75 (1H, s), 6.08 (1H, s), 7.45-7.70 (2H, m), 7.80 (1H, d, J=8.1 Hz), 7.91 (1H, d, J=10.3 Hz), 8.40 (1H, s).

Example 85a

4-[5-(difluoromethyl)-1,3,4-oxadiazol-2-yl]-2-{1-[(3-fluorophenyl)methyl]-1H-1,2,4-triazol-5-yl}pyridine A) 1-[(3-fluorophenyl)methyl]-1H-1,2,4-triazole To a mixture of 1H-1,2,4-triazole (0.707 g), 1-(bromomethyl)-3-fluorobenzene (2.033 g) and DMF (10 mL) was added potassium carbonate (2.074 g) at room temperature. The mixture was stirred under nitrogen atmosphere at room temperature for 17 hr. The reaction solution was partitioned between ethyl acetate-water, and the organic layer was washed with saturated brine, dried over anhydrous magnesium sulfate, and concentrated under reduced pressure. The residue was purified by silica gel column chromatography (ethyl acetate/hexane) to give the title compound (1.344 g).

MS: [M+H]$^+$ 178.1.

B) 2-{1-[(3-fluorophenyl)methyl]-1H-1,2,4-triazol-5-yl}pyridine-4-carboxylic Acid To a mixture of 1-[(3-fluorophenyl)methyl]-1H-1,2,4-triazole (0.871 g), copper(I) iodide (0.183 g), N,N'-dimethylethane-1,2-diamine (100 μL), lithium tert-butoxide (1.173 g) and diglyme (5 mL) was added methyl 2-bromoisonicotinate (2.87 g), and the mixture was stirred in a sealed tube at 130° C. for 24 hr. The reaction solution was diluted with water, and washed with ethyl acetate. The aqueous layer was acidified with 1 M hydrochloric acid (15 mL), and extracted with ethyl acetate, and the organic layer was concentrated under reduced pressure. The residue was purified by HPLC (YMCTriartC18, mobile phase: water/acetonitrile (containing ammonium bicarbonate)). The obtained fraction was concentrated under reduced pressure, to the residue was added 0.1 M hydrochloric acid, and the mixture was extracted with ethyl acetate. The organic layer was separated, dried over anhydrous magnesium sulfate, and concentrated under reduced pressure to give the title compound (0.375 g).

MS: [M+H]$^+$ 299.1.

C) N'-(difluoroacetyl)-2-{1-[(3-fluorophenyl)methyl]-1H-1,2,4-triazol-5-yl}pyridine-4-carbohydrazide To a mixture of 2-{1-[(3-fluorophenyl)methyl]-1H-1,2,4-triazol-5-yl}pyridine-4-carboxylic acid (99.3 mg), 1H-benzotriazol-1-ol monohydrate (78.5 mg), WSC HCl (100.6 mg) and DMF (2.5 mL) was added 2,2-difluoroacetohydrazide (48.1 mg) at room temperature. The mixture was stirred at room temperature for 2.5 hr, and the reaction solution was partitioned between ethyl acetate-water. The organic layer was washed with saturated brine, dried over anhydrous magnesium sulfate, and concentrated under reduced pressure. The residue was purified by silica gel column chromatography (ethyl acetate/hexane) to give the title compound (128.7 mg).

MS: [M+H]$^+$ 391.1.

D) 4-[5-(difluoromethyl)-1,3,4-oxadiazol-2-yl]-2-{1-[(3-fluorophenyl)methyl]-1H-1,2,4-triazol-5-yl}pyridine To a mixture of N'-(difluoroacetyl)-2-{1-[(3-fluorophenyl)methyl]-1H-1,2,4-triazol-5-yl}pyridine-4-carbohydrazide (124.8 mg), 4-methylbenzenesulfonyl chloride (117.9 mg) and THF (5 mL) was added DIPEA (160 μL) at room temperature. The mixture was stirred at room temperature for 3.5 days, the reaction solution was concentrated, and the obtained residue was purified by silica gel column chromatography (ethyl acetate/hexane) to give the title compound (101.9 mg).

1H NMR (400 MHz, DMSO-d$_6$) δ 6.10 (2H, s), 7.08-7.14 (3H, m), 7.34-7.40 (1H, m), 7.62 (1H, t, J=51.3 Hz), 8.13 (1H, dd, J=5.1, 1.7 Hz), 8.25 (1H, s), 8.68 (1H, dd, J=1.7, 1.0 Hz), 9.01 (1H, dd, J=5.2, 0.7 Hz).

Example 87a

4-[5-(difluoromethyl)-1,3,4-oxadiazol-2-yl]-2-{5-[(3-fluorophenyl)methyl]-1H-pyrazol-1-yl}pyridine A) methyl 2-[1-(tert-butoxycarbonyl)hydrazinyl]pyridine-4-carboxylate A mixture of methyl 2-bromoisonicotinate (5.03 g), tert-butyl hydrazinecarboxylate (3.61 g), Pd(dppf)Cl$_2$ (0.845 g), cesium carbonate (9.24 g) and toluene (85 mL) was stirred under nitrogen atmosphere at 100° C. for 2 hr. The reaction solution was filtered, and the filtrate was concentrated under reduced pressure. The residue was purified by silica gel column chromatography (ethyl acetate/hexane) to give the title compound (4.13 g).

MS: [M+H-Boc]$^+$168.1.

B) methyl 2-hydrazinylpyridine-4-carboxylate trihydrochloride

To a mixture of methyl 2-[1-(tert-butoxycarbonyl)hydrazinyl]pyridine-4-carboxylate (4.13 g) and MeOH (5 mL) was added 4 M hydrogen chloride CPME solution (20 mL) at room temperature. The mixture was stirred at room temperature for 5 hr. The reaction solution was concentrated under reduced pressure to give the title compound (4.14 g).
MS: [M+H]$^+$ 168.2.

C) 1-(3-fluorophenyl)-4-hydroxybut-3-en-2-one

To a mixture of 60% sodium hydride (0.672 g) and Et2O (65 mL) was added 1-(3-fluorophenyl)propan-2-one (2.498 g) at 0° C. The mixture was stirred under nitrogen atmosphere at 0° C. for 30 min. To the reaction mixture was added ethyl formate (2.0 mL) at 0° C., and the mixture was stirred under nitrogen atmosphere at room temperature for 15 hr. The mixture was added to ice water, and the organic layer was separated, and extracted with water. The aqueous layers were combined, acidified with 2 M hydrochloric acid, and extracted with diethyl ether. The organic layer was washed with saturated brine, dried over anhydrous sodium sulfate, and concentrated under reduced pressure to give the title compound as a crude product (1.827 g)
MS: [M–H]$^-$ 179.0.

D) (3E)-4-(diethylamino)-1-(3-fluorophenyl)but-3-en-2-one

To a mixture of the crude product 1-(3-fluorophenyl)-4-hydroxybut-3-en-2-one (1.823 g) and toluene (20 mL) was added diethylamine (1.0 mL) at room temperature. The mixture was stirred at room temperature for 1.5 days. The reaction solution was concentrated under reduced pressure to give the title compound as a crude product (2.387 g).
MS: [M+H]$^+$ 236.2.

E) methyl 2-{5-[(3-fluorophenyl)methyl]-1H-pyrazol-1-yl}pyridine-4-carboxylate A mixture of methyl 2-hydrazinylpyridine-4-carboxylate trihydrochloride (1.495 g), the crude product (3E)-4-(diethylamino)-1-(3-fluorophenyl)but-3-en-2-one (2.387 g), AcOH (4.0 mL) and MeOH (20 mL) was stirred at 70° C. for 3 hr. The reaction solution was concentrated, and the obtained residue was partitioned between ethyl acetate-saturated aqueous sodium hydrogencarbonate solution. The organic layer was washed with saturated brine, dried over anhydrous magnesium sulfate, and concentrated under reduced pressure. The residue was purified by silica gel column chromatography (ethyl acetate/hexane), followed by HPLC (YMCTriantC18, mobile phase: water/acetonitrile (containing ammonium bicarbonate)). The obtained fraction was concentrated under reduced pressure to give the title compound (0.583 g).
MS: [M+H]$^+$ 312.2.

F) 2-{5-[(3-fluorophenyl)methyl]-1H-pyrazol-1-yl}pyridine-4-carboxylic Acid

To a mixture of methyl 2-{5-[(3-fluorophenyl)methyl]-1H-pyrazol-1-yl}pyridine-4-carboxylate (0.583 g), THF (8 mL) and MeOH (8 mL) was added 1 M aqueous sodium hydroxide solution (8.0 mL) at room temperature. The mixture was stirred at room temperature for 3 hr. The reaction solution was diluted with water, and washed with toluene. The aqueous layer was separated, neutralized with 1 M hydrochloric acid (8.0 mL), and extracted with ethyl acetate. The organic layer was washed with saturated brine, dried over anhydrous magnesium sulfate, and concentrated under reduced pressure to give the title compound (0.551 g).
MS: [M+H]$^+$ 298.1.

G) N'-(difluoroacetyl)-2-{5-[(3-fluorophenyl)methyl]-1H-pyrazol-1-yl}pyridine-4-carbohydrazide To a mixture of 2-{5-[(3-fluorophenyl)methyl]-1H-pyrazol-1-yl}pyridine-4-carboxylic acid (232 mg), 1H-benzotriazol-1-ol monohydrate (182 mg) and DMF (5 mL) were added WSC HCl (222 mg) and 2,2-difluoroacetohydrazide (116 mg) at room temperature. The mixture was stirred at room temperature for 17 hr, and the reaction solution was partitioned between ethyl acetate-water. The organic layer was washed with water and saturated brine, dried over anhydrous magnesium sulfate, and concentrated under reduced pressure. The residue was purified by silica gel column chromatography (ethyl acetate/hexane), and the obtained solid was crystallized from ethyl acetate/n-heptane to give the title compound (295 mg).
MS: [M+H]$^+$ 390.1.

H) 4-[5-(difluoromethyl)-1,3,4-oxadiazol-2-yl]-2-{5-[(3-fluorophenyl)methyl]-1H-pyrazol-1-yl}pyridine To a mixture of N'-(difluoroacetyl)-2-{5-[(3-fluorophenyl)methyl]-1H-pyrazol-1-yl}pyridine-4-carbohydrazide (66.3 mg), 4-methylbenzenesulfonyl chloride (65.2 mg) and THF (5 mL) was added DIPEA (89 μL) at room temperature. The mixture was stirred at room temperature for 17 hr, and the residue was purified by silica gel column chromatography (ethyl acetate/hexane) to give the title compound (48.1 mg). $^1$H NMR (400 MHz, DMSO-d$_6$) δ 4.61 (2H, s), 6.31 (1H, s), 7.01 (1H, t, J=8.3 Hz), 7.07 (2H, d, J=8.1 Hz), 7.31 (1H, q, J=7.3 Hz), 7.60 (1H, t, J=51.2 Hz), 7.78 (1H, s), 7.92 (1H, d, J=5.1 Hz), 8.39 (1H, s), 8.73 (1H, d, J=4.9 Hz).

Example 88a

4'-[(4,4-difluorocyclohexyl)oxy]-4-[5-(difluoromethyl)-1,3,4-oxadiazol-2-yl]-1'-methyl[2,3'-bipyridine]-2'(1'H)-one

A) tert-butyl 2-(2-bromopyridine-4-carbonyl)hydrazine-1-carboxylate

To a mixture of 2-bromopyridine-4-carboxylic acid (5.0 g) and DMF (20 mL) were added WSC (7.118 g), 1H-benzotriazol-1-ol (5.02 g) and TEA (11.85 mL). The mixture was stirred at room temperature for 10 min, to the mixture was added tert-butyl hydrazinecarboxylate (3.92 g), and the mixture was stirred at room temperature for 17 hr. The mixture was added to ice water, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (5.3 g).

1H NMR (DMSO-d$_6$, 400 MHz) δ 1.43 (9H, s), 7.80 (1H, d, J=4.3 Hz), 7.98 (1H, s), 8.58 (1H, d, J=5.0 Hz), 9.12 (1H, brs), 10.59 (1H, brs).

B) 2-bromopyridine-4-carbohydrazide Trifluoroacetate

To a mixture of tert-butyl 2-(2-bromopyridine-4-carbonyl)hydrazine-1-carboxylate (6.0 g) and dichloromethane (100 mL) was added trifluoroacetic acid (14.5 mL) under ice-cooling. The mixture was stirred at room temperature for 2 hr, and the reaction solution was concentrated under reduced pressure to give the title compound (3.6 g).
MS: [M+H]$^+$ 215.8.

C) 2-bromo-4-[5-(difluoromethyl)-1,3,4-oxadiazol-2-yl]pyridine

To a mixture of 2-bromopyridine-4-carbohydrazide monotrifluoroacetate (2.5 g) and THF (20 mL) was added DIPEA (3.3 mL). The mixture was stirred at room temperature for 10 min, difluoroacetic anhydride (3.02 g) was added thereto, and the mixture was stirred at room temperature for 2 hr. To the mixture was added ice water, and the mixture was extracted with ethyl acetate. The organic layer was separated, washed with saturated brine, dried over anhydrous sodium sulfate, and concentrated under reduced pressure to give 2-bromo-N'-(difluoroacetyl)pyridine-4-carbohydrazide (1.5 g) as a crude product.
To a mixture of the crude product 2-bromo-N'-(difluoroacetyl)pyridine-4-carbohydrazide (1.5 g) and acetonitrile (30 mL) were added TsCl (1.46 g) and TEA (1.8 mL). The mixture was stirred at 50° C. for 2 hr, and the reaction solution was concentrated. The obtained residue was partitioned between ethyl acetate-water, and the organic layer was washed with saturated brine, dried over anhydrous sodium sulfate, and concentrated under reduced pressure. The residue was purified by silica gel column chromatography (ethyl acetate/hexane) to give the title compound (400 mg).
MS: [M+H]$^+$ 275.8.

D) 4-(benzyloxy)-3-iodo-1-methylpyridin-2(1H)-one

To a mixture of 4-(benzyloxy)-1-methylpyridin-2(1H)-one (0.923 g) and acetonitrile (85 mL) was added N-iodosuccinimide (1.745 g) at room temperature. The mixture was stirred at room temperature for 2.5 days, the reaction solution was concentrated, and the residue was purified by silica gel column chromatography (ethyl acetate/hexane) to give the title compound (1.46 g).
MS: [M+H]$^+$ 342.0.

E) 4'-(benzyloxy)-4-[5-(difluoromethyl)-1,3,4-oxadiazol-2-yl]-1'-methyl[2,3'-bipyridine]-2'(1'H)-one A mixture of 2-bromo-4-[5-(difluoromethyl)-1,3,4-oxadiazol-2-yl]pyridine (400 mg) and toluene (10 mL) was degassed, the atmosphere was replaced with argon atmosphere, and hexamethylditin (0.31 mL) and Pd(PPh$_3$)$_4$ (134 mg) was added thereto at room temperature. The mixture was stirred under argon atmosphere at 110° C. for 16 hr. The mixture was cooled to room temperature, and filtered through Celite, and the filtrate was concentrated under reduced pressure to give 4-[5-(difluoromethyl)-1,3,4-oxadiazol-2-yl]-2-(trimethylstannyl)pyridine (507 mg) as a crude product.

A mixture of 4-(benzyloxy)-3-iodo-1-methylpyridin-2(1H)-one (400 mg) and toluene (10 mL) was degassed, the atmosphere was replaced with argon atmosphere, and the crude product 4-[5-(difluoromethyl)-1,3,4-oxadiazol-2-yl]-2-(trimethylstannyl)pyridine (507 mg), Pd(PPh$_3$)$_4$ (108 mg) and copper(I) iodide (45 mg) were added thereto at room temperature. The mixture was stirred under argon atmosphere at 110° C. for 16 hr, cooled to room temperature, and filtered through Celite, and the filtrate was concentrated under reduced pressure. The residue was purified by silica gel column chromatography (dichloromethane/MeOH) to give the title compound (100 mg).
MS: [M+H]$^+$ 411.0.

F) 4-[5-(difluoromethyl)-1,3,4-oxadiazol-2-yl]-4'-hydroxy-1'-methyl[2,3'-bipyridine]-2'(1'H)-one A mixture of 4'-(benzyloxy)-4-[5-(difluoromethyl)-1,3,4-oxadiazol-2-yl]-1'-methyl[2,3'-bipyridine]-2'(1'H)-one (500 mg), 10% palladium on carbon (129 mg) and EtOH (20 mL) was stirred under normal hydrogen atmosphere at room temperature for 2 hr. The catalyst was removed by filtration, and the filtrate was concentrated under reduced pressure to give the title compound (350 mg).
MS: [M+H]$^+$ 321.0.

G) 4'-[(4,4-difluorocyclohexyl)oxy]-4-[5-(difluoromethyl)-1,3,4-oxadiazol-2-yl]-1'-methyl[2,3'-bipyridine]-2'(1'H)-one To a mixture of 4,4-difluorocyclohexanol (200 mg) and dichloromethane (15 mL) were added TEA (0.49 mL) and MsCl (0.17 mL) at 0° C. The mixture was stirred at room temperature for 3 hr, and to the mixture ice was added water. The organic layer was separated, washed with saturated aqueous sodium hydrogencarbonate solution and saturated brine, dried over anhydrous sodium sulfate, and concentrated under reduced pressure to give 4,4-difluorocyclohexyl methanesulfonate (200 mg) as a crude product.
To a mixture of 4-[5-(difluoromethyl)-1,3,4-oxadiazol-2-yl]-4'-hydroxy-1'-methyl[2,3'-bipyridine]-2'(1'H)-one (64 mg) and DMF (1 mL) were added potassium carbonate (54.1 mg) and the crude product 4,4-difluorocyclohexyl methanesulfonate (75.48 mg). The mixture was stirred at room temperature for 4 hr, and then at 80° C. for 17 hr. To the mixture was added water at room temperature, and the mixture was extracted with ethyl acetate. The organic layer was separated, washed with saturated brine, dried over anhydrous sodium sulfate, and concentrated under reduced pressure. The residue was purified by silica gel column chromatography (dichloromethane/MeOH) to give the title compound (28.6 mg).
$^1$H NMR (400 MHz, DMSO) δ 1.71-1.99 (8H, m), 3.46 (3H, s), 4.80-4.81 (1H, m), 6.50 (1H, d, J=7.8 Hz), 7.57 (1H, t, J=51.2 Hz), 7.87-7.89 (2H, m), 7.95 (1H, s), 8.81 (1H, d, J=5.2 Hz).

Example 90a

4-{4-[5-(difluoromethyl)-1,3,4-oxadiazol-2-yl]pyridin-2-yl}-5-[(3-fluorophenyl)methyl]pyrimidine

A) tert-butyl N-[(2-bromopyridine-4-carbonyl)amino]carbamate

To a solution of 2-bromopyridine-4-carboxylic acid (5 g) in methylene chloride (70 mL) were added tert-butyl carbazate (3.6 g), propylphosphonic anhydride (23.6 g) and DIPEA (9.60 g) at room temperature, and the mixture was stirred for 20 hr. The reaction solution was concentrated, and the residue was partitioned between ethyl acetate and water, and extracted with ethyl acetate. The organic layer was separated, washed with water and saturated brine, dried over anhydrous sodium sulfate, and concentrated under reduced pressure to give the title compound (7.45 g).

MS: $[M+H]^+$ 315.9.

B) 2-bromopyridine-4-carbohydrazide Hydrochloride tert-Butyl N-[(2-bromopyridine-4-carbonyl)amino]carbamate (7.45 g) and hydrochloric acid-MeOH (40 mL) were stirred at room temperature for 3 hr. The reaction solution was concentrated to give the title compound (5.9 g) as a white solid.

MS: $[M+H]^+$ 218.0.

C) 2-(2-bromopyridin-4-yl)-5-(difluoromethyl)-1,3,4-oxadiazole

To a solution of 2-bromopyridine-4-carbohydrazide hydrochloride (5.9 g) in THF (80 mL) were added DIPEA (15.1 g) and difluoroacetic anhydride (6.10 g) at 0° C. The reaction solution was stirred at room temperature for 4 hr. 4-Methylbenzenesulfonyl chloride (8.91 g) was added thereto, and the reaction solution was stirred at 50° C. for 6 hr. The reaction solution was concentrated, and the residue was dissolved in ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (petroleum ether/ethyl acetate) to give the title compound (3.62 g).

MS: $[M+H]^+$ 277.9.

D) [4-[5-(difluoromethyl)-1,3,4-oxadiazol-2-yl]-2-pyridyl]-trimethyl-stannane A solution of 2-(2-bromopyridin-4-yl)-5-(difluoromethyl)-1,3,4-oxadiazole (0.4 g), hexamethylditin (950 mg) and tetrakis(triphenylphosphine)palladium(0) (83.7 mg) in toluene (15 mL) was stirred under nitrogen atmosphere at 100° C. 20 hr. The reaction solution was concentrated to give the title compound (520 mg).

MS: $[M+H]^+$ 361.9.

E) 4-chloro-5-[(3-fluorophenyl)methyl]pyrimidine

To a mixture of 5-bromo-4-chloro-pyrimidine (300 mg), 2-[(3-fluorophenyl)methyl]-4,4,5,5-tetramethyl-1,3,2-dioxaborolane (785 mg), dioxane (10 mL) and water (0.5 mL) were added Pd(dppf)Cl$_2$ (113 mg) and potassium carbonate (472 mg) at room temperature. The mixture was stirred under nitrogen atmosphere at 85° C. for 12 hr. The reaction solution was filtered through Celite, and the filtrate was concentrated. The residue was purified by preparative TLC (petroleum ether/ethyl acetate=3/1) to give the title compound (140 mg).

MS: $[M+H]^+$ 223.6.

F) 4-{4-[5-(difluoromethyl)-1,3,4-oxadiazol-2-yl]pyridin-2-yl}-5-[(3-fluorophenyl)methyl]pyrimidine To a mixture of 4-chloro-5-[(3-fluorophenyl)methyl]pyrimidine (140 mg), [4-[5-(difluoromethyl)-1,3,4-oxadiazol-2-yl]-2-pyridyl]-2-pyridyl]-trimethyl-stannane (340 mg) and toluene (5 mL) were added tetrakis(triphenylphosphine)palladium(0) (72.7 mg) and copper iodide (24.0 mg). The reaction solution was stirred under nitrogen atmosphere at 100° C. for 12 hr. The reaction solution was filtered through Celite, and the filtrate was concentrated. The residue was purified by silica gel column chromatography (petroleum ether/ethyl acetate, then dichloromethane/MeOH), followed by HPLC (column: Phenomenex Synergi C18, mobile phase: water/acetonitrile (containing 0.225% formic acid)) to give the title compound (26 mg).

1H NMR (400 MHz, CDCl$_3$) δ 4.58 (2H, s), 6.82-7.11 (4H, m), 7.20-7.22 (1H, m), 8.08-8.09 (1H, m), 8.72 (1H, s), 8.78 (1H, s), 8.93-8.95 (1H, m), 9.28 (1H, s)

Example 91a

4-[5-(difluoromethyl)-1,3,4-oxadiazol-2-yl]-1'-methyl-4'-[(oxan-4-yl)oxy][2,3'-bipyridine]-2'(1'H)-one

A) 4-(benzyloxy)-1-methylpyridin-2(1H)-one

To a mixture of 4-(benzyloxy)pyridin-2(1H)-one (6.22 g), iodomethane (3.9 mL) and DMF (40 mL) was added potassium carbonate (8.54 g) at room temperature. The mixture was stirred at 50° C. for 17 hr. The reaction mixture was poured into water at room temperature, and the obtained suspension was stirred at room temperature for 1 hr. The precipitate was collected by filtration, washed with water, and dried to give the title compound (6.43 g).

MS: $[M+H]^+$ 216.1.

B) 4-hydroxy-1-methylpyridin-2(1H)-one

A mixture of 4-(benzyloxy)-1-methylpyridin-2(1H)-one (5.28 g), 10% palladium on carbon (5.27 g) and EtOH (100 mL) was stirred under normal hydrogen atmosphere at room temperature for 17 hr. The catalyst was removed by filtration, and the filtrate was concentrated under reduced pressure to give the title compound (2.92 g).

MS: $[M+H]^+$ 126.1.

C) 1-methyl-4-[(oxan-4-yl)oxy]pyridin-2(1H)-one

To a mixture of 4-hydroxy-1-methylpyridin-2(1H)-one (1.442 g) and THF (100 mL) were added tetrahydro-2H-pyran-4-ol (1.766 g), diethyl azodicarboxylate 40% toluene solution (10.5 mL) and triphenylphosphine (6.004 g) at room temperature. The mixture was stirred at room temperature for 6 hr. The reaction solution was concentrated under reduced pressure, and the residue was purified by silica gel column chromatography (ethyl acetate/MeOH) to give the title compound (1.828 g).

MS: $[M+H]^+$ 210.2.

D) 3-iodo-1-methyl-4-[(oxan-4-yl)oxy]pyridin-2(1H)-one

To a mixture of 1-methyl-4-[(oxan-4-yl)oxy]pyridin-2(1H)-one (1.822 g) and acetonitrile (50 mL) was added NIS (2.365 g) at room temperature. The mixture was stirred at room temperature for 15 hr. The reaction solution was supported on silica gel, and purified by silica gel column chromatography (ethyl acetate/MeOH), and the obtained solid was recrystallized from ethyl acetate/MeOH/diisopropyl ether to give the title compound (1.777 g).

MS: $[M+H]^+$ 336.0.

E) methyl 2-(trimethylstannyl)pyridine-4-carboxylate

A mixture of methyl 2-bromoisonicotinate (660 mg), hexamethylditin (685 μL), tetrakis(triphenylphosphine)palladium(0) (175 mg) and toluene (4.0 mL) was irradiated with microwave at 140° C. for 20 min. The reaction solution was purified by silica gel column chromatography (NH, ethyl acetate/hexane) to give the title compound as a crude product (927 mg).

MS: [M+H]$^+$ 302.0.

F) methyl 1'-methyl-4'-[(oxan-4-yl)oxy]-2'-oxo-1',2'-dihydro[2,3'-bipyridine]-4-carboxylate A mixture of the crude product methyl 2-(trimethylstannyl)pyridine-4-carboxylate (927 mg), 3-iodo-1-methyl-4-[(oxan-4-yl)oxy]pyridin-2(1H)-one (551 mg), 4-(di-tert-butylphosphino)-N,N-dimethylaniline-dichloropalladium (2:1) (110 mg), cesium fluoride (751 mg) and DME (4.5 mL) was irradiated with microwave at 100° C. for 1 hr. The reaction solution was filtered, to the filtrate were added 4-(di-tert-butylphosphino)-N,N-dimethylaniline-dichloropalladium (2:1) (112 mg), cesium fluoride (755 mg) and 1,2-dimethoxyethane (4.5 mL), and the mixture was irradiated with microwave at 100° C. for 1.5 hr. The reaction solution was filtered, and the filtrate was supported on silica gel (NH), and purified by silica gel column chromatography (NH, ethyl acetate/MeOH) to give the title compound (305 mg).

MS: [M+H]$^+$ 345.1.

G) 1'-methyl-4'-[(oxan-4-yl)oxy]-2'-oxo-1',2'-dihydro[2,3'-bipyridine]-4-carbohydrazide A mixture of methyl 1'-methyl-4'-[(oxan-4-yl)oxy]-2'-oxo-1',2'-dihydro[2,3'-bipyridine]-4-carboxylate (305 mg), hydrazine monohydrate (650 μL) and MeOH (3 mL) was stirred at 60° C. for 30 min. The reaction solution was concentrated under reduced pressure to give the title compound (292 mg).

MS: [M+H]$^+$ 345.2.

H) N'-(difluoroacetyl)-1'-methyl-4'-[(oxan-4-yl)oxy]-2'-oxo-1',2'-dihydro[2,3'-bipyridine]-4-carbohydrazide To a mixture of 1'-methyl-4'-[(oxan-4-yl)oxy]-2'-oxo-1',2'-dihydro[2,3'-bipyridine]-4-carbohydrazide (292 mg) and THF (3 mL) were added difluoroacetic anhydride (120 μL) and DIPEA (310 μL) at 0° C. The mixture was stirred at room temperature for 15 min. The reaction solution was concentrated under reduced pressure, and the residue was purified by HPLC (YMCTriartC18, mobile phase: water/acetonitrile (containing ammonium bicarbonate)). The obtained fraction was concentrated under reduced pressure, and freeze-dried to give the title compound (167 mg).

MS: [M+H]$^+$ 423.2.

I) 4-[5-(difluoromethyl)-1,3,4-oxadiazol-2-yl]-1'-methyl-4'-[(oxan-4-yl)oxy][2,3'-bipyridine]-2'(1'H)-one To a mixture of N'-(difluoroacetyl)-1'-methyl-4'-[(oxan-4-yl)oxy]-2'-oxo-1',2'-dihydro[2,3'-bipyridine]-4-carbohydrazide (42.1 mg), 4-methylbenzenesulfonyl chloride (151 mg) and THF (5 mL) was added DIPEA (158 mg) at room temperature. The mixture was stirred at room temperature for 17 hr. The mixture was concentrated under reduced pressure, and the residue was purified by HPLC (YMCTriantC18, mobile phase: water/acetonitrile (containing ammonium bicarbonate)). The obtained fraction was freeze-dried to give the title compound (20.1 mg).

$^1$H NMR (400 MHz, CDCl$_3$) δ 1.69 (2H, dtd, J=13.2, 6.4, 3.9 Hz), 1.87-1.97 (2H, m), 3.50 (1H, dd, J=6.4, 3.7 Hz), 3.53 (1H, dd, J=6.5, 4.0 Hz), 3.58 (3H, s), 3.67 (2H, ddd, J=11.6, 8.0, 3.4 Hz), 4.58 (1H, tt, J=6.7, 3.4 Hz), 6.13 (1H, d, J=7.6 Hz), 6.93 (1H, t, J=51.7 Hz), 7.39 (1H, d, J=7.6 Hz), 7.89 (1H, dd, J=5.3, 1.5 Hz), 8.12 (1H, dd, J=1.5, 1.0 Hz), 8.93 (1H, dd, J=5.1, 0.5 Hz).

The compounds of Examples are shown in the following tables. MS in the tables means actual measured value. The compounds of Example 2a to Example 7a, Example 9a to Example 18a, Example 20a to Example 46a, Example 49a, Example 53a to Example 68a, Example 70a to Example 84a, Example 86a, Example 89a and Example 92a to Example 95a in the following Table 1 were produced according to the methods described in the above-mentioned Examples, or methods analogous thereto.

TABLE 1

| Example | IUPAC name | Structure | MS |
|---|---|---|---|
| 1a | 5-[(2-{4-[5-(difluoromethyl)-1,3,4-oxadiazol-2-yl]pyridin-2-yl}-1H-imidazol-1-yl)methyl]-2-fluorobenzonitrile | | 397.1 |
| 2a | 2-[3-(5-cyclopropyl-1H-pyrazol-1-yl)phenyl]-5-(difluoromethyl)-1,3,4-oxadiazole | 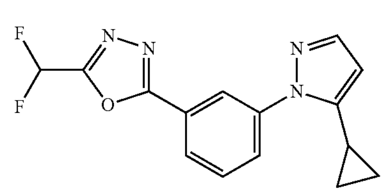 [SMILES: FC(F)c1nnc(-c2cccc(-n3nccc3C3CC3)c2)o1] | 303.1 |

TABLE 1-continued

| Example | IUPAC name | Structure | MS |
|---|---|---|---|
| 3a | 4-[5-(difluoromethyl)-1,3,4-oxadiazol-2-yl]-2-{1-[(pyridin-2-yl)methyl]-1H-imidazol-2-yl}pyridine | 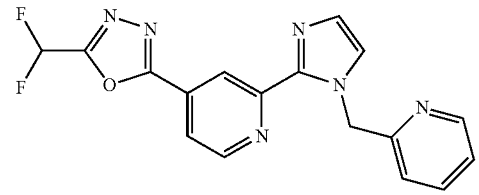 [SMILES: FC(F)c1nnc(-c2ccnc(-c3nccn3Cc3ccccn3)c2)o1] | 355.2 |
| 4a | 2-[3-(1-benzyl-1H-imidazol-2-yl)-5-fluorophenyl]-5-(difluoromethyl)-1,3,4-oxadiazole | 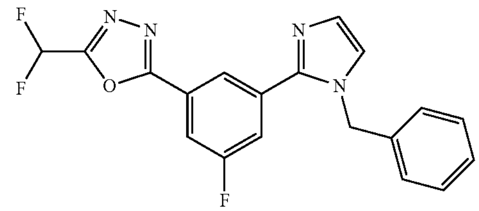 [SMILES: Fc1cc(-c2nnc(C(F)F)o2)cc(-c2nccn2Cc2ccccc2)c1] | 371.1 |
| 5a | 3-(benzyloxy)-2-{3-[5-(difluoromethyl)-1,3,4-oxadiazol-2-yl]-5-fluorophenyl}pyridine | 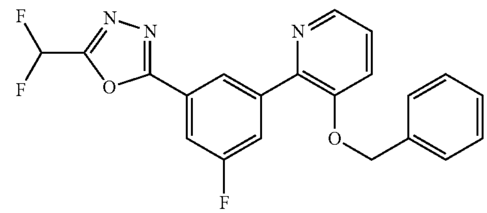 [SMILES: Fc1cc(-c2nnc(C(F)F)o2)cc(-c2ncccc2OCc2ccccc2)c1] | 398.2 |
| 6a | 2-[(2-{3-[5-(difluoromethyl)-1,3,4-oxadiazol-2-yl]-5-fluorophenyl}-1H-imidazol-1-yl)methyapyridine | 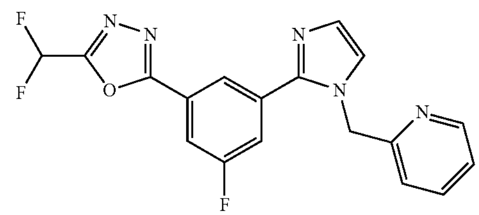 [SMILES: Fc1cc(-c2nnc(C(F)F)o2)cc(-c2nccn2Cc2ccccn2)c1] | 372.2 |
| 7a | 2-{3-[5-(difluoromethyl)-1,3,4-oxadiazol-2-yl]-5-fluorophenyl]-3-[(oxan-4-yl)methoxy]pyridine | 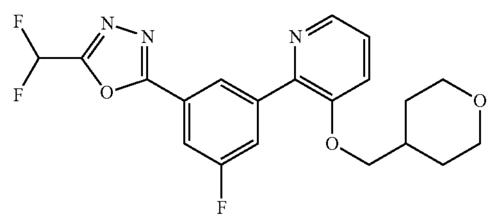 [SMILES: Fc1cc(-c2nnc(C(F)F)o2)cc(-c2ncccc2OCC2CCOCC2)c1] | 406.2 |
| 8a | 2-{3-[5-(difluoromethyl)-1,3,4-oxadiazol-2-yl]-5-fluorophenyl)-3-[(oxan-4-yl)oxy]pyridine | 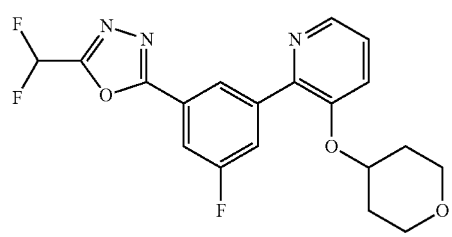 [SMILES: Fc1cc(-c2nnc(C(F)F)o2)cc(-c2ncccc2OC2CCOCC2)c1] | 392.2 |
| 9a | 2-{3-[5-(difluoromethyl)-1,3,4-oxadiazol-2-yl]-5-fluorophenyl}-3-[(4-methylphenyl)methoxy]pyridine | 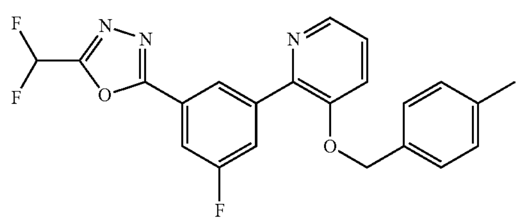 [SMILES: Cc1ccc(COc2cccnc2-c2cc(F)cc(-c3nnc(C(F)F)o3)c2)cc1] | 412.2 |

TABLE 1-continued

| Example | IUPAC name | Structure | MS |
|---|---|---|---|
| 10a | 2-(3-[5-(difluoromethyl)-1,3,4-oxadiazol-2-yl]-5-fluorophenyl)-3-[(1,5-dimethyl-1H-pyrazol-3-yl)methoxy]pyridine | 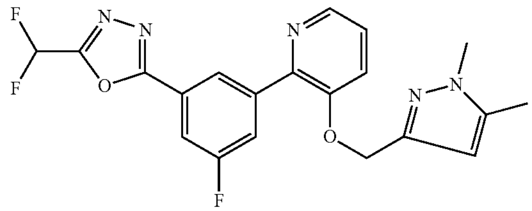 [SMILES: Cc1cc(COc2cccnc2-c2cc(F)cc(-c3nnc(C(F)F)o3)c2)nn1C] | 416.2 |
| 11a | 2-{3-[5-(difluoromethyl)-1,3,4-oxadiazol-2-yl]-5-fluorophenyl}-3-[(pyridin-2-yl)methoxy]pyridine | 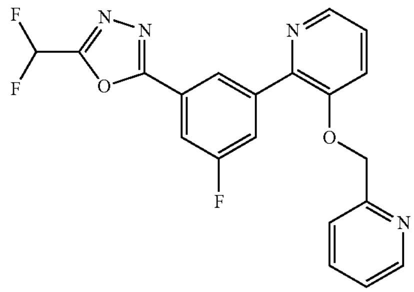 [SMILES: Fc1cc(-c2nnc(C(F)F)o2)cc(-c2ncccc2OCc2ccccn2)c1] | 399.2 |
| 12a | 2-{3-[5-(difluoromethyl)-1,3,4-oxadiazol-2-yl]-5-fluorophenyl}-3-[(oxolan-3-yl)methoxy]pyridine | 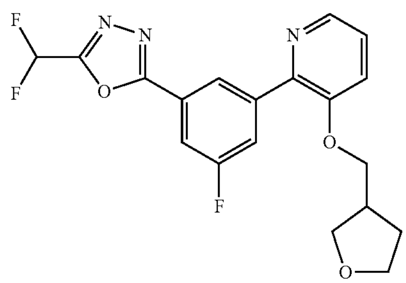 [SMILES: Fc1cc(-c2nnc(C(F)F)o2)cc(-c2ncccc2OCC2CCOC2)c1] | 392.1 |
| 13a | 2-{3-[5-(difluoromethyl)-1,3,4-oxadiazol-2-yl]-5-fluorophenyl}-3-(2-methoxyethoxy)pyridine | 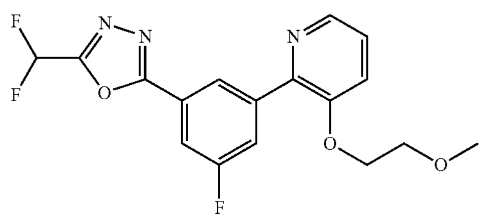 [SMILES: COCCOc1cccnc1-c1cc(F)cc(-c2nnc(C(F)F)o2)c1] | 366.1 |
| 14a | 4-{[(2-{3-[5-(difluoromethyl)-1,3,4-oxadiazol-2-yl]-5-fluorophenyl}pyridin-3-yl)oxy]methyl}-1-methylpiperidin-2-one | 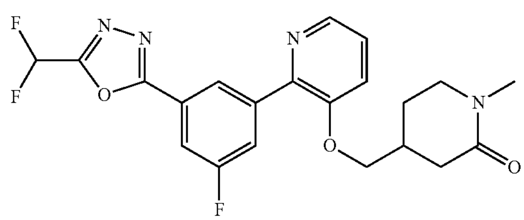 [SMILES: CN1CCC(COc2cccnc2-c2cc(F)cc(-c3nnc(C(F)F)o3)c2)CC1=O] | 433.2 |
| 15a | 1-{2-[(2-{3-[5-(difluoromethyl)-1,3,4-oxadiazol-2-yl]-5-fluorophenyl}pyridin-3-yl)oxy]ethyl}pyrrolidin-2-one | 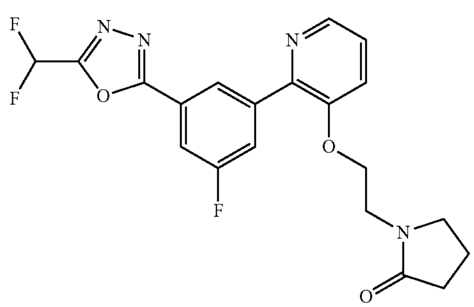 [SMILES: O=C1CCCN1CCOc1cccnc1-c1cc(F)cc(-c2nnc(C(F)F)o2)c1] | 419.2 |

TABLE 1-continued

| Example | IUPAC name | Structure | MS |
|---------|-----------|-----------|-----|
| 16a | tert-butyl 4-[(2-{3-[5-(difluoromethyl)-1,3,4-oxadiazol-2-yl]-5-fluorophenyl}pyridin-3-yl)oxy]piperidine-1-carboxylate | 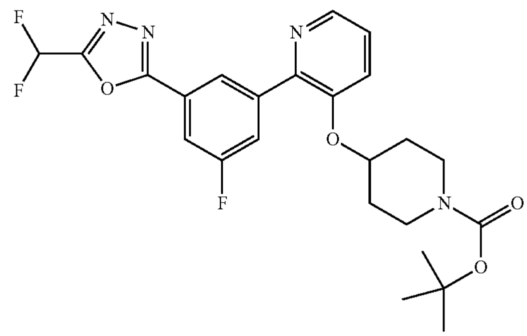 [SMILES: CC(C)(C)OC(=O)N1CCC(Oc2cccnc2-c2cc(F)cc(-c3nnc(C(F)F)o3)c2)CC1] | 491.2 |
| 17a | tert-butyl 2-{[(2-{3-[5-(difluoromethyl)-1,3,4-oxadiazol-2-yl]-5-fluorophenyl}pyridin-3-yl)oxylmethyl}pyrrolidine-1-carboxylate | 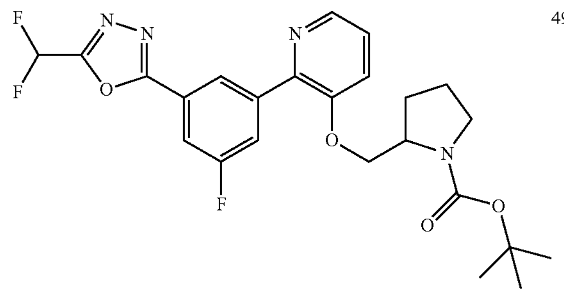 | 491.2 |
| 18a | 2-{3-[5-(difluoromethyl)-1,3,4-oxadiazol-2-yl]-5-fluorophenyl1-3-[(3-methyloxetan-3-yl)methoxy]pyridine | 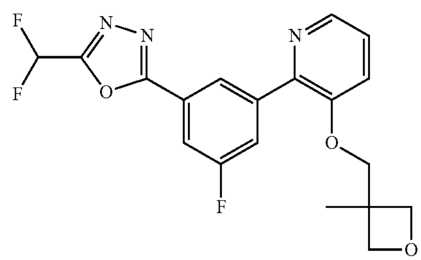 [SMILES: CC1(COc2cccnc2-c2cc(F)cc(-c3nnc(C(F)F)o3)c2)COC1] | 392.2 |
| 19a | ((5R)-5-benzyl-4-{4-[5-difluoromethyl)-1,3,4-oxadiazol-2-yl]pyridin-2-yl}morpholin-3-one | 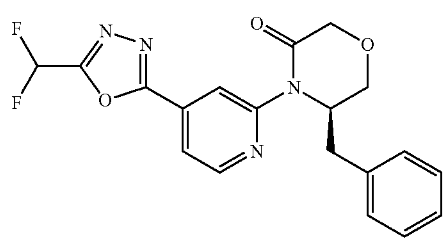 [SMILES: O=C1COC[C@@H](Cc2ccccc2)N1c1cc(-c2nnc(C(F)F)o2)ccn1] | 387.1 |
| 20a | 2-(3-{1-[(2-chlorophenyl)methyl]-1H-imidazol-2-yl}-5-fluorophenyl)-5-(difluoromethyl)-1,3,4-oxadiazole | 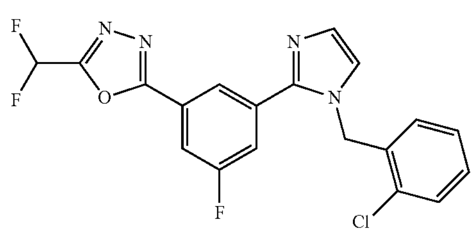 [SMILES: Fc1cc(-c2nnc(C(F)F)o2)cc(-c2nccn2Cc2ccccc2Cl)c1] | 405.1 |
| 21a | 2-(3-[1-[(3-chlorophenyl)methyl]-1H-imidazol-2-yl}-5-fluorophenyl)-5-(difluoromethyl)-1,3,4-oxadiazole | 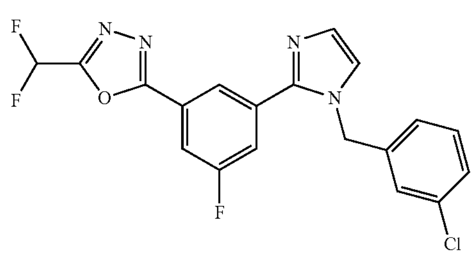 [SMILES: Fc1cc(-c2nnc(C(F)F)o2)cc(-c2nccn2Cc2cccc(Cl)c2)c1] | 405.1 |

TABLE 1-continued

| Example | IUPAC name | Structure | MS |
|---|---|---|---|
| 22a | 2-(3-{1-[(4-chlorophenyl)methyl]-1H-imidazol-2-yl}-5-fluorophenyl)-5-(difluoromethyl)-1,3,4-oxadiazole | 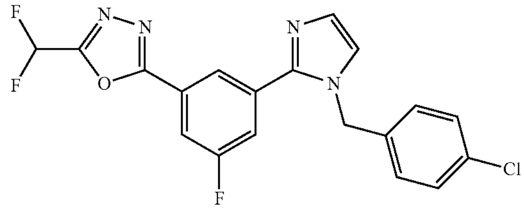 [SMILES: Fc1cc(-c2nnc(C(F)F)o2)cc(-c2nccn2Cc2ccc(Cl)cc2)c1] | 405.1 |
| 23a | 2-(difluoromethyl)-5-(3-fluoro-5-{1-[(1-methyl-1H-pyrazol-3-yl)methyl]-1H-imidazol-2-yl}phenyl)-1,3,4-oxadiazole | 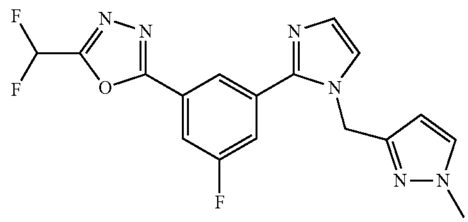 [SMILES: Cn1ccc(Cn2ccnc2-c2cc(F)cc(-c3nnc(C(F)F)o3)c2)n1] | 375.2 |
| 24a | 4-[(2-{3-[5-(difluoromethyl)-1,3,4-oxadiazol-2-yl]-5-fluorophenyl}-1H-imidazol-1-yl)methyl]pyridine | 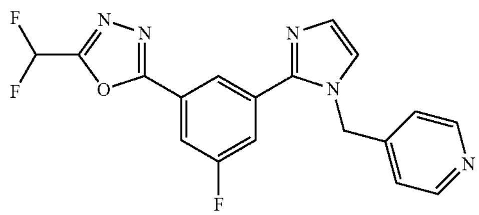 [SMILES: Fc1cc(-c2nnc(C(F)F)o2)cc(-c2nccn2Cc2ccncc2)c1] | 372.2 |
| 25a | 5-[(2-{3-[5-(difluoromethyl)-1,3,4-oxadiazol-2-yl]-5-fluorophenyl}-1H-imidazol-1-yl)methyl]pyrimidine | 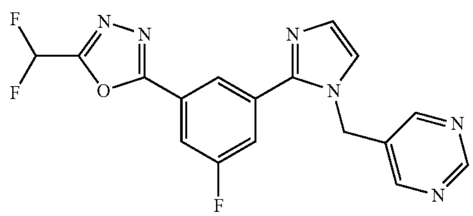 | 373.2 |
| 26a | 3-[(2-{3-[5-(difluoromethyl)-1,3,4-oxadiazol-2-yl]-5-fluorophenyl}-1H-imidazol-1-yl)methyapyridazine | 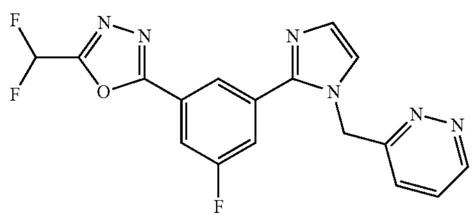 [SMILES: Fc1cc(-c2nnc(C(F)F)o2)cc(-c2nccn2Cc2cccnn2)c1] | 373.2 |
| 27a | 2-(difluoromethyl)-5-{3-fluoro-5-[1-(2-methoxyethyl)-1H-imidazol-2-yl]phenyl{-1,3,4-oxadiazole | 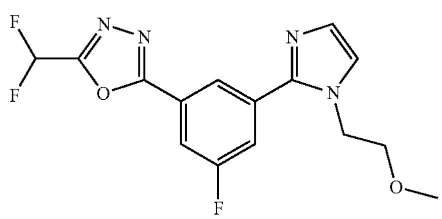 [SMILES: COCCn1ccnc1-c1cc(F)cc(-c2nnc(C(F)F)o2)c1] | 339.1 |
| 28a | 2-(3-{1-[(4,4-difluorocyclohexyl)methyl]-1H-imidazol-2-yl)-5-fluorophenyl)-5-(difluoromethyl)-1,3,4-oxadiazole | 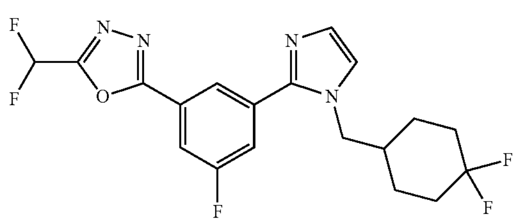 [SMILES: Fc1cc(-c2nnc(C(F)F)o2)cc(-c2nccn2CC2CCC(F)(F)CC2)c1] | 413.3 |

TABLE 1-continued

| Example | IUPAC name | Structure | MS |
|---|---|---|---|
| 29a | 2-(difluoromethyl)-5-(3-fluoro-5-{1-[(oxan-3-yl)methyl]-1H-imidazol-2-yl}phenyl)-1,3,4-oxadiazole | 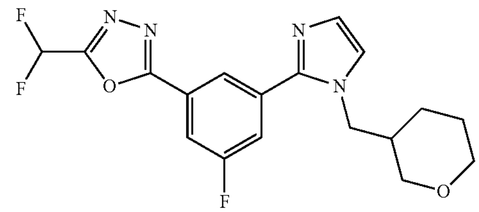 [SMILES: Fc1cc(-c2nnc(C(F)F)o2)cc(-c2nccn2CC2CCCOC2)c1] | 379.2 |
| 30a | 2-(difluoromethyl)-5-(3-fluoro-5-{1-[(oxan-4-yl)methyl]-1H-imidazol-2-yl}phenyl)-1,3,4-oxadiazole | 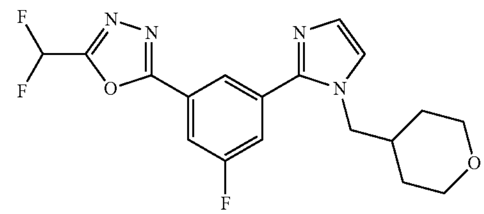 [SMILES: Fc1cc(-c2nnc(C(F)F)o2)cc(-c2nccn2CC2CCOCC2)c1] | 379.2 |
| 31a | 1-{4-[(2-{3-[5-(difluoromethyl)-1,3,4-oxadiazol-2-yl]-5-fluorophenyl}-1H-imidazol-1-yl)methyl]piperidin-1-yl}ethan-1-one | 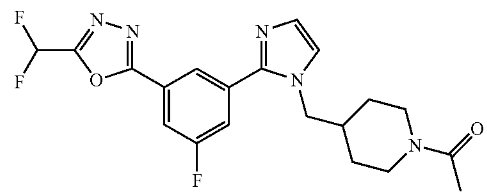 [SMILES: CC(=O)N1CCC(Cn2ccnc2-c2cc(F)cc(-c3nnc(C(F)F)o3)c2)CC1] | 420.3 |
| 32a | 2-(2-{3-[5-(difluoromethyl)-1,3,4-oxadiazol-2-yl]-5-fluorophenyl]-1H-imidazol-1-yl)-N-ethylacetamide | 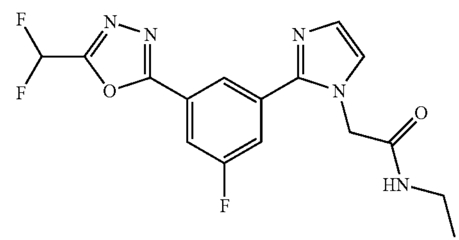 [SMILES: CCNC(=O)Cn1ccnc1-c1cc(F)cc(-c2nnc(C(F)F)o2)c1] | 366.2 |
| 33a | 2-(2-{3-[5-(difluoromethyl)-1,3,4-oxadiazol-2-yl]-5-fluorophenyl}-1H-imidazol-1-yl)-1-(pyrrolidin-1-yl)ethan-1-one | 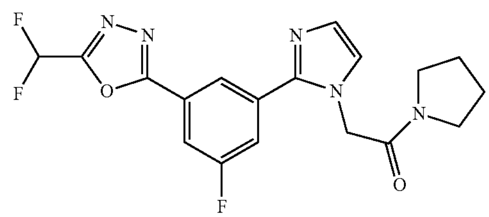 [SMILES: O=C(Cn1ccnc1-c1cc(F)cc(-c2nnc(C(F)F)o2)c1)N1CCCC1] | 392.2 |
| 34a | 4-[(2-{3-[5-(difluoromethyl)-1,3,4-oxadiazol-2-yl]-5-fluorophenyl}-1H-imidazol-1-yl)methyl]-2-fluoro-N-methylbenzamide | 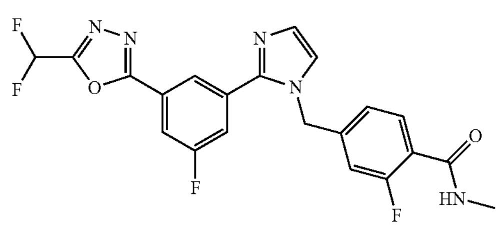 [SMILES: CNC(=O)c1ccc(Cn2ccnc2-c2cc(F)cc(-c3nnc(C(F)F)o3)c2)cc1F] | 446.2 |
| 35a | 4-(benzyloxy)-3-{3-[5-(difluoromethyl)-1,3,4-oxadiazol-2-yl]-5-fluorophenyl}-1-methylpyridin-2(1H)-one | 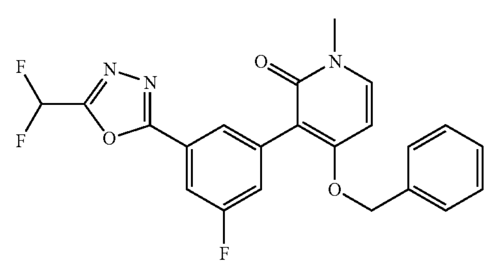 [SMILES: Cn1ccc(OCc2ccccc2)c(-c2cc(F)cc(-c3nnc(C(F)F)o3)c2)c1=O] | 428.2 |

TABLE 1-continued

| Example | IUPAC name | Structure | MS |
|---|---|---|---|
| 36a | 2-(1-benzyl-1H-imidazol-2-yl)-4-[5-(difluoromethyl)-1,3,4-oxadiazol-2-yl]pyridine | 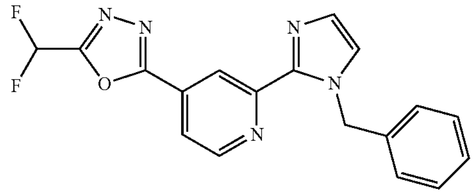 [SMILES: FC(F)c1nnc(-c2ccnc(-c3nccn3Cc3ccccc3)c2)o1] | 354.2 |
| 37a | 3-(1-benzyl-1H-imidazol-2-yl)-5-[5-(difluoromethyl)-1,3,4-oxadiazol-2-yl]pyridine | 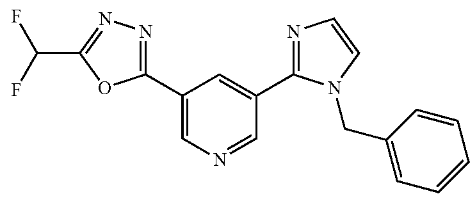 [SMILES: FC(F)c1nnc(-c2cncc(-c3nccn3Cc3ccccc3)c2)o1] | 354.2 |
| 38a | 2-[5-chloro-1-[(pyridin-2-yl)methyl]-1H-imidazol-2-yl]-4-[5-(difluoromethyl)-1,3,4-oxadiazol-2-yl]pyridine | 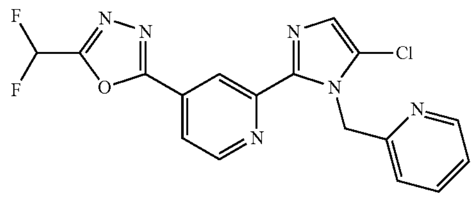 [SMILES: FC(F)c1nnc(-c2ccnc(-c3ncc(Cl)n3Cc3ccccn3)c2)o1] | 389.2 |
| 39a | 2-{4-chloro-1-[(pyridin-2-yl)methyl]-1H-imidazol-2-yl}-4-[5-(difluoromethyl)-1,3,4-oxadiazol-2-yl]pyridine | 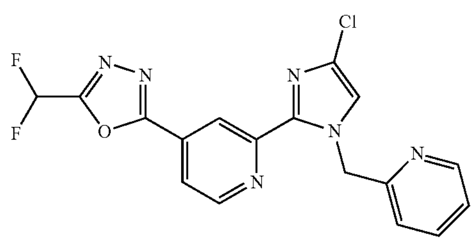 [SMILES: FC(F)c1nnc(-c2ccnc(-c3nc(Cl)cn3Cc3ccccn3)c2)o1] | 389.2 |
| 40a | 2-{4,5-dichloro-1-[(pyridin-2-yl)methyl]-1H-imidazol-2-yl}-4-[5-(difluoromethyl)-1,3,4-oxadiazol-2-yl]pyridine | 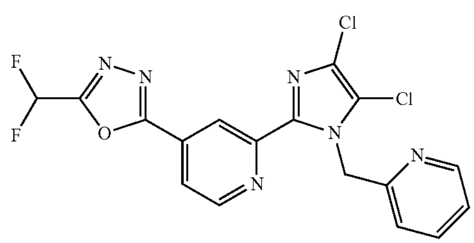 [SMILES: FC(F)c1nnc(-c2ccnc(-c3nc(Cl)c(Cl)n3Cc3ccccn3)c2)o1] | 423.1 |
| 41a | 3-{3-[5-(difluoromethyl)-1,3,4-oxadiazol-2-yl]-5-fluorophenyl}-4-[(pyridin-2-yl)methyl]-1,3-oxazolidin-2-one | 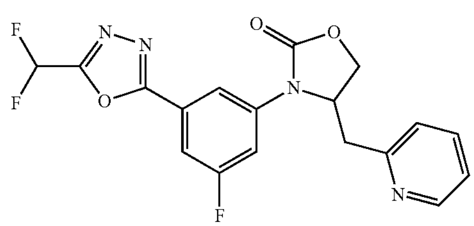 [SMILES: O=C1OCC(Cc2ccccn2)N1c1cc(F)cc(-c2nnc(C(F)F)o2)c1] | 391.2 |
| 42a | 4-{3-[5-(difluoromethyl)-1,3,4-oxadiazol-2-yl]-5-fluorophenyl}-5-[(pyridin-2-yl)methyamorpholin-3-one | 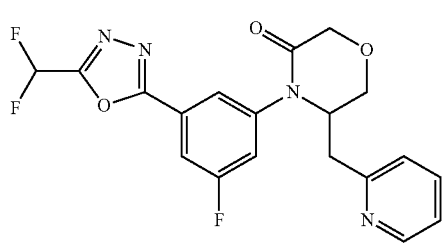 [SMILES: O=C1COCC(Cc2ccccn2)N1c1cc(F)cc(-c2nnc(C(F)F)o2)c1] | 405.2 |

TABLE 1-continued

| Example | IUPAC name | Structure | MS |
|---|---|---|---|
| 43a | 2-[(2-{3-[5-(difluoromethyl)-1,3,4-oxadiazol-2-yl]-5-fluorophenyl}-1H-imidazol-1-yl)methyl]pyrazine | 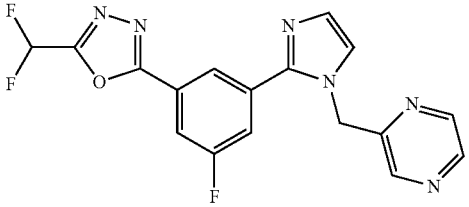 [SMILES: Fc1cc(-c2nnc(C(F)F)o2)cc(-c2nccn2Cc2cnccn2)c1] | 373.2 |
| 44a | 2-(difluoromethyl)-5-(3-fluoro-5-{1-[(3-fluorophenyl)methyl]-1H-imidazol-2-yl}phenyl)-1,3,4-oxadiazole | 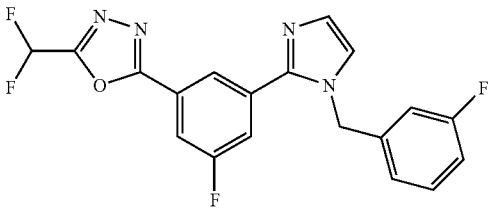 [SMILES: Fc1cccc(Cn2ccnc2-c2cc(F)cc(-c3nnc(C(F)F)o3)c2)c1] | 389.2 |
| 45a | 2-(difluoromethyl)-5-(3-{1-[(3,4-difluorophenyl)methyl]-1H-imidazol-2-yl}-5-fluorophenyl)-1,3,4-oxadiazole | 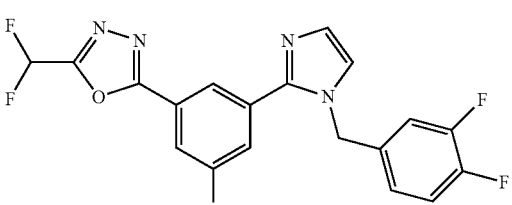 | 407.2 |
| 46a | 2-(difluoromethyl)-5-(3-fluoro-5-{1-[(4-fluorophenyl)methyl]-1H-imidazol-2-yl}phenyl)-1,3,4-oxadiazole | 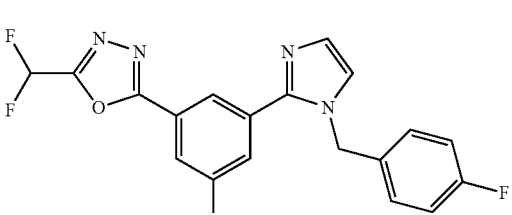 | 389.2 |
| 47a | 2-(difluoromethyl)-5-(3-fluoro-5-{5-[(oxan-4-yl)oxy]-1H-pyrazol-1-yl}phenyl)-1,3,4-oxadiazole | 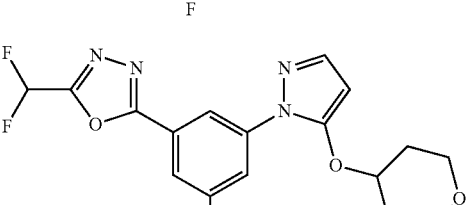 | 381.2 |
| 49a | 3-[(2-{3-[5-(difluoromethyl)-1,3,4-oxadiazol-2-yl]-5-fluorophenyl}-1H-imidazol-1-yl)methyapyridine | 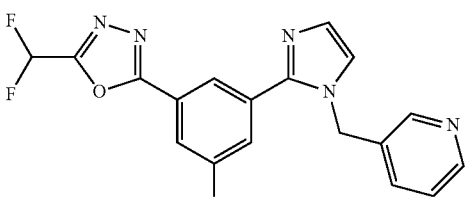 | 372.2 |
| 53a | 3-{3-[5-(difluoromethyl)-1,3,4-oxadiazol-2-yl]-5-fluorophenyl}-1-methyl-4-[(oxan-4-yl)oxy]pyridin-2(1H)-one | 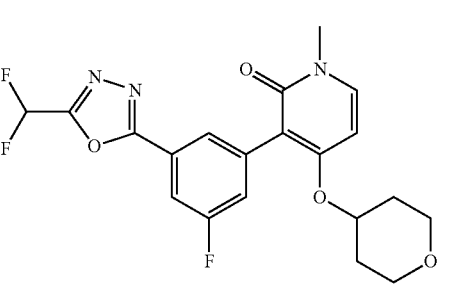 [SMILES: Cn1ccc(OC2CCOCC2)c(-c2cc(F)cc(-c3nnc(C(F)F)o3)c2)c1=O] | 422.2 |

TABLE 1-continued

| Example | IUPAC name | Structure | MS |
|---------|------------|-----------|-----|
| 54a | 2-(difluoromethyl)-5-(3-fluoro-5-{1-[(5-methyl-1,3,4-oxadiazol-2-yl)methyl]-1H-imidazol-2-yl}phenyl)-1,3,4-oxadiazole | 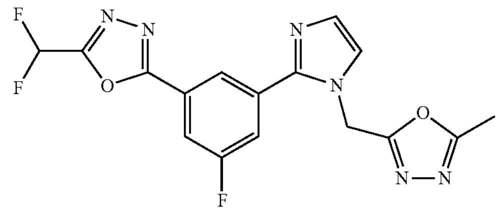 [SMILES: Cc1nnc(Cn2ccnc2-c2cc(F)cc(-c3nnc(C(F)F)o3)c2)o1] | 377.1 |
| 55a | 3-[(2-{3-[5-(difluoromethyl)-1,3,4-oxadiazol-2-yl]-5-fluorophenyl}-1H-imidazol-1-yl)methyl]-5-methyl-1,2,4-oxadiazole | 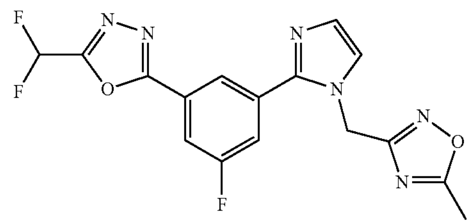 [SMILES: Cc1nc(Cn2ccnc2-c2cc(F)cc(-c3nnc(C(F)F)o3)c2)no1] | 377.1 |
| 56a | 5-[(2-{3-[5-(difluoromethyl)-1,3,4-oxadiazol-2-yl]-5-fluorophenyl}-1H-imidazol-1-yl)methyl]-3-methyl-1,2,4-oxadiazole | 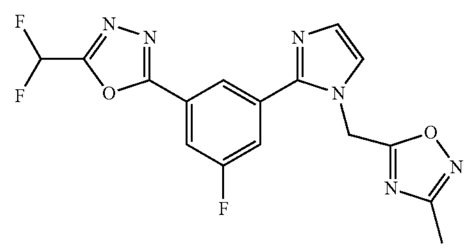 [SMILES: Cc1noc(Cn2ccnc2-c2cc(F)cc(-c3nnc(C(F)F)o3)c2)n1] | 377.1 |
| 57a | 2-(difluoromethyl)-5-(3-fluoro-5-{1-[(2-methyl-1,3-oxazol-4-yl)methyl]-1H-imidazol-2-yl}phenyl)-1,3,4-oxadiazole | 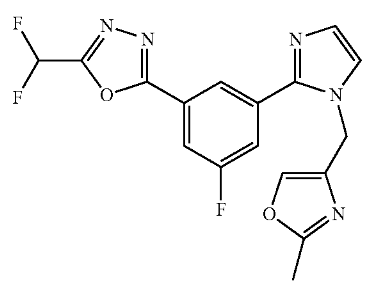 [SMILES: Cc1nc(Cn2ccnc2-c2cc(F)cc(-c3nnc(C(F)F)o3)c2)co1] | 376.1 |
| 58a | 2-[(2-{3-[5-(difluoromethyl)-1,3,4-oxadiazol-2-yl]-5-fluorophenyl}-1H-imidazol-1-yl)methyl]-6-methoxypyrazine | 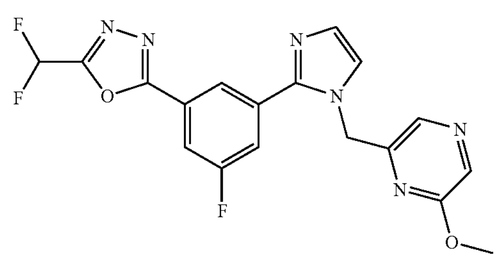 [SMILES: COc1cncc(Cn2ccnc2-c2cc(F)cc(-c3nnc(C(F)F)o3)c2)n1] | 403.2 |
| 59a | 2-(difluoromethyl)-5-(3-fluoro-5-{1-[(1-methyl-1H-pyrazol-4-yl)methyl]-1H-imidazol-2-yl}phenyl)-1,3,4-oxadiazole | 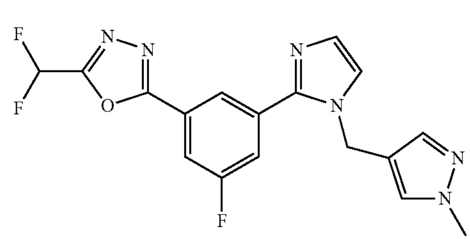 [SMILES: Cn1cc(Cn2ccnc2-c2cc(F)cc(-c3nnc(C(F)F)o3)c2)cn1] | 375.1 |

TABLE 1-continued

| Example | IUPAC name | Structure | MS |
|---------|------------|-----------|-----|
| 60a | 2-(difluoromethyl)-5-(3-fluoro-5-{1-[(1,3-thiazol-4-yl)methyl]-1H-imidazol-2-yl}phenyl)-1,3,4-oxadiazole | 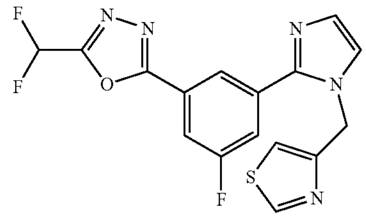 [SMILES: Fc1cc(-c2nnc(C(F)F)o2)cc(-c2nccn2Cc2cscn2)c1] | 378.1 |
| 61a | 2-(difluoromethyl)-5-(3-fluoro-5-{1-[(5-methyl-1,2-oxazol-3-yl)methyl]-1H-imidazol-2-yl}phenyl)-1,3,4-oxadiazole | 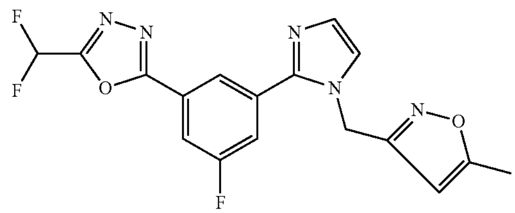 [SMILES: Cc1cc(Cn2ccnc2-c2cc(F)cc(-c3nnc(C(F)F)o3)c2)no1] | 376.1 |
| 62a | 2-(difluoromethyl)-5-(3-fluoro-5-{1-[(3-methyl-1,2-oxazol-5-yl)methyl]-1H-imidazol-2-yl}phenyl)-1,3,4-oxadiazole | 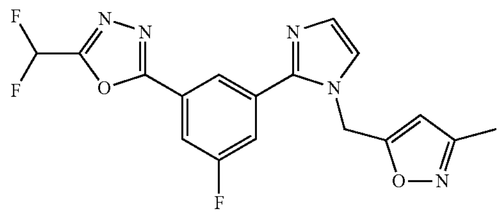 [SMILES: Cc1cc(Cn2ccnc2-c2cc(F)cc(-c3nnc(C(F)F)o3)c2)on1] | 376.1 |
| 63a | 2-(difluoromethyl)-5-(3-{1-[(1,3-dimethyl-1H-pyrazol-4-yl)methyl]-1H-imidazol-2-yl}-5-fluorophenyl)-1,3,4-oxadiazole | 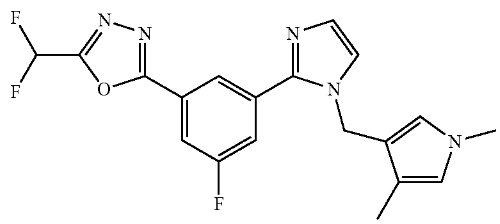 [SMILES: Cc1cn(C)cc1Cn1ccnc1-c1cc(F)cc(-c2nnc(C(F)F)o2)c1] | 389.2 |
| 64a | 2-(difluoromethyl)-5-(3-{1-[(1,3-dimethyl-1H-pyrazol-5-yl)methyl]-1H-imidazol-2-yl}-5-fluorophenyl)-1,3,4-oxadiazole | 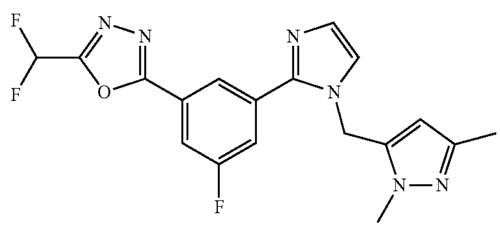 [SMILES: Cc1cc(Cn2ccnc2-c2cc(F)cc(-c3nnc(C(F)F)o3)c2)n(C)n1] | 389.2 |
| 65a | 2-(difluoromethyl)-5-(3-{1-[(4,5-dimethyl-1,3-thiazol-2-yl)methyl]-1H-imidazol-2-yl}-5-fluorophenyl)-1,3,4-oxadiazole | 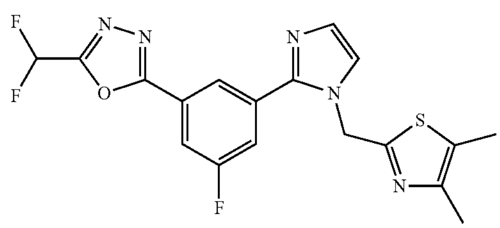 [SMILES: Cc1nc(Cn2ccnc2-c2cc(F)cc(-c3nnc(C(F)F)o3)c2)sc1C] | 406.2 |
| 66a | 5-[(2-{3-[5-(difluoromethyl)-1,3,4-oxadiazol-2-yl]-5-fluorophenyl}-1H-imidazol-1-yl)methyl]pyridine-2-carbonitrile | 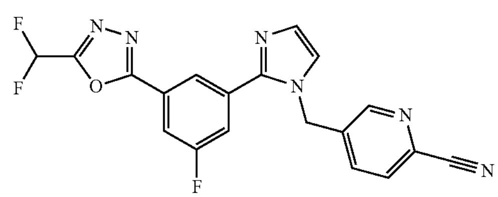 [SMILES: N#Cc1ccc(Cn2ccnc2-c2cc(F)cc(-c3nnc(C(F)F)o3)c2)cn1] | 397.2 |

TABLE 1-continued

| Example | IUPAC name | Structure | MS |
|---|---|---|---|
| 67a | 2-(difluoromethyl)-5-[3-fluoro-5-(1-{[3-(trifluoromethyl)phenyamethyl}-1H-imidazol-2-yl)phenyl]-1,3,4-oxadiazole | 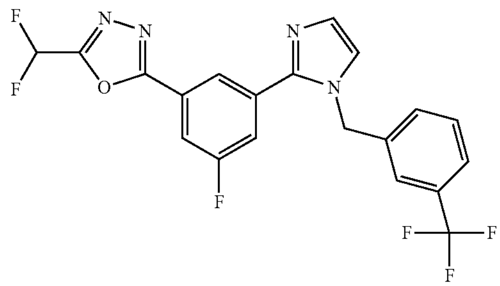 [SMILES: Fc1cc(-c2nnc(C(F)F)o2)cc(-c2nccn2Cc2cccc(C(F)(F)F)c2)c1] | 439.2 |
| 68a | 2-(3-{1-[(3-chloro-4-fluorophenyl)methyl]-1H-imidazol-2-yl}-5-fluorophenyl)-5-(difluoromethyl)-1,3,4-oxadiazole | 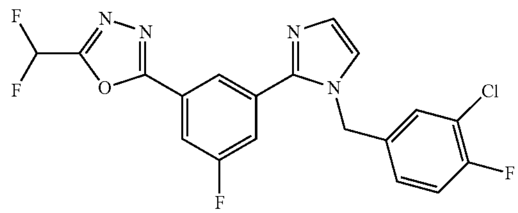 [SMILES: Fc1cc(-c2nnc(C(F)F)o2)cc(-c2nccn2Cc2ccc(F)c(Cl)c2)c1] | 423.1 |
| 70a | 2-[3-(1-benzyl-1H-imidazol-2-yl)phenyl]-5-(difluoromethyl)-1,3,4-oxadiazole | 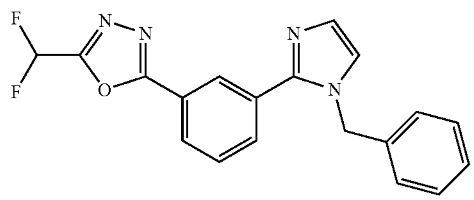 | 353.1 |
| 71a | 4-[5-(difluoromethyl)-1,3,4-oxadiazol-2-yl]-2-{1-[(3-fluorophenyl)methyl]-1H-imidazol-2-yl}pyridine | 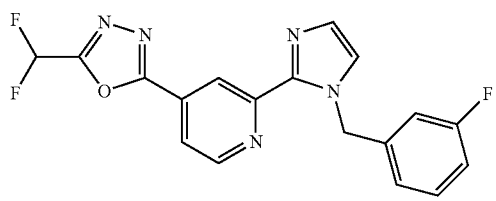 [SMILES: Fc1cccc(Cn2ccnc2-c2cc(-c3nnc(C(F)F)o3)ccn2)c1] | 372.2 |
| 72a | 3-[(2-{4-[5-(difluoromethyl)-1,3,4-oxadiazol-2-yl]pyridin-2-yl}-1H-imidazol-1-yl)methyl]benzonitrile | 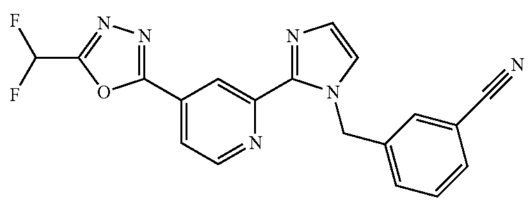 [SMILES: N#Cc1cccc(Cn2ccnc2-c2cc(-c3nnc(C(F)F)o3)ccn2)c1] | 379.2 |
| 73a | 4-[5-(difluoromethyl)-1,3,4-oxadiazol-2-yl]-2-{5-[(4-fluorophenyl)methyl]-1H-pyrazol-1-yl}pyridine | 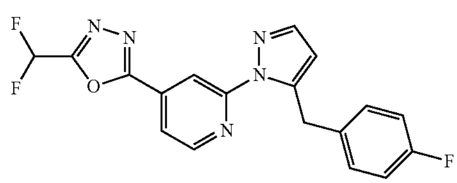 [SMILES: Fc1ccc(Cc2ccnn2-c2cc(-c3nnc(C(F)F)o3)ccn2)cc1] | 372.2 |
| 74a | 2-{5-bromo-1-[(3-fluorophenyl)methyl]-1H-imidazol-2-yl}-4-[5-(difluoromethyl)-1,3,4-oxadiazol-2-yl]pyridine | 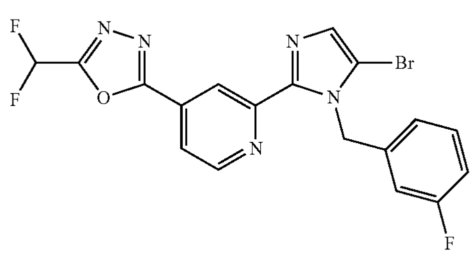 [SMILES: Fc1cccc(Cn2c(Br)cnc2-c2cc(-c3nnc(C(F)F)o3)ccn2)c1] | 450.1 |

TABLE 1-continued

| Example | IUPAC name | Structure | MS |
|---|---|---|---|
| 75a | 4-[(2-{4-[5-(difluoromethyl)-1,3,4-oxadiazol-2-yl]pyridin-2-yl}-1H-imidazol-1-yl)methyl]-2-fluorobenzonitrile | 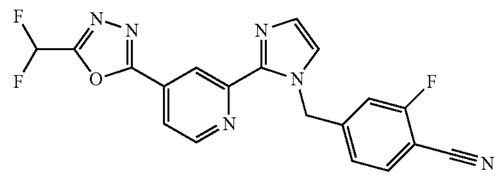 [SMILES: N#Cc1ccc(Cn2ccnc2-c2cc(-c3nnc(C(F)F)o3)ccn2)cc1F] | 397.2 |
| 76a | 4-[5-(difluoromethyl)-1,3,4-oxadiazol-2-yl]-2-{1-[(5-fluoropyridin-2-yl)methyl]-1H-imidazol-2-yl}pyridine | 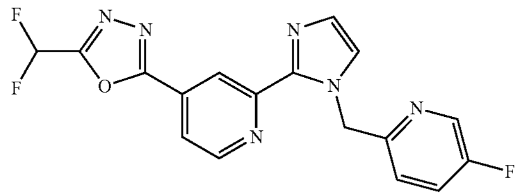 [SMILES: Fc1ccc(Cn2ccnc2-c2cc(-c3nnc(C(F)F)o3)ccn2)nc1] | 373.1 |
| 77a | 1-[4-[5-(difluoromethyl)-1,3,4-oxadiazol-2-yapyridin-2-yl]{-7-phenyl-4,5,6,7-tetrahydro-1H-indazole | 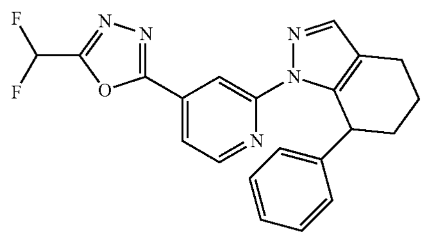 [SMILES: FC(F)c1nnc(-c2ccnc(-n3ncc4c3C(c3ccccc3)CCC4)c2)o1] | 394.2 |
| 78a | 4-[5-(difluoromethyl)-1,3,4-oxadiazol-2-yl]-2-{1-[(4-methylphenyl)methyl]-1H-imidazol-2-yl}pyridine | 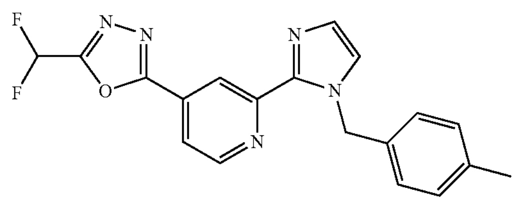 [SMILES: Cc1ccc(Cn2ccnc2-c2cc(-c3nnc(C(F)F)o3)ccn2)cc1] | 368.2 |
| 79a | 2-[(2-{4-[5-(difluoromethyl)-1,3,4-oxadiazol-2-yapyridin-2-yl}-1H-imidazol-1-yl)methyl]benzonitrile | 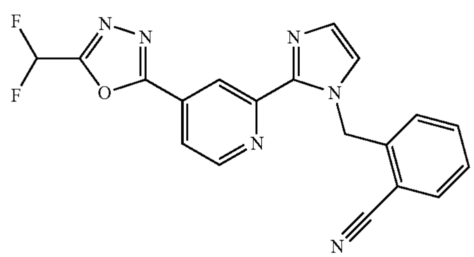 [SMILES: N#Cc1ccccc1Cn1ccnc1-c1cc(-c2nnc(C(F)F)o2)ccn1] | 379.2 |
| 80a | 4-[5-(difluoromethyl)-1,3,4-oxadiazol-2-yl]-2-{1-[(4-methoxyphenyl)methyl]-1H-imidazol-2-yl}pyridine | 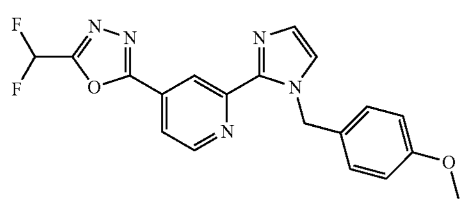 [SMILES: COc1ccc(Cn2ccnc2-c2cc(-c3nnc(C(F)F)o3)ccn2)cc1] | 384.2 |
| 81a | 4-[5-(difluoromethyl)-1,3,4-oxadiazol-2-yl]-2-{1-[(3-methoxyphenyl)methyl]-1H-imidazol-2-yl}pyridine | 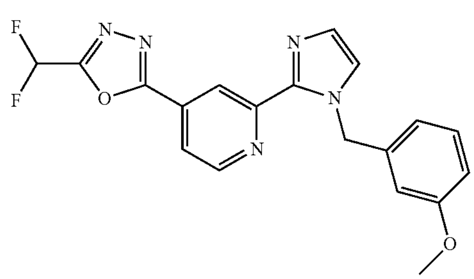 [SMILES: COc1cccc(Cn2ccnc2-c2cc(-c3nnc(C(F)F)o3)ccn2)c1] | 384.2 |

TABLE 1-continued

| Example | IUPAC name | Structure | MS |
|---|---|---|---|
| 82a | 2-[4-[5-(difluoromethyl)-1,3,4-oxadiazol-2-yl]pyridin-2-yl]-1-[(3-fluorphenyl)methyl]-1H-imidazole-5-carbonitrile | 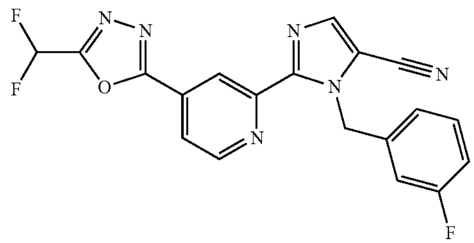 [SMILES: N#Cc1cnc(-c2cc(-c3nnc(C(F)F)o3)ccn2)n1Cc1cccc(F)c1] | 397.2 |
| 83a | 4-[5-(difluoromethyl)-1,3,4-oxadiazol-2-yl]-2-{1-[(3-methylphenyl)methyl]-1H-imidazol-2-yl}pyridine | 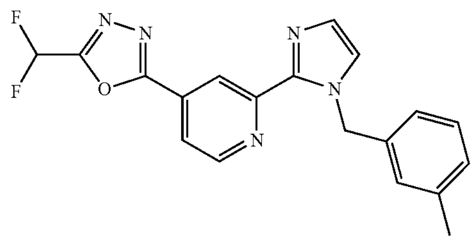 [SMILES: Cc1cccc(Cn2ccnc2-c2cc(-c3nnc(C(F)F)o3)ccn2)c1] | 368.2 |
| 84a | 4-[5-(difluoromethyl)-1,3,4-oxadiazol-2-yl]-2-{1-[(2-methoxyphenyl)methyl]-1H-imidazol-2-yl}pyridine | 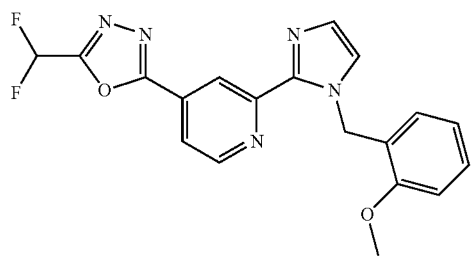 [SMILES: COc1ccccc1Cn1ccnc1-c1cc(-c2nnc(C(F)F)o2)ccn1] | 384.3 |
| 85a | 4-[5-(difluoromethyl)-1,3,4-oxadiazol-2-yl]-2-{1-[(3-fluorphenyl)methyl]-1H-1,2,4-triazol-5-yl}pyridine | 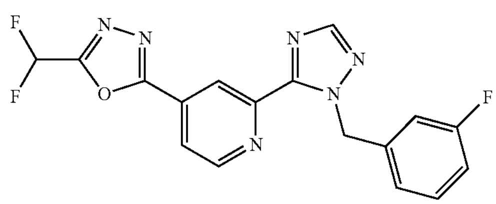 [SMILES: Fc1cccc(Cn2ncnc2-c2cc(-c3nnc(C(F)F)o3)ccn2)c1] | 373.2 |
| 86a | 4-[5-(difluoromethyl)-1,3,4-oxadiazol-2-yl]-2-{1-[(2-methylphenyl)methyl]-1H-imidazol-2-yl}pyridine | 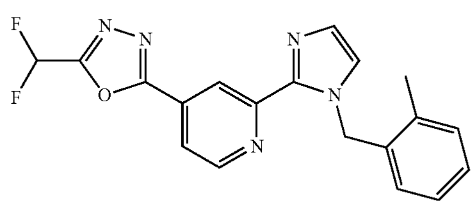 [SMILES: Cc1ccccc1Cn1ccnc1-c1cc(-c2nnc(C(F)F)o2)ccn1] | 368.2 |
| 87a | 4-[5-(difluoromethyl)-1,3,4-oxadiazol-2-yl]-2-{5-[(3-fluorophenyl)methyl]-1H-pyrazol-1-yl}pyridine | 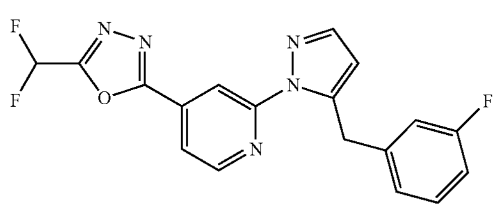 [SMILES: Fc1cccc(Cc2ccnn2-c2cc(-c3nnc(C(F)F)o3)ccn2)c1] | 372.2 |

TABLE 1-continued

| Example | IUPAC name | Structure | MS |
|---|---|---|---|
| 88a | 4'-[(4,4-difluorocyclohexyl)oxy]-4-[5-(difluoromethyl)-1,3,4-oxadiazol-2-yl]-1'-methyl[2,3'-bipyridine]-2'(1'H)-one | 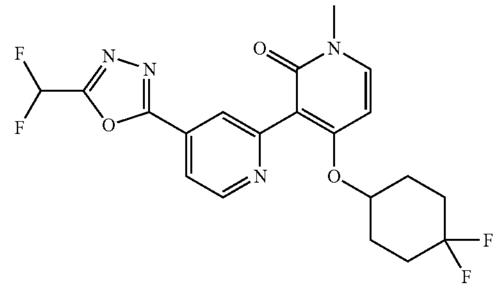 [SMILES: Cn1ccc(OC2CCC(F)(F)CC2)c(-c2cc(-c3nnc(C(F)F)o3)ccn2)c1=O] | 439.2 |
| 89a | 4-[5-(difluoromethyl)-1,3,4-oxadiazol-2-yl]-2-{5-[(3-fluorophenyl)methyl]-1H-1,2,4-triazol-1-yl}pyridine | 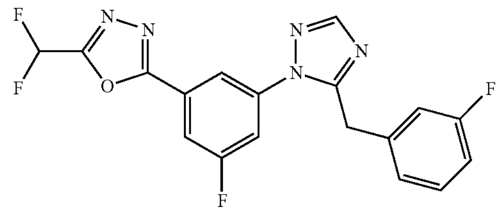 [SMILES: Fc1cccc(Cc2ncnn2-c2cc(F)cc(-c3nnc(C(F)F)o3)c2)c1] | 373.2 |
| 90a | 4-{4-[5-(difluoromethyl)-1,3,4-oxadiazol-2-yl]pyridin-2-yl}-5-[(3-fluorophenyl)methyl]pyrimidine | 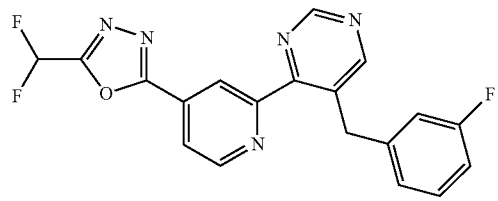 [SMILES: Fc1cccc(Cc2cncnc2-c2cc(-c3nnc(C(F)F)o3)ccn2)c1] | 384.1 |
| 91a | 4-[5-(difluoromethyl)-1,3,4-oxadiazol-2-yl]-1'-methyl-4'-[(oxan-4-yl)oxy][2,3'-bipyridine]-2'(1'H)-one | 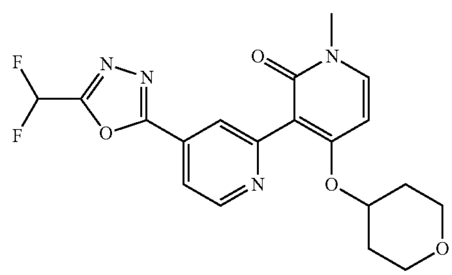 [SMILES: Cn1ccc(OC2CCOCC2)c(-c2cc(-c3nnc(C(F)F)o3)ccn2)c1=O] | 405.2 |
| 92a | 4-[5-(difluoromethyl)-1,3,4-oxadiazol-2-yl]-2-{1-[1-(3-fluorophenyl)ethyl]-1H-imidazol-2-yl}pyridine | 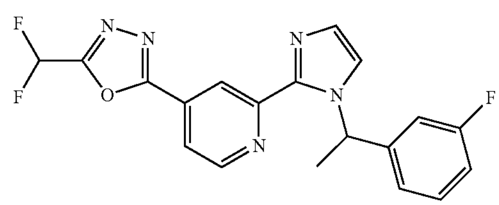 [SMILES: CC(c1cccc(F)c1)n1ccnc1-c1cc(-c2nnc(C(F)F)o2)ccn1] | 386.2 |
| 93a | 2-{1-[(5-chloropyridin-3-yl)methyl]-1H-imidazol-2-yl}-4-[5-(difluoromethyl)-1,3,4-oxadiazol-2-yl]pyridine | 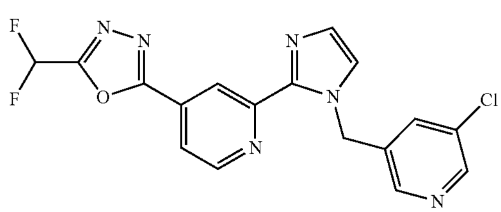 [SMILES: FC(F)c1nnc(-c2ccnc(-c3nccn3Cc3cncc(Cl)c3)c2)o1] | 389.1 |
| 94a | 6-[(2-{4-[5-(difluoromethyl)-1,3,4-oxadiazol-2-yl]pyridin-2-yl}-1H-imidazol-1-yl)methyl]pyridine-2-carbonitrile | 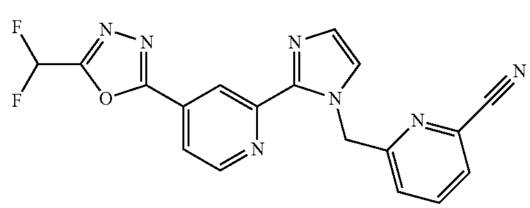 | 380.2 |

| Example | IUPAC name | Structure | MS |
|---|---|---|---|
| 95a | 2-[(2-{4-[5-(difluoromethyl)-1,3,4-oxadiazol-2-yl]pyridin-2-yl}-1H-imidazol-1-yl)methyl]pyridine-4-carbonitrile | 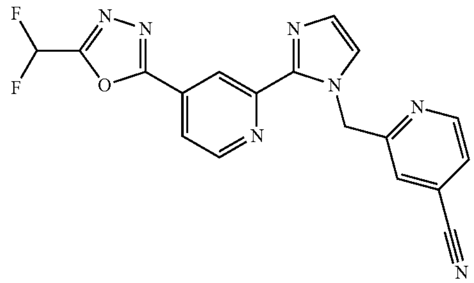 [SMILES: N#Cc1ccnc(Cn2ccnc2-c2cc(-c3nnc(C(F)F)o3)ccn2)c1] | 380.1 |

Example 1b

3-[5-(difluoromethyl)-1,3,4-oxadiazol-2-yl]-7-(4-fluorophenyl)-6,7-dimethyl-7,8-dihydro-1,6-naphthyridin-5(6H)-one (Optical Isomer 2)

A) 5-bromo-N,2-dimethylpyridine-3-carboxamide

To a mixture of 5-bromo-2-methylnicotinic acid (5 g) and THF (40 ml) were added oxalyl chloride (3.03 ml) and DMF (one drop) at 0° C., and the mixture was stirred for 3 hr. The mixture was concentrated under reduced pressure, to a mixture of the obtained residue and THF (40 ml) were added methanamine hydrochloride (1.953 g) and TEA (6.45 ml) at room temperature, and the mixture was stirred for 2 hr. HATU (4.40 g) was added to the reaction solution, and the mixture was stirred for additional 1 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (2.28 g).

MS: [M+H]$^+$ 229.0.

B) 5-bromo-2-[2-(4-fluorophenyl)-2-hydroxypropyl]-N-methylpyridine-3-carboxamide To a mixture of 5-bromo-N,2-dimethylpyridine-3-carboxamide (0.6 g) and THF (10.48 ml) was added lithium diisopropylamide (3.84 ml) at −78° C. The mixture was stirred under argon atmosphere at 0° C. for 20 min. To the reaction solution was added 4'-fluoroacetophenone (0.38 ml) at −78° C., and the mixture was stirred under argon atmosphere at 0° C. for 1 hr. To the mixture was added saturated brine, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (677 mg).

MS: [M+H]$^+$ 367.1.

C) 3-bromo-7-(4-fluorophenyl)-6,7-dimethyl-7,8-dihydro-1,6-naphthyridin-5(6H)-one A mixture of 5-bromo-2-[2-(4-fluorophenyl)-2-hydroxypropyl]-N-methylpyridine-3-carboxamide (840 mg) and sulfuric acid (5 ml) was stirred at 0° C. for 2 hr. To the mixture was added ice water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (288 mg).

MS: [M+H]$^+$ 349.1.

D) tert-butyl 2-[7-(4-fluorophenyl)-6,7-dimethyl-5-oxo-5,6,7,8-tetrahydro-1,6-naphthyridine-3-carbonyl]hydrazine-1-carboxylate To a mixture of 3-bromo-7-(4-fluorophenyl)-6,7-dimethyl-7,8-dihydro-1,6-naphthyridin-5(6H)-one (280 mg) and CPME (3207 μl) were added tert-butyl hydrazinecarboxylate (159 mg), N-cyclohexyl-N-methylcyclohexanamine (313 mg), XANTPHOS (46.4 mg) and bis(dibenzylideneacetone)palladium(0) at room temperature. The mixture was stirred under carbon monoxide atmosphere at 100° C. for 5 hr. The impurities were removed by filtration, and the filtrate was concentrated under reduced pressure. The residue was purified by silica gel column chromatography (ethyl acetate/hexane) to give a solid (468 mg) containing the title compound. The solid was used in the next reaction without purification.

MS: [M+H]$^+$ 429.3.

E) 3-[5-(difluoromethyl)-1,3,4-oxadiazol-2-yl]-7-(4-fluorophenyl)-6,7-dimethyl-7,8-dihydro-1,6-naphthyridin-5(6H)-one A mixture of tert-butyl 2-[7-(4-fluorophenyl)-6,7-dimethyl-5-oxo-5,6,7,8-tetrahydro-1,6-naphthyridine-3-carbonyl]hydrazine-1-carboxylate (468 mg) and 4 N hydrochloric acid-ethyl acetate solution (5 ml) was stirred at room temperature for 2 hr, and the reaction solution was concentrated. To a solution of the obtained residue in THF (2 mL) were added difluoroacetic anhydride (285 mg) and DIPEA (424 mg), and the mixture was stirred at room temperature for 2 hr. To the mixture was added saturated brine at room temperature, and the mixture was extracted with ethyl acetate. The organic layer was separated, washed with saturated brine, dried over anhydrous magnesium sulfate, and concentrated under reduced pressure. To a solution of the obtained residue in THF (5 mL) were added 4-methylbenzenesulfonyl chloride (625 mg) and DIPEA (424 mg), and the mixture was stirred at 50° C. for 2 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (81 mg).
¹H NMR (400 MHz, DMSO-$d_6$) δ 1.75-1.92 (3H, m), 3.05 (3H, s), 3.53-3.76 (2H, m), 7.04-7.20 (2H, m), 7.25-7.37 (2H, m), 7.40-7.83 (1H, m), 8.54-8.70 (1H, m), 9.06-9.25 (1H, m)

F) 3-[5-(difluoromethyl)-1,3,4-oxadiazol-2-yl]-7-(4-fluorophenyl)-6,7-dimethyl-7,8-dihydro-1,6-naphthyridin-5(6H)-one (optical isomer 2)

3-(5-(Difluoromethyl)-1,3,4-oxadiazol-2-yl)-7-(4-fluorophenyl)-6,7-dimethyl-7,8-dihydro-1,6-naphthyridin-5(6H)-one (68.6 mg) was subjected to optical resolution by chiral HPLC (column: CHIRALCEL OD-H (DAICEL), 20 mmID×250 mmL, mobile phase: EtOH) to give the title compound with longer retention time (30.5 mg, 99.8% ee, analysis chiral HPLC (column: CHIRALCEL OD-H (DAICEL), 4.6 mmID×250 mmL, mobile phase: EtOH, retention time:18.80 min).
¹H NMR (400 MHz, DMSO-$d_6$) δ 1.80-1.87 (3H, m), 2.99-3.08 (3H, m), 3.52-3.78 (2H, m), 7.07-7.17 (2H, m), 7.26-7.34 (2H, m), 7.43-7.72 (1H, m), 8.57-8.71 (1H, m), 9.07-9.24 (1H, m).

Example 2b

7-[5-(difluoromethyl)-1,3,4-oxadiazol-2-yl]-3-(4-fluorophenyl)-3,4-dihydrophthalazin-1(2H)-one A) tert-butyl 2-(3-(methoxycarbonyl)-4-methylbenzoyl)hydrazinecarboxylate A mixture of methyl 5-bromo-2-methylbenzoate (12.11 g), tert-butyl hydrazinecarboxylate (8.29 g), bis(dibenzylideneacetone)palladium(0) (1.511 g), XANTPHOS (1.512 g), N,N-dicyclohexylmethylamine (15.45 g) and cyclopentyl methyl ether (300 mL) was stirred under carbon monoxide atmosphere (0.5 MPa) at 95° C. for 5 hr. The catalyst was removed by filtration, the filtrate was concentrated under reduced pressure, and the residue was washed with diisopropyl ether. The obtained residue was purified by silica gel column chromatography (NH, ethyl acetate/hexane), and washed with diisopropyl ether and hexane to give the title compound (13.4 g).
MS: [M−H]⁻ 306.9.

B) methyl 5-(hydrazinocarbonyl)-2-methylbenzoate Hydrochloride

To tert-butyl 2-(3-(methoxycarbonyl)-4-methylbenzoyl)hydrazinecarboxylate (13.4 g) was added 4 M hydrogen chloride cyclopentyl methyl ether (200 mL) at room temperature. The mixture was stirred at room temperature for 3 days. The obtained solid was collected by filtration, and dried to give the title compound (10.79 g).
MS: [M+H]⁺ 209.2.

C) methyl 5-(5-(difluoromethyl)-1,3,4-oxadiazol-2-yl)-2-methylbenzoate

To a mixture of methyl 5-(hydrazinocarbonyl)-2-methylbenzoate hydrochloride (1 g) and THF (40 mL) was added DIPEA (3.57 mL) at room temperature. To the reaction mixture was added dropwise difluoroacetic anhydride (0.762 mL) at 0° C. The mixture was stirred at room temperature for 1 hr. To the reaction solution was added 4-methylbenzenesulfonyl chloride (1.558 g) at room temperature, and the mixture was stirred overnight. To the mixture was added water at room temperature, and the mixture was extracted with ethyl acetate. The organic layer was separated, washed with saturated aqueous sodium hydrogencarbonate solution, dried over anhydrous magnesium sulfate, and concentrated under reduced pressure. The residue was purified by silica gel column chromatography (ethyl acetate/hexane) to give the title compound (1.02 g).
MS: [M+H]⁺ 269.1.

D) methyl 2-(bromomethyl)-5-[5-(difluoromethyl)-1,3,4-oxadiazol-2-yl]benzoate

To a mixture of methyl 5-(5-(difluoromethyl)-1,3,4-oxadiazol-2-yl)-2-methylbenzoate (2.8 g) and benzotrifluoride (100 mL) were added NBS (2.79 g) and AIBN (0.171 g) at room temperature. The mixture was stirred under argon atmosphere at 90° C. for 1 hr. To the mixture was added water at room temperature, and the mixture was extracted with ethyl acetate. The organic layer was separated, washed with saturated brine, dried over anhydrous sodium sulfate, and concentrated under reduced pressure. To a mixture of the obtained residue and THF (100 mL) was added DIPEA (2.0 mL). To the mixture was added dropwise diethyl phosphonate (1.48 mL) at 0° C., and the mixture was stirred overnight at room temperature. To the mixture was added water at room temperature, and the mixture was extracted with ethyl acetate. The organic layer was separated, washed with saturated aqueous ammonium chloride solution and saturated brine, dried over anhydrous magnesium sulfate, and concentrated under reduced pressure. The residue was purified by silica gel column chromatography (ethyl acetate/hexane) to give the title compound (3.19 g).
MS: [M+H]⁺ 347.1.

E) 7-[5-(difluoromethyl)-1,3,4-oxadiazol-2-yl]-3-(4-fluorophenyl)-3,4-dihydrophthalazin-1(2H)-one To a mixture of (4-fluorophenyl)hydrazine hydrochloride (0.937 g), DIPEA (1.76 mL) and MeOH (30 mL) was added methyl 2-(bromomethyl)-5-[5-(difluoromethyl)-1,3,4-oxadiazol-2-yl]benzoate (1 g) at 0° C. The mixture was stirred overnight at room temperature. To the mixture was added water at room temperature, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (346 mg).
¹H NMR (400 MHz, DMSO-$d_6$) δ 5.04 (2H, s), 6.99-7.12 (4H, m), 7.36-7.70 (2H, m), 8.19 (1H, dd, J=7.9, 1.8 Hz), 8.37 (1H, d, J=1.7 Hz), 10.59 (1H, s).

Example 3b

3-[5-(difluoromethyl)-1,3,4-oxadiazol-2-yl]-7-(4-fluorophenyl)-7,8-dihydropyrido[2,3-d]pyridazin-5(6H)-one A) ethyl 5-[2-(tert-butoxycarbonyl)hydrazinecarbonyl]-2-methylpyridine-3-carboxylate A mixture of ethyl 5-bromo-2-methylpyridine-3-carboxylate (45 g), tert-butyl hydrazinecarboxylate (29.2 g), bis (dibenzylideneacetone)palladium(0) (5.30 g), XANTPHOS (5.33 g), N,N-dicyclohexylmethylamine (54.0 g) and cyclopentyl methyl ether (1000 mL) was stirred under carbon monoxide atmosphere (0.5 MPa) at 95° C. for 12 hr. The catalyst was removed by filtration, the filtrate was concentrated under reduced pressure, and the obtained residue was purified by silica gel column chromatography (petroleum ether/ethyl acetate) to give the title compound (57.7 g).

MS: $[M+H]^+$ 324.2.

B) ethyl 5-(hydrazinecarbonyl)-2-methylpyridine-3-carboxylate hydrochloride

To ethyl 5-[2-(tert-butoxycarbonyl)hydrazinecarbonyl]-2-methylpyridine-3-carboxylate (7.2 g) was added 4 M hydrogen chloride ethyl acetate (100 mL) at room temperature. The mixture was stirred at room temperature for 12 hr. The obtained solid was collected by filtration, and dried to give the title compound (4.43 g).

MS: $[M+H]^+$ 224.2.

C) ethyl 5-[5-(difluoromethyl)-1,3,4-oxadiazol-2-yl]-2-methylpyridine-3-carboxylate To a mixture of ethyl 5-(hydrazinecarbonyl)-2-methylpyridine-3-carboxylate hydrochloride (14 g) and THF (300 mL) was added DIPEA (34.8 g) at room temperature. To the reaction mixture was added dropwise difluoroacetic anhydride (14.1 g) at 0° C. The mixture was stirred at room temperature for 3 hr. To the reaction solution was added 4-methylbenzenesulfonyl chloride (7.22 g) at room temperature, and the mixture was stirred at 50° C. for 6 hr. The mixture was concentrated under reduced pressure. The residue was purified by silica gel column chromatography (petroleum ether/ethyl acetate) to give the title compound (8 g).

MS: $[M+H]^+$ 284.1.

D) ethyl 2-(bromomethyl)-5-[5-(difluoromethyl)-1,3,4-oxadiazol-2-yl]pyridine-3-carboxylate To a mixture of ethyl 5-[5-(difluoromethyl)-1,3,4-oxadiazol-2-yl]-2-methylpyridine-3-carboxylate (5.1 g) and benzotrifluoride (100 mL) were added NBS (5.77 g) and AIBN (0.296 g) at room temperature. The mixture was stirred under argon atmosphere at 90° C. for 1 hr. To the mixture was added water at room temperature, and the mixture was extracted with ethyl acetate. The organic layer was separated, washed with saturated brine, dried over anhydrous sodium sulfate, and concentrated under reduced pressure. To a mixture of the obtained residue and THF (100 mL) was added DIPEA (3.46 mL). To the mixture was added dropwise diethyl phosphonate (2.55 mL) at 0° C., and the mixture was stirred overnight at room temperature. To the mixture was added water at room temperature, and the mixture was extracted with ethyl acetate. The organic layer was separated, washed with saturated aqueous ammonium chloride solution and saturated brine, dried over anhydrous magnesium sulfate, and concentrated under reduced pressure. The residue was purified by silica gel column chromatography (ethyl acetate/hexane) to give the title compound (2.56 g).

MS: $[M+H]^+$ 362.0.

E) 3-[5-(difluoromethyl)-1,3,4-oxadiazol-2-yl]-7-(4-fluorophenyl)-7,8-dihydropyrido[2,3-d]pyridazin-5 (6H)-one To a mixture of (4-fluorophenyl)hydrazine hydrochloride (0.269 g), DIPEA (0.506 mL) and MeOH (10 mL) was added ethyl 2-(bromomethyl)-5-[5-(difluoromethyl)-1,3,4-oxadiazol-2-yl]pyridine-3-carboxylate (0.300 g) at 0° C. The mixture was stirred overnight at room temperature. To the mixture was added water at room temperature, and the mixture was extracted with ethyl acetate. The organic layer was washed with 10% citric acid, saturated aqueous sodium bicarbonate solution and saturated brine, dried over anhydrous sodium sulfate, and concentrated under reduced pressure. The residue was purified by HPLC (L-Column 2 ODS, mobile phase: water/acetonitrile (10 mM containing ammonium bicarbonate)). The obtained fraction was purified by HPLC (L-Column 2 ODS, mobile phase: water/acetonitrile (5 mM containing ammonium bicarbonate)). To the obtained fraction was added water, and the mixture was extracted with ethyl acetate. The organic layer was separated, dried over anhydrous sodium sulfate, and concentrated under reduced pressure to give the title compound (63.1 mg).

$^1$H NMR (400 MHz, DMSO-$d_6$) δ 5.12 (2H, s), 6.93-7.24 (4H, m), 7.34-7.82 (1H, m), 8.60 (1H, d, J=2.2 Hz), 9.26 (1H, d, J=2.2 Hz), 10.77 (1H, s).

Example 8b

6-[5-(difluoromethyl)-1,3,4-oxadiazol-2-yl]-2-(4-fluorophenyl)-2,3-dimethyl-2,3-dihydro-4H-1,3-benzoxazin-4-one (Optical Isomer 1)

A) 6-bromo-2-(4-fluorophenyl)-2-methyl-2,3-dihydro-4H-1,3-benzoxazin-4-one

To a mixture of 5-bromo-2-hydroxybenzamide (490 mg) and toluene (9.07 ml) were added 1-(4-fluorophenyl)ethanone (627 mg) and 4-methylbenzenesulfonic acid monohydrate (431 mg) at room temperature, and the mixture was stirred overnight at 120° C. To the mixture was added 1N aqueous sodium hydroxide solution at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (364 mg).

1H NMR (400 MHz, CDCl$_3$) δ 1.92 (3H, s), 6.78-7.05 (4H, m), 7.37-7.56 (3H, m), 7.93 (1H, d, J=2.4 Hz).

B) 6-bromo-2-(4-fluorophenyl)-2,3-dimethyl-2,3-dihydro-4H-1,3-benzoxazin-4-one

To a mixture of 6-bromo-2-(4-fluorophenyl)-2-methyl-2,3-dihydro-4H-1,3-benzoxazin-4-one (160 mg) and DMF (1904 μl) were added iodomethane (101 mg) and cesium carbonate (233 mg) at room temperature. The mixture was stirred overnight at room temperature. To the mixture was added water at room temperature. The obtained solid was collected by filtration, and washed with water to give the title compound (129 mg).

1H NMR (400 MHz, DMSO-$d_6$) δ 2.03 (3H, s), 3.17 (3H, s), 6.84-7.05 (1H, m), 7.18 (2H, s), 7.29-7.46 (2H, m), 7.60 (1H, dd, J=8.7, 2.6 Hz), 7.74 (1H, d, J=2.4 Hz).

C) tert-butyl 2-[2-(4-fluorophenyl)-2,3-dimethyl-4-oxo-3,4-dihydro-2H-1,3-benzoxazine-6-carbonyl]hydrazine-1-carboxylate To a mixture of 6-bromo-2-(4-fluorophenyl)-2,3-dimethyl-2,3-dihydro-4H-1,3-benzoxazin-4-one (129 mg) and CPME (10 ml) were added tert-butyl hydrazinecarboxylate (73.0 mg), XANTPHOS (21.32 mg), Pd(dba)2 (212 mg) and N-cyclohexyl-N-methylcyclohexanamine (144 mg) at room temperature. The mixture was stirred under carbon monoxide atmosphere at 90° C. for 5 hr. The impurities were removed by filtration, and the filtrate was concentrated under reduced pressure. The residue was purified by silica gel column chromatography (ethyl acetate/hexane) to give the title compound (133 mg).
MS: [M+H-Boc]$^+$ 330.1.

D) 2-(4-fluorophenyl)-2,3-dimethyl-4-oxo-3,4-dihydro-2H-1,3-benzoxazine-6-carbohydrazide Hydrochloride A mixture of tert-butyl 2-[2-(4-fluorophenyl)-2,3-dimethyl-4-oxo-3,4-dihydro-2H-1,3-benzoxazine-6-carbonyl]hydrazine-1-carboxylate (133 mg) and 4N hydrochloric acid-ethyl acetate (5 ml) was stirred at room temperature for 5 hr. The reaction solution was concentrated under reduced pressure to give the title compound (116 mg).
MS: M+1 330.1.

E) 6-[5-(difluoromethyl)-1,3,4-oxadiazol-2-yl]-2-(4-fluorophenyl)-2,3-dimethyl-2,3-dihydro-4H-1,3-benzoxazin-4-one To a mixture of 2-(4-fluorophenyl)-2,3-dimethyl-4-oxo-3,4-dihydro-2H-1,3-benzoxazine-6-carbohydrazide hydrochloride (116 mg), difluoroacetic anhydride (110 mg) and THF (2 ml) was added TEA (177 µl) at room temperature. The mixture was stirred at room temperature for 2 hr. To the mixture was added saturated brine at room temperature, and the mixture was extracted with ethyl acetate. The organic layer was separated, washed with saturated brine, dried over anhydrous magnesium sulfate, and concentrated under reduced pressure. To a mixture of the obtained residue, 4-methylbenzenesulfonyl chloride (181 mg) and THF (1.27 ml) was added DIPEA (164 mg) at room temperature. The mixture was stirred at 50° C. for 2 hr. To the mixture was added water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (33 mg).
$^1$H NMR (400 MHz, CDCl$_3$) δ 2.08 (3H, s), 3.24 (3H, s), 6.73-6.99 (1H, m), 6.99-7.07 (3H, m), 7.34-7.42 (2H, m), 8.07-8.20 (1H, m), 8.56-8.65 (1H, m).

F) 6-[5-(difluoromethyl)-1,3,4-oxadiazol-2-yl]-2-(4-fluorophenyl)-2,3-dimethyl-2,3-dihydro-4H-1,3-benzoxazin-4-one (Optical Isomer)

6-[5-(Difluoromethyl)-1,3,4-oxadiazol-2-yl]-2-(4-fluorophenyl)-2,3-dimethyl-2,3-dihydro-4H-1,3-benzoxazin-4-one (40 mg) was subjected to optical resolution by chiral HPLC (column: CHIRALCPAK AD-H (DAICEL), 20 mmID×250 mmL, mobile phase: MecOH) to give the title compound with shorter retention time (15.5 mg, 99.9% ee, analysis chiral HPLC (column: CHIRALCPAK AD-H (DAICEL), 4.6 mmID×250 mmL, mobile phase: MeOH, retention time:11.02 min).
$^1$H NMR (400 MHz, CDCl$_3$) δ 1.25-1.29 (3H, m), 2.08 (3H, s), 6.72-6.99 (1H, m), 7.00-7.07 (3H, m), 7.37 (2H, dd, J=8.4, 5.3 Hz), 8.15 (1H, dd, J=8.4, 1.8 Hz), 8.43-8.69 (1H, m).

Example 33b

7-[5-(difluoromethyl)-1,3,4-oxadiazol-2-yl]-3-(4-fluorophenyl)-2-methyl-3,4-dihydroisoquinolin-1(2H)-one A) 2-bromo-5-methoxy-N-methylbenzamide A mixture of 2-bromo-5-methoxybenzoic acid (10 g) and thionyl chloride (40 mL) was refluxed for 1 hr. The mixture was concentrated under reduced pressure, to the residue was added toluene, and the mixture was subjected to azeotropic concentration under reduced pressure. The obtained oil was dissolved in THF (50 mL), and the solution was added dropwise to a mixture of methylamine (2M THF solution, 26 mL), DIPEA (22.7 mL) and THF (100 mL) over 30 min at 0° C. The mixture was stirred at 0° C. for 2 hr, water was added thereto, and the mixture was extracted twice with ethyl acetate. The organic layer was separated, washed with saturated aqueous sodium hydrogencarbonate solution, 1M hydrochloric acid and saturated brine, dried over anhydrous magnesium sulfate, and concentrated under reduced pressure. The residue was crystallized from ethyl acetate/hexane to give the title compound (8.11 g).
$^1$H NMR (400 MHz, DMSO-d$_6$) δ 2.73 (3H, d, J=4.6 Hz), 3.77 (3H, s), 6.91-6.96 (2H, m), 7.51 (1H, d, J=8.7 Hz), 8.30 (1H, br d, J=4.2 Hz).

B) 3-(4-fluorophenyl)-7-methoxy-2-methylisoquinolin-1(2H)-one

A mixture of 2-bromo-5-methoxy-N-methylbenzamide (4.10 g), 1-(4-fluorophenyl)ethanone (3.48 g), copper(I) bromide (0.602 g), cesium carbonate (10.95 g) and DMSO (80 mL) was stirred under nitrogen atmosphere at 100° C. for 15 hr. To the mixture were added water and saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (448 mg).
MS: [M+H]$^+$ 284.1.

C) 3-(4-fluorophenyl)-7-methoxy-2-methyl-3,4-dihydroisoquinolin-1(2H)-one

A mixture of 3-(4-fluorophenyl)-7-methoxy-2-methylisoquinolin-1(2H)-one (448 mg), 10% palladium on carbon (ca. 50% hydrous product, 200 mg) and MeOH (30 mL) was stirred overnight under normal hydrogen atmosphere at 60° C. The catalyst was removed by filtration, the filtrate was concentrated under reduced pressure, and the residue was purified by silica gel column chromatography (ethyl acetate/hexane) to give the title compound (410 mg).
MS: [M+H]$^+$ 286.1.

D) 3-(4-fluorophenyl)-7-hydroxy-2-methyl-3,4-dihydroisoquinolin-1(2H)-one

A mixture of 3-(4-fluorophenyl)-7-methoxy-2-methyl-3,4-dihydroisoquinolin-1(2H)-one (710 mg), aluminium trichloride (830 mg), dodecane-1-thiol (1259 mg) and toluene (20 mL) was stirred at room temperature for 2 hr. To the mixture was added 1N hydrochloric acid at 0° C., and the mixture was extracted with ethyl acetate. The organic layer was separated, washed with saturated brine, dried over anhydrous magnesium sulfate, and concentrated under reduced pressure. The obtained solid was crystallized from ethyl acetate/hexane to give the title compound (587 mg).
MS: [M+H]$^+$ 272.2.

E) 3-(4-fluorophenyl)-2-methyl-1-oxo-1,2,3,4-tetrahydroisoquinolin-7-yl trifluoromethanesulfonate To a mixture of 3-(4-fluorophenyl)-7-hydroxy-2-methyl-3,4-dihydroisoquinolin-1(2H)-one (585 mg) and pyridine (10 mL) was added trifluoromethanesulfonic anhydride (0.656 mL) at 0° C. The mixture was stirred at 0° C. for 2 hr, water was added thereto at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (803 mg).
MS: [M+H]$^+$ 404.1.

F) tert-butyl 2-[3-(4-fluorophenyl)-2-methyl-1-oxo-1,2,3,4-tetrahydroisoquinoline-7-carbonyl]hydrazine-1-carboxylate A mixture of 3-(4-fluorophenyl)-2-methyl-1-oxo-1,2,3,4-tetrahydroisoquinolin-7-yl trifluoromethanesulfonate (591 mg), tert-butyl hydrazinecarboxylate (290 mg), bis(dibenzylideneacetone)palladium(0) (84 mg), XANTPHOS (85 mg), N-cyclohexyl-N-methylcyclohexanamine (0.471 mL) and CPME (40 mL) was stirred under carbon monoxide atmosphere (0.6 MPa), at 100° C. 7.5 hr. The insoluble substance was removed by filtration, and the filtrate was concentrated under reduced pressure. The residue was purified by silica gel column chromatography (NH, ethyl acetate/hexane) to give the title compound (419 mg).
MS: [M−H]$^-$ 412.1.

G) 7-[5-(difluoromethyl)-1,3,4-oxadiazol-2-yl]-3-(4-fluorophenyl)-2-methyl-3,4-dihydroisoquinolin-1(2H)-one A mixture of tert-butyl 2-[3-(4-fluorophenyl)-2-methyl-1-oxo-1,2,3,4-tetrahydroisoquinoline-7-carbonyl]hydrazine-1-carboxylate (417 mg) and 4M hydrogen chloride CPME solution (10 mL) was stirred at room temperature for 1 h, and the reaction solution was concentrated under reduced pressure. The residue was dissolved in THF (10 mL), and DIPEA (0.528 mL) and difluoroacetic anhydride (0.188 mL) were added thereto at 0° C. The mixture was stirred under nitrogen atmosphere at 0° C. for 30 min, and the reaction solution was concentrated under reduced pressure. The residue was dissolved in acetonitrile (10 mL), and DIPEA (0.352 mL) and 4-methylbenzenesulfonyl chloride (385 mg) was added thereto at room temperature. The mixture was stirred under nitrogen atmosphere at room temperature for 45 min, and the reaction solution was concentrated under reduced pressure. The residue was purified by silica gel column chromatography (NH, ethyl acetate/hexane) to give the title compound (250 mg).
$^1$H NMR (400 MHz, DMSO-d$_6$) δ 3.03 (3H, s), 3.21 (1H, dd, J=16.8, 2.3 Hz), 3.75 (1H, dd, J=16.6, 6.8 Hz), 5.09 (1H, dd, J=6.6, 2.2 Hz), 7.09-7.15 (4H, m), 7.38-7.71 (2H, m), 8.08 (1H, dd, J=7.8, 2.0 Hz), 8.53 (1H, d, J=2.0 Hz).

Example 41b

7-[5-(difluoromethyl)-1,3,4-oxadiazol-2-yl]-3-(4-fluorophenyl)-2-methyl-3,4-dihydroisoquinolin-1(2H)-one (Optical Isomer 1)

7-[5-(Difluoromethyl)-1,3,4-oxadiazol-2-yl]-3-(4-fluorophenyl)-2-methyl-3,4-dihydroisoquinolin-1(2H)-one (232.6 mg) was resolved by HPLC (column: CHIRALCEL OJ-H, 20 mmID×250 mmL, mobile phase: EtOH) to give the title compound with shorter retention time (110.0 mg).

Example 42b

7-[5-(difluoromethyl)-1,3,4-oxadiazol-2-yl]-3-(4-fluorophenyl)-2-methyl-3,4-dihydroisoquinolin-1(2H)-one (optical Isomer 2)

7-[5-(Difluoromethyl)-1,3,4-oxadiazol-2-yl]-3-(4-fluorophenyl)-2-methyl-3,4-dihydroisoquinolin-1(2H)-one (232.6 mg) was resolved by HPLC (column: CHIRALCEL OJ-H, 20 mmID×250 mmL, mobile phase: EtOH) to give the title compound with longer retention time (115.5 mg).

The compounds of Examples are shown in the following tables. MS in the tables means actual measured value. The compounds of Example 4b to Example 7b, Example 9b to Example 32b, Example 34b to Example 40b and Example 43b to Example 56b in the following Table 2 were produced according to the methods described in the above-mentioned Examples, or methods analogous thereto.

TABLE 2

| Example | IUPAC name | Structure | MS |
| --- | --- | --- | --- |
| 1b | 3-[5-(difluoromethyl)-1,3,4-oxadiazol-2-yl]-7-(4-fluorophenyl)-6,7-dimethyl-7,8-dihydro-1,6-naphthyridin-5(6H)-one (optical isomer 2) | 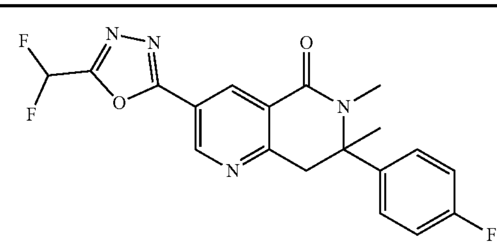 | 389.1 |

TABLE 2-continued

| Example | IUPAC name | Structure | MS |
|---|---|---|---|
| 2b | 7-[5-(difluoromethyl)-1,3,4-oxadiazol-2-yl]-3-(4-fluorophenyl)-3,4-dihydrophthalazin-1(2H)-one | 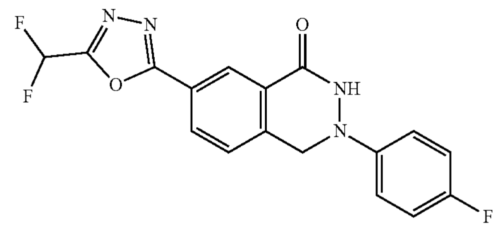 [SMILES: O=C1NN(c2ccc(F)cc2)Cc2ccc(-c3nnc(C(F)F)o3)cc21] | 359.1 |
| 3b | 3-[5-(difluoromethyl)-1,3,4-oxadiazol-2-yl]-7-(4-fluorophenyl)-7,8-dihydropyrido[2,3-d]pyridazin-5(6H)-one | 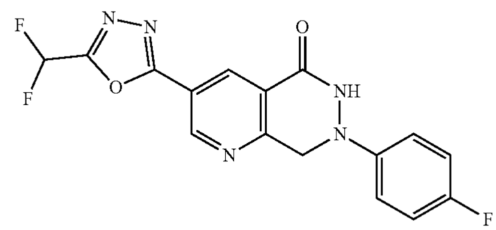 [SMILES: O=C1NN(c2ccc(F)cc2)Cc2ncc(-c3nnc(C(F)F)o3)cc21] | 360.1 |
| 4b | 6-[5-(difluoromethyl)-1,3,4-oxadiazol-2-yl]-2,3-dimethyl-2-phenyl-2,3-dihydro-4H-1,3-benzoxazin-4-one | 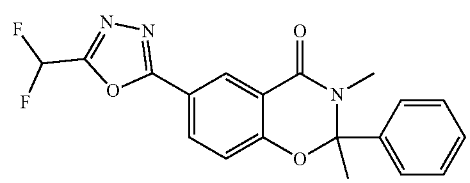 [SMILES: CN1C(=O)c2cc(-c3nnc(C(F)F)o3)ccc2OC1(C)c1ccccc1] | 372.2 |
| 5b | 3-benzyl-6-[5-(difluoromethyl)-1,3,4-oxadiazol-2-yl]-2,3-dihydro-4H-1,3-benzoxazin-4-one | 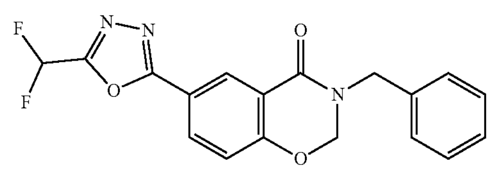 [SMILES: O=C1c2cc(-c3nnc(C(F)F)o3)ccc2OCN1Cc1ccccc1] | 358.1 |
| 6b | (2R)-6-[5-(difluoromethyl)-1,3,4-oxadiazol-2-yl]-2,3-dimethyl-2-phenyl-2,3-dihydro-4H-1,3-benzoxazin-4-one | 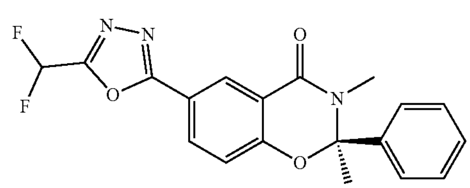 [SMILES: CN1C(=O)c2cc(-c3nnc(C(F)F)o3)ccc2O[C@]1(C)c1ccccc1] | 372.1 |
| 7b | 6-[5-(difluoromethyl)-1,3,4-oxadiazol-2-yl]-2-(4-fluorophenyl)-2,3-dimethyl-2,3-dihydro-4H-1,3-benzoxazin-4-one | 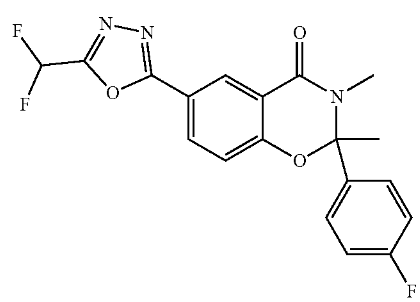 [SMILES: CN1C(=O)c2cc(-c3nnc(C(F)F)o3)ccc2OC1(C)c1ccc(F)cc1] | 390.1 |
| 8b | 6-[5-(difluoromethyl)-1,3,4-oxadiazol-2-yl]-2-(4-fluorophenyl)-2,3-dimethyl-2,3-dihydro-4H-1,3-benzoxazin-4-one (optical isomer 1) | 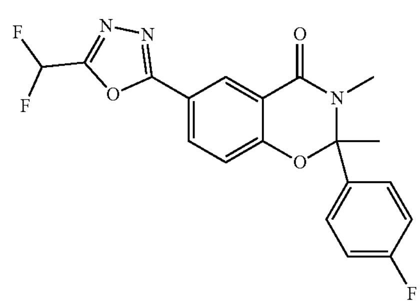 [SMILES: CN1C(=O)c2cc(-c3nnc(C(F)F)o3)ccc2OC1(C)c1ccc(F)cc1] | 390.2 |

TABLE 2-continued

| Example | IUPAC name | Structure | MS |
|---|---|---|---|
| 9b | 6-[5-(difluoromethyl)-1,3,4-oxadiazol-2-yl]-2-(4-fluorophenyl)-2,3-dimethyl-2,3-dihydro-4H-1,3-benzoxazin-4-one (optical isomer 2) | 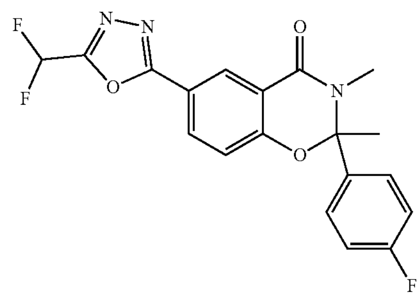 [SMILES: CN1C(=O)c2cc(-c3nnc(C(F)F)o3)ccc2OC1(C)c1ccc(F)cc1] | 390.2 |
| 10b | 7-[5-(difluoromethyl)-1,3,4-oxadiazol-2-yl]-3-(4-fluorophenyl)-2-methyl-3,4-dihydrophthalazin-1(2H)-one | 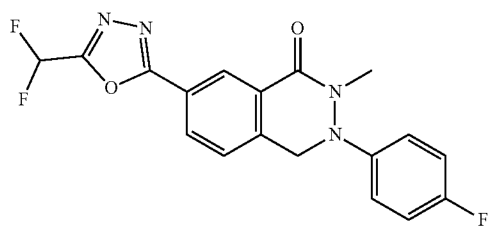 [SMILES: CN1C(=O)c2cc(-c3nnc(C(F)F)o3)ccc2CN1c1ccc(F)cc1] | 375.2 |
| 11b | 3-cyclohexyl-7-[5-(difluoromethyl)-1,3,4-oxadiazol-2-yl]-3,4-dihydrophthalazin-1(2H)-one | 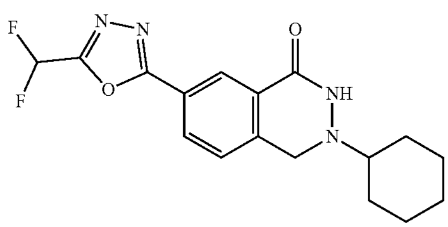 [SMILES: O=C1NN(C2CCCCC2)Cc2ccc(-c3nnc(C(F)F)o3)cc21] | 349.1 |
| 12b | 6-[5-(difluoromethyl)-1,3,4-oxadiazol-2-yl]-2,3-dimethyl-2-(pyridin-2-yl)-2,3-dihydro-4H-1,3-benzoxazin-4-one | 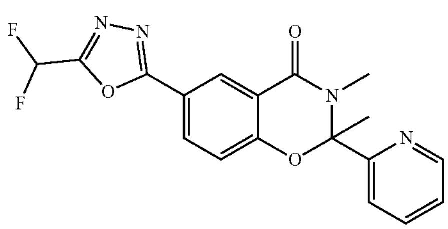 [SMILES: CN1C(=O)c2cc(-c3nnc(C(F)F)o3)ccc2OC1(C)c1ccccn1] | 373.2 |
| 13b | 7-[5-(difluoromethyl)-1,3,4-oxadiazol-2-yl]-3-(4-fluorophenyl)-2,3-dimethyl-3,4-dihydroisoquinolin-1(2H)-one | 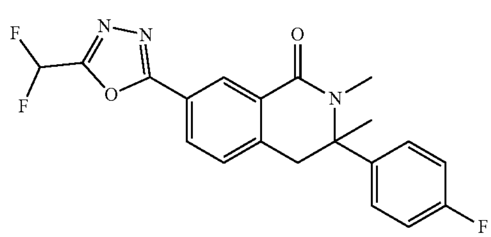 [SMILES: CN1C(=O)c2cc(-c3nnc(C(F)F)o3)ccc2CC1(C)c1ccc(F)cc1] | 388.2 |
| 14b | 2-cyclohexyl-6-[5-(difluoromethyl)-1,3,4-oxadiazol-2-yl]-2,3-dimethyl-2,3-dihydro-4H-1,3-benzoxazin-4-one | 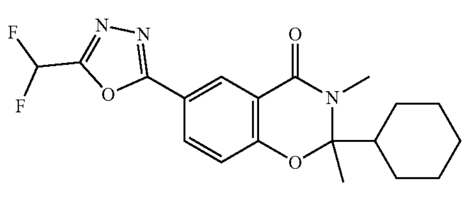 [SMILES: CN1C(=O)c2cc(-c3nnc(C(F)F)o3)ccc2OC1(C)C1CCCCC1] | 378.2 |
| 15b | 7-[5-(difluoromethyl)-1,3,4-oxadiazol-2-yl]-3-(2,2,2-trifluoroethyl)-3,4-dihydrophthalazin-1(2H)-one | 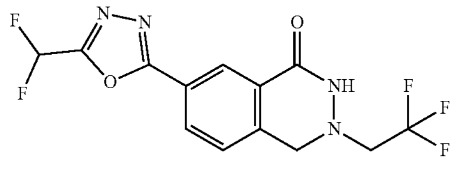 [SMILES: O=C1NN(CC(F)(F)F)Cc2ccc(-c3nnc(C(F)F)o3)cc21] | 347.1 |

TABLE 2-continued

| Example | IUPAC name | Structure | MS |
|---|---|---|---|
| 16b | 2-(2-chlorophenyl)-6-[5-(difluoromethyl)-1,3,4-oxadiazol-2-yl]-2,3-dimethyl-2,3-dihydro-4H-1,3-benzoxazin-4-one | 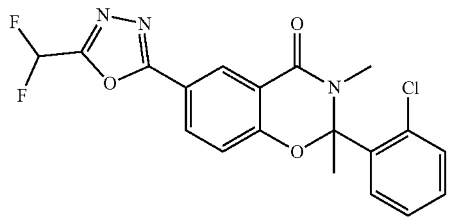 [SMILES: CN1C(=O)c2cc(-c3nnc(C(F)F)o3)ccc2OC1(C)c1ccccc1Cl] | 406.2 |
| 17b | 6-[5-(difluoromethyl)-1,3,4-oxadiazol-2-yl]-2,3-dimethyl-2-[4-(trifluoromethyl)phenyl]-2,3-dihydro-4H-1,3-benzoxazin-4-one | 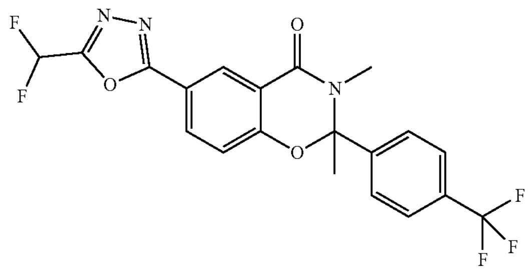 [SMILES: CN1C(=O)c2cc(-c3nnc(C(F)F)o3)ccc2OC1(C)c1ccc(C(F)(F)F)cc1] | 440.2 |
| 18b | 6-[5-(difluoromethyl)-1,3,4-oxadiazol-2-yl]-2-(4-methoxyphenyl)-2,3-dimethyl-2,3-dihydro-4H-1,3-benzoxazin-4-one | 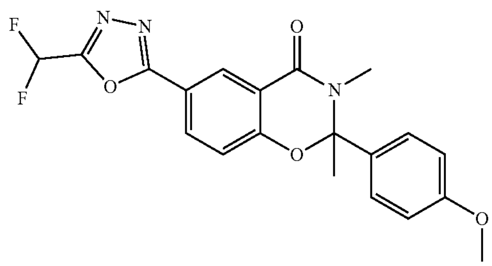 [SMILES: COc1ccc(C2(C)Oc3ccc(-c4nnc(C(F)F)o4)cc3C(=O)N2C)cc1] | 402.3 |
| 19b | 2-(3-chlorophenyl)-6-[5-(difluoromethyl)-1,3,4-oxadiazol-2-yl]-2,3-dimethyl-2,3-dihydro-4H-1,3-benzoxazin-4-one | 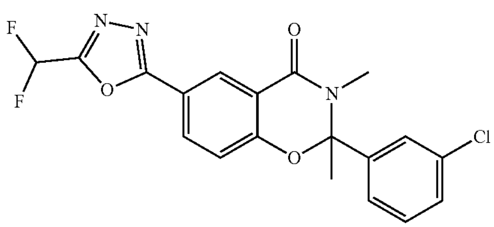 [SMILES: CN1C(=O)c2cc(-c3nnc(C(F)F)o3)ccc2OC1(C)c1cccc(Cl)c1] | 406.1 |
| 20b | 4-{6-[5-(difluoromethyl)-1,3,4-oxadiazol-2-yl]-2,3-dimethyl-4-oxo-3,4-dihydro-2H-1,3-benzoxazin-2-yl}benzonitrile | 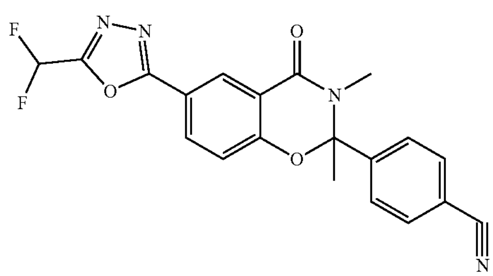 [SMILES: CN1C(=O)c2cc(-c3nnc(C(F)F)o3)ccc2OC1(C)c1ccc(C#N)cc1] | 395.2 |
| 21b | 6-[5-(difluoromethyl)-1,3,4-oxadiazol-2-yl]-2,3-dimethyl-2-[4-(trifluoromethoxy)phenyl]-2,3-dihydro-4H-1,3-benzoxazin-4-one | 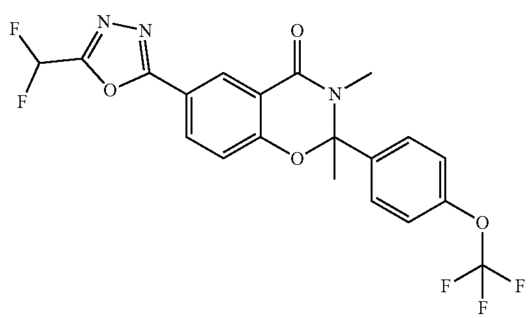 [SMILES: CN1C(=O)c2cc(-c3nnc(C(F)F)o3)ccc2OC1(C)c1ccc(OC(F)(F)F)cc1] | 456.1 |

TABLE 2-continued

| Example | IUPAC name | Structure | MS |
|---|---|---|---|
| 22b | 6-[5-(difluoromethyl)-1,3,4-oxadiazol-2-yl]-2,3-dimethyl-2-(4-methylphenyl)-2,3-dihydro-4H-1,3-benzoxazin-4-one | 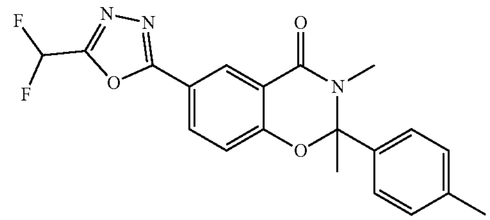 [SMILES: Cc1ccc(C2(C)Oc3ccc(-c4nnc(C(F)F)o4)cc3C(=O)N2C)cc1] | 386.1 |
| 23b | 7-[5-(difluoromethyl)-1,3,4-oxadiazol-2-yl]-3-(4-fluorophenyl)-2,3-dimethyl-3,4-dihydroisoquinolin-1(2H)-one (optical isomer 1) | 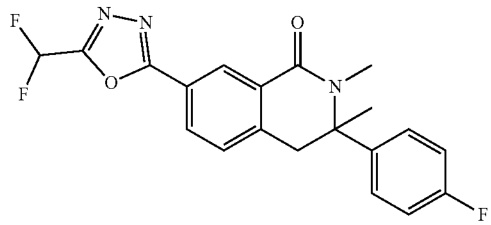 [SMILES: CN1C(=O)c2cc(-c3nnc(C(F)F)o3)ccc2CC1(C)c1ccc(F)cc1] | 388.2 |
| 24b | 7-[5-(difluoromethyl)-1,3,4-oxadiazol-2-yl]-3-(4-fluorophenyl)-2,3-dimethyl-3,4-dihydroisoquinolin-1(2H)-one (optical isomer 2) | 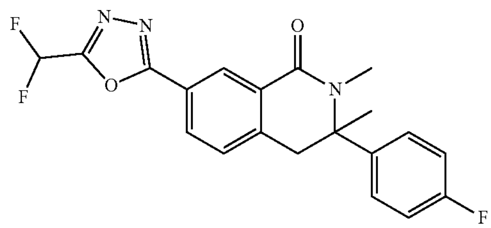 [SMILES: CN1C(=O)c2cc(-c3nnc(C(F)F)o3)ccc2CC1(C)c1ccc(F)cc1] | 388.2 |
| 25b | 3-[5-(difluoromethyl)-1,3,4-oxadiazol-2-yl]-7-(4-fluorophenyl)-6,7-dimethyl-7,8-dihydro-1,6-naphthyridin-5(6H)-one | 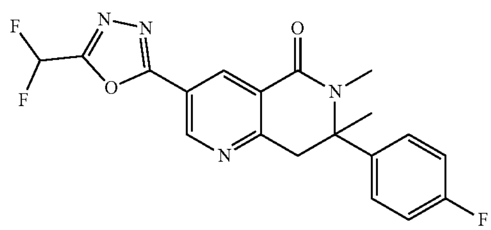 [SMILES: CN1C(=O)c2cc(-c3nnc(C(F)F)o3)cnc2CC1(C)c1ccc(F)cc1] | 389.1 |
| 26b | 2-(4-chlorophenyl)-6-[5-(difluoromethyl)-1,3,4-oxadiazol-2-yl]-2,3-dimethyl-2,3-dihydro-4H-1,3-benzoxazin-4-one | 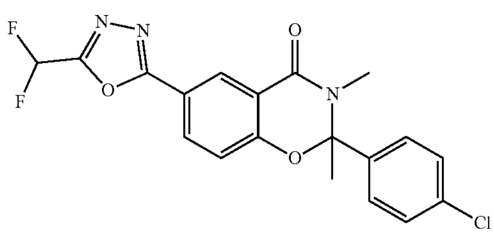 [SMILES: CN1C(=O)c2cc(-c3nnc(C(F)F)o3)ccc2OC1(C)c1ccc(Cl)cc1] | 406.1 |
| 27b | 3-[5-(difluoromethyl)-1,3,4-oxadiazol-2-yl]-7-(4-fluorophenyl)-6,7-dimethyl-7,8-dihydro-1,6-naphthyridin-5(6H)-one (optical isomer 1) | 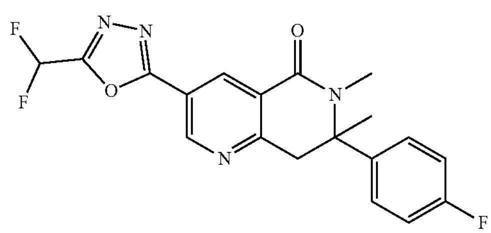 [SMILES: CN1C(=O)c2cc(-c3nnc(C(F)F)o3)cnc2CC1(C)c1ccc(F)cc1] | 389.1 |
| 28b | 7-[5-(difluoromethyl)-1,3,4-oxadiazol-2-yl]-3-(oxan-4-yl)-3,4-dihydrophthalazin-1(2H)-one | 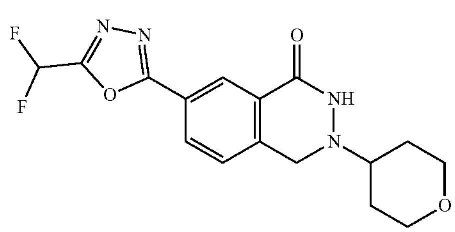 [SMILES: O=C1NN(C2CCOCC2)Cc2ccc(-c3nnc(C(F)F)o3)cc21] | 351.1 |

TABLE 2-continued

| Example | IUPAC name | Structure | MS |
| --- | --- | --- | --- |
| 29b | 3-(4,4-difluorocyclohexyl)-7-[5-(difluoromethyl)-1,3,4-oxadiazol-2-yl]-3,4-dihydrophthalazin-1(2H)-one | 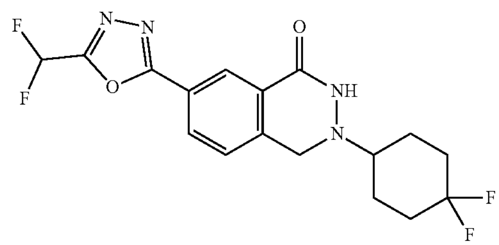 [SMILES: O=C1NN(C2CCC(F)(F)CC2)Cc2ccc(-c3nnc(C(F)F)o3)cc21] | 383.3 |
| 30b | 7-[5-(difluoromethyl)-1,3,4-oxadiazol-2-yl]-3-(3,4-difluorophenyl)-3,4-dihydrophthalazin-1(2H)-one | 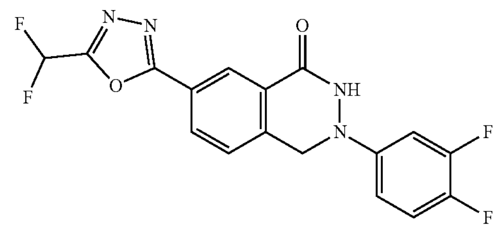 [SMILES: O=C1NN(c2ccc(F)c(F)c2)Cc2ccc(-c3nnc(C(F)F)o3)cc21] | 377.1 |
| 31b | 3-(3-chloro-4-fluorophenyl)-7-[5-(difluoromethyl)-1,3,4-oxadiazol-2-yl]-3,4-dihydrophthalazin-1(2H)-one | 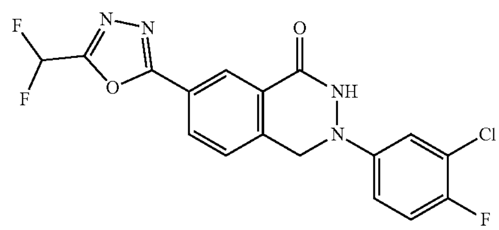 [SMILES: O=C1NN(c2ccc(F)c(Cl)c2)Cc2ccc(-c3nnc(C(F)F)o3)cc21] | 393.1 |
| 32b | 6-[5-(difluoromethyl)-1,3,4-oxadiazol-2-yl]-2-(3,4-difluorophenyl)-2,3-dimethyl-2,3-dihydro-4H-1,3-benzoxazin-4-one | 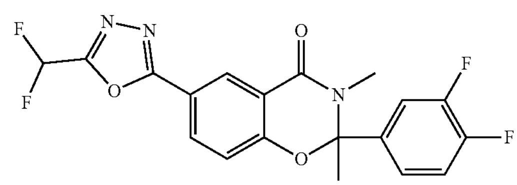 [SMILES: CN1C(=O)c2cc(-c3nnc(C(F)F)o3)ccc2OC1(C)c1ccc(F)c(F)c1] | 408.2 |
| 33b | 7-[5-(difluoromethyl)-1,3,4-oxadiazol-2-yl]-3-(4-fluorophenyl)-2-methyl-3,4-dihydroisoquinolin-1(2H)-one | 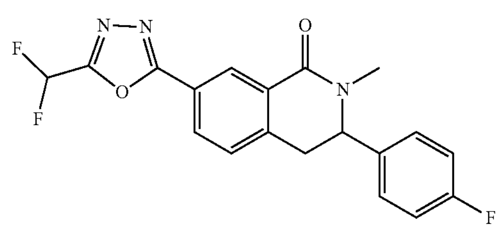 [SMILES: CN1C(=O)c2cc(-c3nnc(C(F)F)o3)ccc2CC1c1ccc(F)cc1] | 374.1 |
| 34b | 3-[5-(difluoromethyl)-1,3,4-oxadiazol-2-yl]-7-(3,4-difluorophenyl)-7,8-dihydropyrido[2,3-d]pyridazin-5(6H)-one | 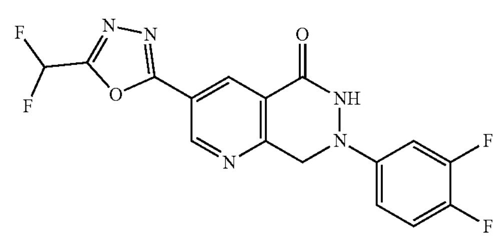 [SMILES: O=C1NN(c2ccc(F)c(F)c2)Cc2ncc(-c3nnc(C(F)F)o3)cc21] | 378.1 |
| 35b | 7-(3-chloro-4-fluorophenyl)-3-[5-(difluoromethyl)-1,3,4-oxadiazol-2-yl]-7,8-dihydropyrido[2,3-d]pyridazin-5(6H)-one | 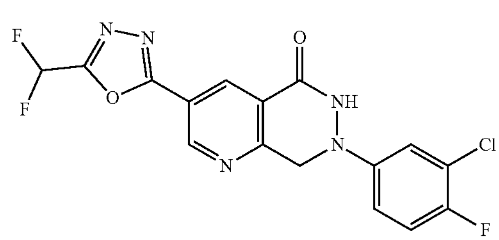 [SMILES: O=C1NN(c2ccc(F)c(Cl)c2)Cc2ncc(-c3nnc(C(F)F)o3)cc21] | 394.1 |

TABLE 2-continued

| Example | IUPAC name | Structure | MS |
|---|---|---|---|
| 36b | 4-{6-[5-(difluoromethyl)-1,3,4-oxadiazol-2-yl]-2,3-dimethyl-4-oxo-3,4-dihydro-2H-1,3-benzoxazin-2-yl}benzonitrile (optical isomer 1) | 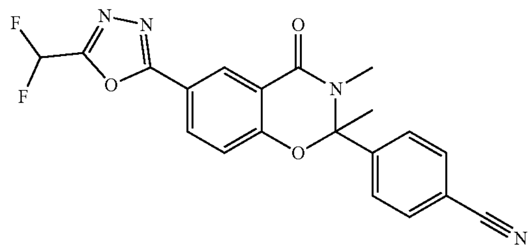 [SMILES: CN1C(=O)c2cc(-c3nnc(C(F)F)o3)ccc2OC1(C)c1ccc(C#N)cc1] | 397.2 |
| 37b | 4-{6-[5-(difluoromethyl)-1,3,4-oxadiazol-2-yl]-2,3-dimethyl-4-oxo-3,4-dihydro-2H-1,3-benzoxazin-2-yl}benzonitrile (optical isomer 2) | 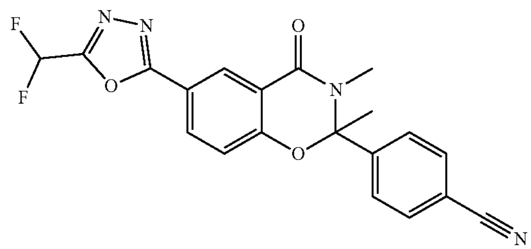 [SMILES: CN1C(=O)c2cc(-c3nnc(C(F)F)o3)ccc2OC1(C)c1ccc(C#N)cc1] | 397.2 |
| 38b | 3-[5-(difluoromethyl)-1,3,4-oxadiazol-2-yl]-7-(3,4-difluorophenyl)-6,7-dimethyl-7,8-dihydro-1,6-naphthyridin-5(6H)-one | 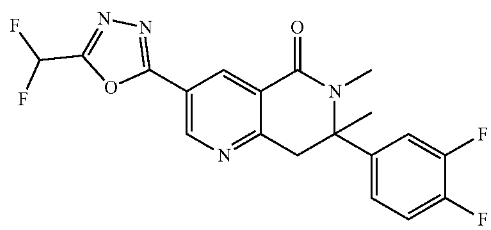 [SMILES: CN1C(=O)c2cc(-c3nnc(C(F)F)o3)cnc2CC1(C)c1ccc(F)c(F)c1] | 407.2 |
| 39b | 3-[5-(difluoromethyl)-1,3,4-oxadiazol-2-yl]-7-(3,4-difluorophenyl)-6,7-dimethyl-7,8-dihydro-1,6-naphthyridin-5(6H)-one (optical isomer 1) | 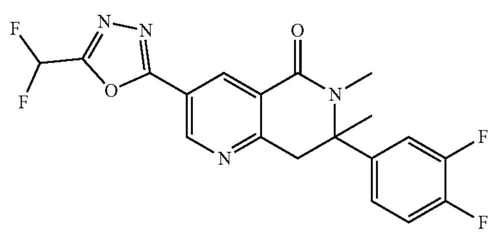 [SMILES: CN1C(=O)c2cc(-c3nnc(C(F)F)o3)cnc2CC1(C)c1ccc(F)c(F)c1] | 407.2 |
| 40b | 3-[5-(difluoromethyl)-1,3,4-oxadiazol-2-yl]-7-(3,4-difluorophenyl)-6,7-dimethyl-7,8-dihydro-1,6-naphthyridin-5(6H)-one (optical isomer 2) | 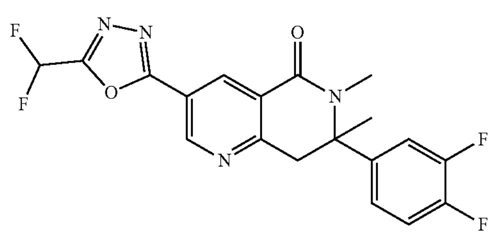 [SMILES: CN1C(=O)c2cc(-c3nnc(C(F)F)o3)cnc2CC1(C)c1ccc(F)c(F)c1] | 407.2 |
| 41b | 7-[5-(difluoromethyl)-1,3,4-oxadiazol-2-yl]-3-(4-fluorophenyl)-2-methyl-3,4-dihydroisoquinolin-1(2H)-one (optical isomer 1) | 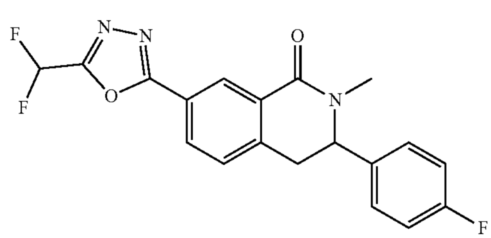 [SMILES: CN1C(=O)c2cc(-c3nnc(C(F)F)o3)ccc2CC1c1ccc(F)cc1] | 374.2 |

TABLE 2-continued

| Example | IUPAC name | Structure | MS |
|---|---|---|---|
| 42b | 7-[5-(difluoromethyl)-1,3,4-oxadiazol-2-yl]-3-(4-fluorophenyl)-2-methyl-3,4-dihydroisoquinolin-1(2H)-one (optical isomer 2) | 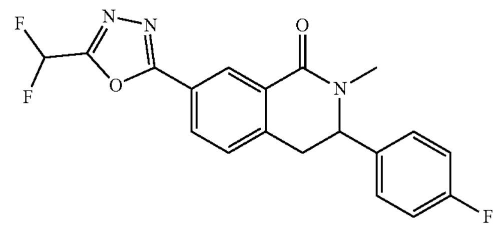 [SMILES: CN1C(=O)c2cc(-c3nnc(C(F)F)o3)ccc2CC1c1ccc(F)cc1] | 374.2 |
| 43b | 6-[5-(difluoromethyl)-1,3,4-oxadiazol-2-yl]-2,3-dimethyl-2-(pyridin-3-yl)-2,3-dihydro-4H-1,3-benzoxazin-4-one | 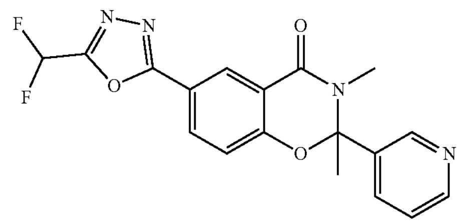 [SMILES: CN1C(=O)c2cc(-c3nnc(C(F)F)o3)ccc2OC1(C)c1cccnc1] | 373.2 |
| 44b | 6-[5-(difluoromethyl)-1,3,4-oxadiazol-2-yl]-2-(4-fluorophenyl)-3-methyl-2,3-dihydro-4H-1,3-benzoxazin-4-one | 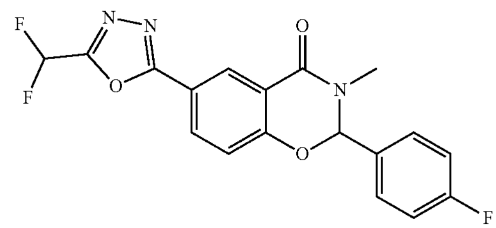 [SMILES: CN1C(=O)c2cc(-c3nnc(C(F)F)o3)ccc2OC1c1ccc(F)cc1] | 376.2 |
| 45b | 6-[5-(difluoromethyl)-1,3,4-oxadiazol-2-yl]-3-ethyl-2-(4-fluorophenyl)-2-methyl-2,3-dihydro-4H-1,3-benzoxazin-4-one | 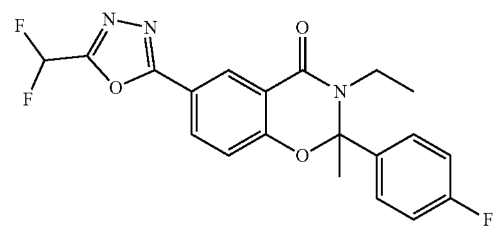 [SMILES: CCN1C(=O)c2cc(-c3nnc(C(F)F)o3)ccc2OC1(C)c1ccc(F)cc1] | 404.2 |
| 46b | 7-[5-(difluoromethyl)-1,3,4-oxadiazol-2-yl]-2-ethyl-3-(4-fluorophenyl)-3,4-dihydrophthalazin-1(2H)-one | 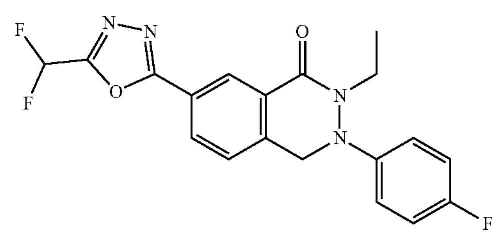 [SMILES: CCN1C(=O)c2cc(-c3nnc(C(F)F)o3)ccc2CN1c1ccc(F)cc1] | 389.3 |
| 47b | 3-(cyclopropylmethyl)-6-[5-(difluoromethyl)-1,3,4-oxadiazol-2-yl]-2-(4-fluorophenyl)-2-methyl-2,3-dihydro-4H-1,3-benzoxazin-4-one | 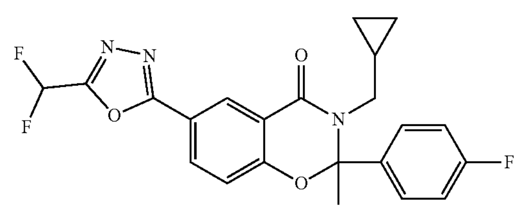 [SMILES: CC1(c2ccc(F)cc2)Oc2ccc(-c3nnc(C(F)F)o3)cc2C(=O)N1CC1CC1] | 430.2 |
| 48b | 2-(2,2-difluoroethyl)-7-[5-(difluoromethyl)-1,3,4-oxadiazol-2-yl]-3-(4-fluorophenyl)-3,4-dihydrophthalazin-1(2H)-one | 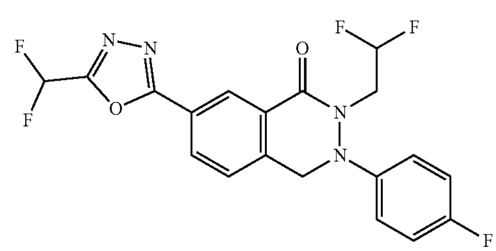 [SMILES: O=C1c2cc(-c3nnc(C(F)F)o3)ccc2CN(c2ccc(F)cc2)N1CC(F)F] | 423.1 |

TABLE 2-continued

| Example | IUPAC name | Structure | MS |
|---|---|---|---|
| 49b | (3S)-7-[5-(difluoromethyl)-1,3,4-oxadiazol-2-yl]-3-(3,4-difluorophenyl)-2,3-dimethyl-3,4-dihydroisoquinolin-1(2H)-one | 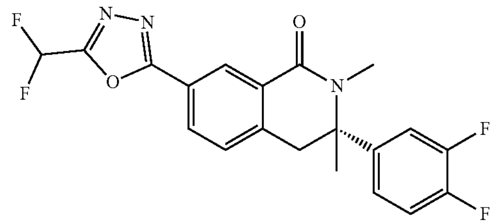 [SMILES: CN1C(=O)c2cc(-c3nnc(C(F)F)o3)ccc2C[C@@]1(C)c1ccc(F)c(F)c1] | 406.3 |
| 50b | (3R)-7-[5-(difluoromethyl)-1,3,4-oxadiazol-2-yl]-3-(3,4-difluorophenyl)-2,3-dimethyl-3,4-dihydroisoquinolin-1(2H)-one | 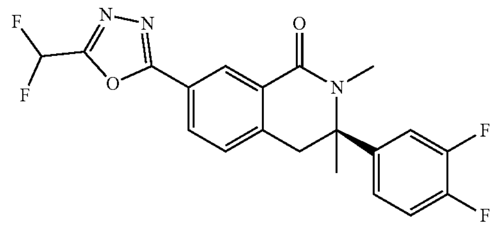 [SMILES: CN1C(=O)c2cc(-c3nnc(C(F)F)o3)ccc2C[C@]1(C)c1ccc(F)c(F)c1] | 406.2 |
| 51b | 6-[5-(difluoromethyl)-1,3,4-oxadiazol-2-yl]-2-(methoxymethyl)-3-methyl-2-phenyl-2,3-dihydro-4H-1,3-benzoxazin-4-one | 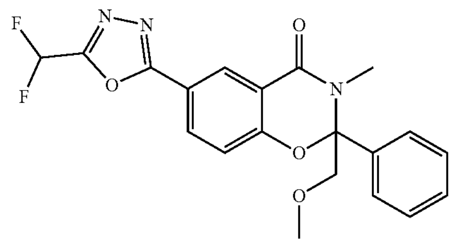 [SMILES: COCC1(c2ccccc2)Oc2ccc(-c3nnc(C(F)F)o3)cc2C(=O)N1C] | 402.3 |
| 52b | 6-[5-(difluoromethyl)-1,3,4-oxadiazol-2-yl]-2-(4-fluorophenyl)-3-(2-methoxyethyl)-2-methyl-2,3-dihydro-4H-1,3-benzoxazin-4-one | 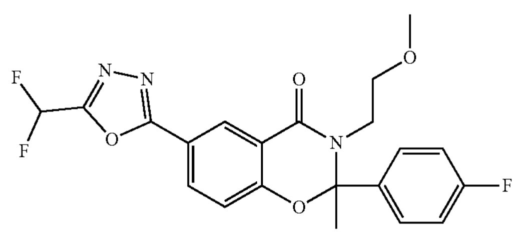 [SMILES: COCCN1C(=O)c2cc(-c3nnc(C(F)F)o3)ccc2OC1(C)c1ccc(F)cc1] | 434.2 |
| 53b | (7R)-3-[5-(difluoromethyl)-1,3,4-oxadiazol-2-yl]-7-(3-fluorophenyl)-6,7-dimethyl-7,8-dihydro-1,6-naphthyridin-5(6H)-one | 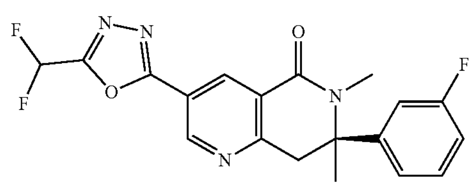 [SMILES: CN1C(=O)c2cc(-c3nnc(C(F)F)o3)cnc2C[C@]1(C)c1cccc(F)c1] | 389.2 |
| 54b | (7S)-6-(2,2-difluoroethyl)-3-[5-(difluoromethyl)-1,3,4-oxadiazol-2-yl]-7-(4-fluorophenyl)-7-methyl-7,8-dihydro-1,6-naphthyridin-5(6H)-one | 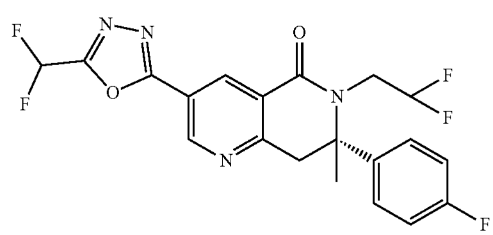 [SMILES: C[C@@]1(c2ccc(F)cc2)Cc2ncc(-c3nnc(C(F)F)o3)cc2C(=O)N1CC(F)F] | 437.2 |
| 55b | (7R)-6-(2,2-difluoroethyl)-3-[5-(difluoromethyl)-1,3,4-oxadiazol-2-yl]-7-(4-fluorophenyl)-7-methyl-7,8-dihydro-1,6-naphthyridin-5(6H)-one | 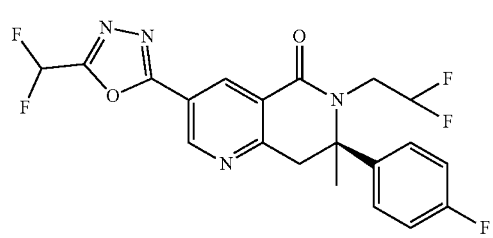 [SMILES: C[C@]1(c2ccc(F)cc2)Cc2ncc(-c3nnc(C(F)F)o3)cc2C(=O)N1CC(F)F] | 437.2 |

TABLE 2-continued

| Example | IUPAC name | Structure | MS |
|---|---|---|---|
| 56b | 3-(2,2-difluoroethyl)-6-[5-(difluoromethyl)-1,3,4-oxadiazol-2-yl]-2-(4-fluorophenyl)-2-methyl-2,3-dihydro-4H-1,3-benzoxazin-4-one | 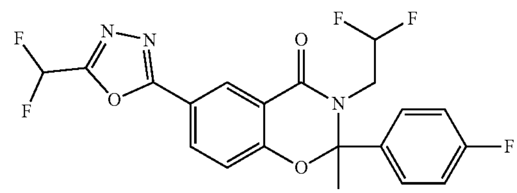 [SMILES: CC1(c2ccc(F)cc2)Oc2ccc(-c3nnc(C(F)F)o3)cc2C(=O)N1CC(F)F] | 440.1 |

Example 1c methyl (6-(5-(difluoromethyl)-1,3,4-oxadiazol-2-yl)-1-oxo-1,3-dihydro-2H-isoindol-2-yl) ((4-fluorophenyl)methyl)carbamate A) tert-butyl 2-(3-(methoxycarbonyl)-4-methylbenzoyl)hydrazinecarboxylate A mixture of methyl 5-bromo-2-methylbenzoate (12.11 g), tert-butyl hydrazinecarboxylate (8.29 g), bis(dibenzylideneacetone)palladium(0) (1.511 g), xantphos (1.512 g), N,N-dicyclohexylmethylamine (15.45 g) and cyclopentyl methyl ether (300 mL) was stirred under carbon monoxide atmosphere (0.5 MPa) at 95° C. for 5 hr. The catalyst was removed by filtration, the filtrate was concentrated under reduced pressure, and the residue was washed with diisopropyl ether. The obtained residue was purified by silica gel column chromatography (NH, ethyl acetate/hexane), and washed with diisopropyl ether and hexane to give the title compound (13.4 g).

MS: [M−H]⁻ 306.9.

B) methyl 5-(hydrazinocarbonyl)-2-methylbenzoate Hydrochloride

To tert-butyl 2-(3-(methoxycarbonyl)-4-methylbenzoyl)hydrazinecarboxylate (13.4 g) was added 4 M hydrogen chloride cyclopentyl methyl ether (200 mL) at room temperature. The mixture was stirred at room temperature for 3 days. The obtained solid was collected by filtration, and dried to give the title compound (10.79 g).

MS: [M+H]⁺ 209.2.

C) methyl 5-(5-(difluoromethyl)-1,3,4-oxadiazol-2-yl)-2-methylbenzoate

To a mixture of methyl 5-(hydrazinocarbonyl)-2-methylbenzoate hydrochloride (1 g) and THF (40 mL) was added DIPEA (3.57 mL) at room temperature. To the reaction mixture was added dropwise difluoroacetic anhydride (0.762 mL) at 0° C. The mixture was stirred at room temperature for 1 hr. To the reaction solution was added 4-methylbenzenesulfonyl chloride (1.558 g) at room temperature, and the mixture was stirred overnight. To the mixture was added water at room temperature, and the mixture was extracted with ethyl acetate. The organic layer was separated, washed with saturated aqueous sodium hydrogencarbonate solution, dried over anhydrous magnesium sulfate, and concentrated under reduced pressure. The residue was purified by silica gel column chromatography (ethyl acetate/hexane) to give the title compound (1.02 g).

MS: [M+H]⁺ 269.1.

D) methyl 2-(bromomethyl)-5-(5-(difluoromethyl)-1,3,4-oxadiazol-2-yl)benzoate

To a mixture of methyl 5-(5-(difluoromethyl)-1,3,4-oxadiazol-2-yl)-2-methylbenzoate (2.8 g) and benzotrifluoride (100 mL) were added NBS (2.79 g) and AIBN (0.171 g) at room temperature. The mixture was stirred under argon atmosphere at 90° C. for 1 hr. To the mixture was added water at room temperature, and the mixture was extracted with ethyl acetate. The organic layer was separated, washed with saturated brine, dried over anhydrous sodium sulfate, and concentrated under reduced pressure. To a mixture of the obtained residue and THF (100 mL) was added DIPEA (2.0 mL). To the mixture was added dropwise diethyl phosphonate (1.48 mL) at 0° C., and the mixture was stirred overnight at room temperature. To the mixture was added water at room temperature, and the mixture was extracted with ethyl acetate. The organic layer was separated, washed with saturated aqueous ammonium chloride solution and saturated brine, dried over anhydrous magnesium sulfate, and concentrated under reduced pressure. The residue was purified by silica gel column chromatography (ethyl acetate/hexane) to give the title compound (3.19 g).

MS: [M+H]⁺ 347.1.

E) tert-butyl (6-(5-(difluoromethyl)-1,3,4-oxadiazol-2-yl)-1-oxo-1,3-dihydro-2H-isoindol-2-yl)carbamate To a mixture of tert-butyl hydrazinecarboxylate (36.2 g), DIPEA (7.17 mL) and MeOH (120 mL) was added dropwise a solution of methyl 2-(bromomethyl)-5-(5-(difluoromethyl)-1,3,4-oxadiazol-2-yl)benzoate (9.5 g) in MeOH (80 mL) at 0° C. The mixture was stirred overnight at room temperature, and the solvent was evaporated under reduced pressure. The residue was partitioned between water and ethyl acetate, and the organic layer was washed with 10% aqueous citric acid solution, saturated aqueous sodium hydrogencarbonate solution and saturated brine, dried over anhydrous sodium sulfate, and concentrated under reduced pressure. The obtained solid was crystallized from diisopropyl ether to give the title compound (7.47 g).

MS: [M+H−Boc]⁺ 311.1.

F) 6-(5-(difluoromethyl)-1,3,4-oxadiazol-2-yl)-2-(((4-fluorophenyl)methyl)amino)-2,3-dihydro-1H-isoindol-1-one To a mixture of tert-butyl (6-(5-(difluoromethyl)-1,3,4-oxadiazol-2-yl)-1-oxo-1,3-dihydro-2H-isoindol-2-yl)carbamate (2.7 g) and TFA (50 mL) was added 4-fluorobenzaldehyde (0.87 mL) at 0° C. The mixture was stirred at room temperature for 10 min. To the mixture was added triethylsilane (2.354 mL) at 0° C., and the mixture was stirred at room temperature for 3 hr. The solvent was evaporated under reduced pressure. The residue was poured into saturated aqueous sodium hydrogencarbonate solution, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (1.61 g).

MS: [M+H]$^+$ 375.1.

G) (6-(5-(difluoromethyl)-1,3,4-oxadiazol-2-yl)-1-oxo-1,3-dihydro-2H-isoindol-2-yl) ((4-fluorophenyl)methyl)carbamoyl chloride To a mixture of 6-(5-(difluoromethyl)-1,3,4-oxadiazol-2-yl)-2-(((4-fluorophenyl)methyl)amino)-2,3-dihydro-1H-isoindol-1-one (900 mg), DIPEA (0.838 mL) and THF (25 mL) was added bis(trichloromethyl) carbonate (856 mg) at 0° C. The mixture was stirred at 0° C. for 10 min, and then at room temperature for 1 hr. The mixture was poured into water, and extracted with ethyl acetate. The organic layer was separated, washed with water and saturated brine, dried over anhydrous sodium sulfate, and concentrated under reduced pressure to give the title compound (999 mg).

MS: [M+H]$^+$ 437.1.

H) methyl (6-(5-(difluoromethyl)-1,3,4-oxadiazol-2-yl)-1-oxo-1,3-dihydro-2H-isoindol-2-yl) ((4-fluorophenyl)methyl)carbamate To a mixture of MeOH (0.046 mL) and DMA (3 mL) was added 1M potassium 2-methylpropan-2-olate THF solution (0.458 mL) at room temperature. The mixture was stirred at room temperature for 10 min. To the mixture was added a solution of (6-(5-(difluoromethyl)-1,3,4-oxadiazol-2-yl)-1-oxo-1,3-dihydro-2H-isoindol-2-yl) ((4-fluorophenyl)methyl)carbamoyl chloride (100 mg) in DMA (1 mL) at room temperature, and the mixture was stirred at room temperature for 3 hr. The mixture was partitioned between water and ethyl acetate, and the organic layer was washed with saturated brine, dried over anhydrous sodium sulfate, and concentrated under reduced pressure. The residue was purified by HPLC (L-Column 2 ODS, mobile phase: water/acetonitrile (containing ammonium bicarbonate)). To the obtained fraction was added water, and the mixture was extracted with ethyl acetate. The organic layer was separated, dried over anhydrous sodium sulfate, and concentrated under reduced pressure to give the title compound (11.7 mg).

$^1$H NMR (400 MHz, CDCl$_3$) δ 3.72-3.96 (4H, m), 4.42-4.67 (2H, m)), 5.12-5.36 (1H, m), 6.78-7.08 (3H, m), 7.33 (2H, dd, J=7.9, 5.5 Hz), 7.52 (1H, d, J=8.1 Hz), 8.36 (1H, dd, J=8.1, 1.2 Hz), 8.58 (1H, d, J=1.0 Hz).

Example 2c 6-(5-(difluoromethyl)-1,3,4-oxadiazol-2-yl)-2-(((4-fluorophenyl)methyl) ((oxan-4-yl)methyl)amino)-2,3-dihydro-1H-isoindol-1-one To a mixture of 6-(5-(difluoromethyl)-1,3,4-oxadiazol-2-yl)-2-(((4-fluorophenyl)methyl)amino)-2,3-dihydro-1H-isoindol-1-one (100 mg) and TFA (3 mL) was added tetrahydro-2H-pyran-4-carbaldehyde (0.056 mL) at room temperature. To the mixture was added triethylsilane (0.171 mL) at room temperature, and the mixture was stirred at room temperature for 3 hr. The mixture was poured into saturated aqueous sodium hydrogencarbonate solution, and extracted with ethyl acetate. The organic layer was separated, washed with water and saturated brine, dried over anhydrous sodium sulfate, and concentrated under reduced pressure. The residue was purified by HPLC (L-Column 2 ODS, mobile phase: water/acetonitrile (containing ammonium bicarbonate)). To the obtained fraction was added water, and the mixture was extracted with ethyl acetate. The organic layer was separated, dried over anhydrous sodium sulfate, and concentrated under reduced pressure to give the title compound (61.3 mg).

$^1$H NMR (400 MHz, DMSO-d$_6$) δ 1.00-1.20 (2H, m), 1.49-1.65 (1H, m), 1.68-1.91 (2H, m), 2.96 (2H, br d, J=5.6 Hz), 3.08-3.27 (2H, m), 3.79 (2H, br dd, J=11.2, 2.2 Hz), 4.19 (2H, br s), 4.45 (2H, br s), 7.04-7.16 (2H, m), 7.34-7.71 (3H, m), 7.77 (1H, d, J=7.8 Hz), 8.17 (1H, d, J=1.0 Hz), 8.25 (1H, dd, J=7.8, 1.7 Hz).

The compounds of Examples are shown in the following tables. MS in the tables means actual measured value. The compounds of Example 3c to Example 19c, Example 21c to Example 66c and Example 68c to Example 71c in the following Table 3 were produced according to the methods described in the above-mentioned Examples, or methods analogous thereto.

TABLE 3

| Example | IUPAC name | Structure | MS |
| --- | --- | --- | --- |
| 1c | methyl {6-[5-(difluoromethyl)-1,3,4-oxadiazol-2-yl]-1-oxo-1,3-dihydro-2H-isoindol-2-yl}[(4-fluorophenyl)methyl]carbamate | 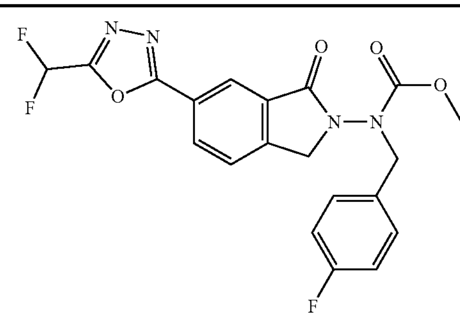 | 433.1 |

TABLE 3-continued

| Example | IUPAC name | Structure | MS |
|---|---|---|---|
| 2c | 6-[5-(difluoromethyl)-1,3,4-oxadiazol-2-yl]-2-{[(4-fluorophenyl)methyl][(oxan-4-yl)methyl]amino}-2,3-dihydro-1H-isoindol-1-one | 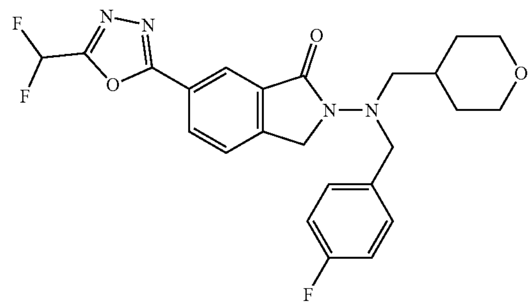 [SMILES: O=C1c2cc(-c3nnc(C(F)F)o3)ccc2CN1N(Cc1ccc(F)cc1)CC1CCOCC1] | 473.2 |
| 3c | tert-butyl {6-[5-(difluoromethyl)-1,3,4-oxadiazol-2-yl]-1-oxo-1,3-dihydro-2H-isoindol-2-yl}carbamate | 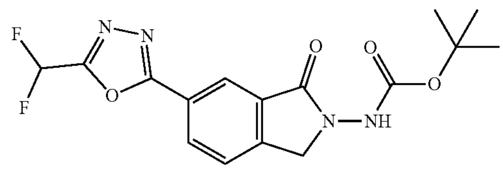 [SMILES: CC(C)(C)OC(=O)NN1Cc2ccc(-c3nnc(C(F)F)o3)cc2C1=O] | 365.1 |
| 4c | tert-butyl benzyl {6-[5-(difluoromethyl)-1,3,4-oxadiazol-2-yl]-1-oxo-1,3-dihydro-2H-isoindol-2-yl}carbamate | 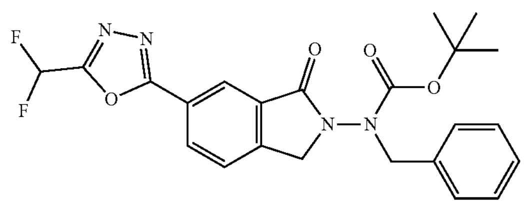 [SMILES: CC(C)(C)OC(=O)N(Cc1ccccc1)N1Cc2ccc(-c3nnc(C(F)F)o3)cc2C1=O] | 454.9 |
| 5c | tert-butyl {6-[5-(difluoromethyl)-1,3,4-oxadiazol-2-yl]-1-oxo-1,3-dihydro-2H-isoindol-2-yl}(2-methylpropyl)carbamate | 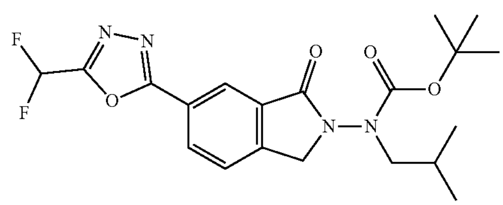 [SMILES: CC(C)CN(C(=O)OC(C)(C)C)N1Cc2ccc(-c3nnc(C(F)F)o3)cc2C1=O] | 420.9 |
| 6c | 6-[5-(difluoromethyl)-1,3,4-oxadiazol-2-yl]-2-{[(4-fluorophenyl)methyl]amino}-2,3-dihydro-1H-isoindol-1-one | 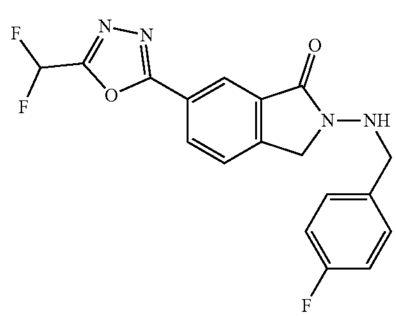 [SMILES: O=C1c2cc(-c3nnc(C(F)F)o3)ccc2CN1NCc1ccc(F)cc1] | 375.2 |
| 7c | 2-{bis[(4-fluorophenyl)methyl]amino}-6-[5-(difluoromethyl)-1,3,4-oxadiazol-2-yl]-2,3-dihydro-1H-isoindol-1-one | 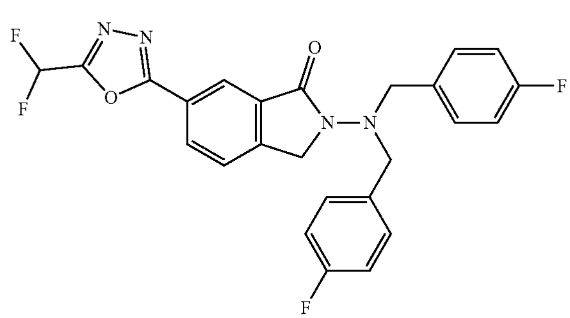 [SMILES: O=C1c2cc(-c3nnc(C(F)F)o3)ccc2CN1N(Cc1ccc(F)cc1)Cc1ccc(F)cc1] | 483.2 |

TABLE 3-continued

| Example | IUPAC name | Structure | MS |
|---|---|---|---|
| 8c | 2-[benzyl (ethyl)amino]-6-[5-(difluoromethyl)-1,3,4-oxadiazol-2-yl]-2,3-dihydro-1H-isoindol-1-one | 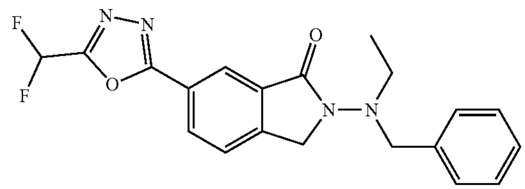 [SMILES: CCN(Cc1ccccc1)N1Cc2ccc(-c3nnc(C(F)F)o3)cc2C1=O] | 385.2 |
| 9c | 2-{[(1-cyclopropyl-1H-pyrazol-4-yl)methyl]amino}-6-[5-(difluoromethyl)-1,3,4-oxadiazol-2-yl]-2,3-dihydro-1H-isoindol-1-one | 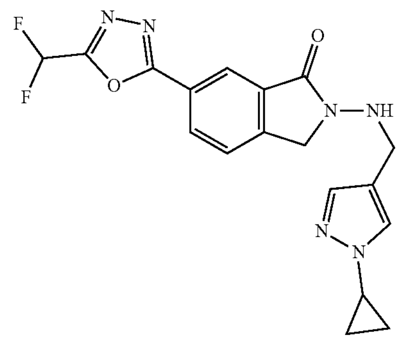 [SMILES: O=C1c2cc(-c3nnc(C(F)F)o3)ccc2CN1NCc1cnn(C2CC2)c1] | 387.1 |
| 10c | 2-{bis[(1-cyclopropyl-1H-pyrazol-4-yl)methyl]amino}-6-[5-(difluoromethyl)-1,3,4-oxadiazol-2-yl]-2,3-dihydro-1H-isoindol-1-one | 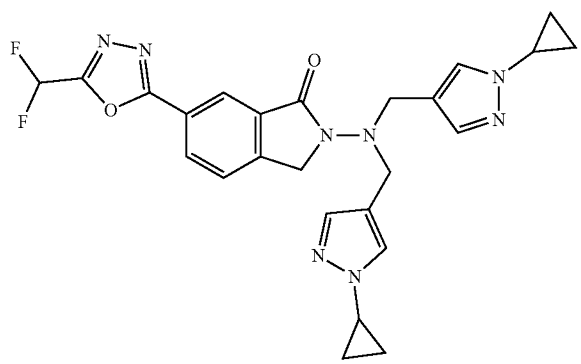 [SMILES: O=C1c2cc(-c3nnc(C(F)F)o3)ccc2CN1N(Cc1cnn(C2CC2)c1)Cc1cnn(C2CC2)c1] | 507.1 |
| 11c | 2-methoxyethyl {6-[5-(difluoromethyl)-1,3,4-oxadiazol-2-yl]-1-oxo-1,3-dihydro-2H-isoindol-2-yl}[(4-fluorophenyl)methyl]carbamate | 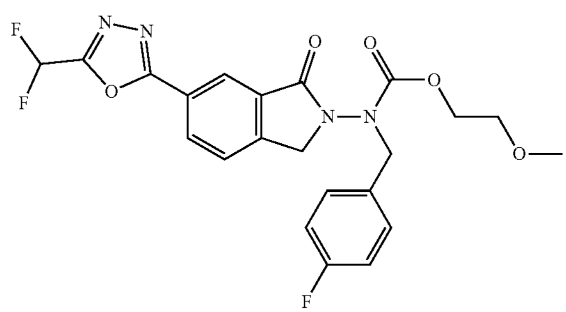 [SMILES: COCCOC(=O)N(Cc1ccc(F)cc1)N1Cc2ccc(-c3nnc(C(F)F)o3)cc2C1=O] | 477.1 |
| 12c | N-[(1-cyclopropyl-1H-pyrazol-4-yl)methyl]-N-{6-[5-(difluoromethyl)-1,3,4-oxadiazol-2-yl]-1-oxo-1,3-dihydro-2H-isoindol-2-yl}-3,3,3-trifluoropropanamide | 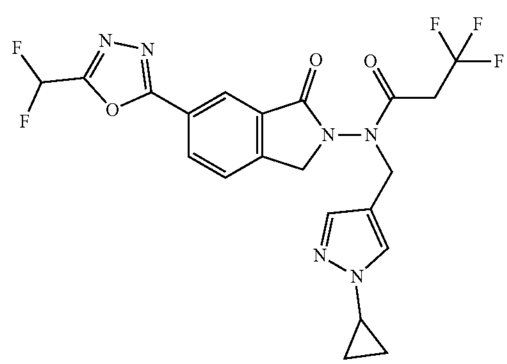 [SMILES: O=C(CC(F)(F)F)N(Cc1cnn(C2CC2)c1)N1Cc2ccc(-c3nnc(C(F)F)o3)cc2C1=O] | 497.1 |

TABLE 3-continued

| Example | IUPAC name | Structure | MS |
| --- | --- | --- | --- |
| 13c | 2,2-difluoroethyl [(1-cyclopropyl-1H-pyrazol-4-yl)methyl]{6-[5-(difluoromethyl)-1,3,4-oxadiazol-2-yl]-1-oxo-1,3-dihydro-2H-isoindol-2-yl}carbamate | 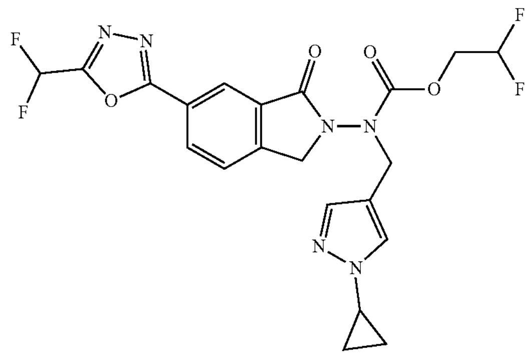 [SMILES: O=C(OCC(F)F)N(Cc1cnn(C2CC2)c1)N1Cc2ccc(-c3nnc(C(F)F)o3)cc2C1=O] | 495.1 |
| 14c | N-{6-[5-(difluoromethyl)-1,3,4-oxadiazol-2-yl]-1-oxo-1,3-dihydro-2H-isoindol-2-yl}-3,3,3-trifluoro-N-[(4-fluorophenyl)methyl]propanamide | 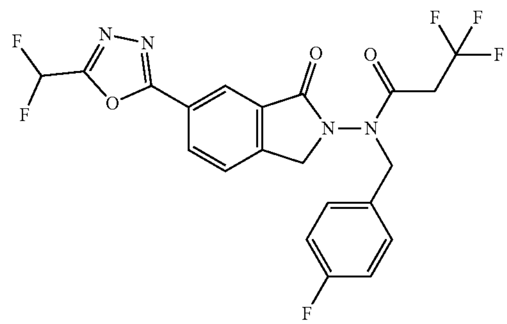 [SMILES: O=C(CC(F)(F)F)N(Cc1ccc(F)cc1)N1Cc2ccc(-c3nnc(C(F)F)o3)cc2C1=O] | 483.2 |
| 15c | 6-[5-(difluoromethyl)-1,3,4-oxadiazol-2-yl]-2-{[(5-fluoropyridin-2-yl)methyl]amino}-2,3-dihydro-1H-isoindol-1-one | 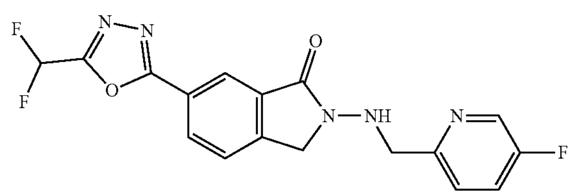 [SMILES: O=C1c2cc(-c3nnc(C(F)F)o3)ccc2CN1NCc1ccc(F)cn1] | 376.1 |
| 16c | 2,2-difluoroethyl {6-[5-(difluoromethyl)-1,3,4-oxadiazol-2-yl]-1-oxo-1,3-dihydro-2H-isoindol-2-yl}[(4-fluorophenyl)methyl]carbamate | 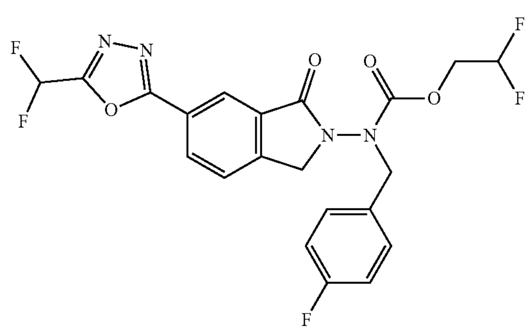 [SMILES: O=C(OCC(F)F)N(Cc1ccc(F)cc1)N1Cc2ccc(-c3nnc(C(F)F)o3)cc2C1=O] | 483.1 |
| 17c | 6-[5-(difluoromethyl)-1,3,4-oxadiazol-2-yl]-2-{[(oxan-4-yl)methyl]amino}-2,3-dihydro-1H-isoindol-1-one | 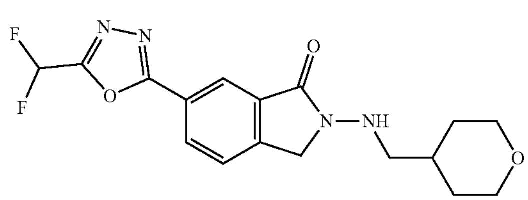 [SMILES: O=C1c2cc(-c3nnc(C(F)F)o3)ccc2CN1NCC1CCOCC1] | 365.2 |

TABLE 3-continued

| Example | IUPAC name | Structure | MS |
|---|---|---|---|
| 18c | 2-{bis[(oxan-4-yl)methyl]amino}-6-[5-(difluoromethyl)-1,3,4-oxadiazol-2-yl]-2,3-dihydro-1H-isoindol-1-one | 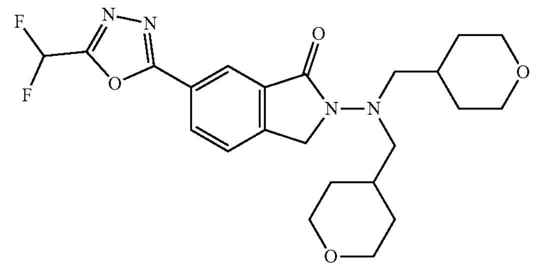 [SMILES: O=C1c2cc(-c3nnc(C(F)F)o3)ccc2CN1N(CC1CCOCC1)CC1CCOCC1] | 463.2 |
| 19c | 6-[5-(difluoromethyl)-1,3,4-oxadiazol-2-yl]-2-{[2-(2,4-difluorophenyl)ethyl]amino}-2,3-dihydro-1H-isoindol-1-one | 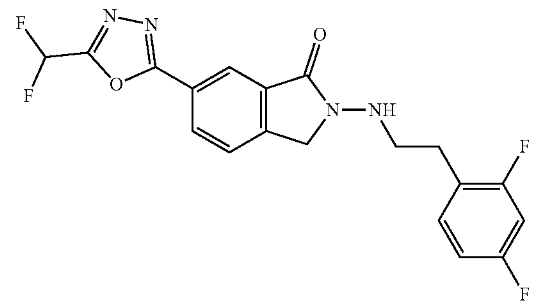 [SMILES: O=C1c2cc(-c3nnc(C(F)F)o3)ccc2CN1NCCc1ccc(F)cc1F] | 407.1 |
| 21c | 6-[5-(difluoromethyl)-1,3,4-oxadiazol-2-yl]-2-{[(4-fluorophenyl)methyl][2-(oxan-4-yl)ethyl]amino}-2,3-dihydro-1H-isoindol-1-one | 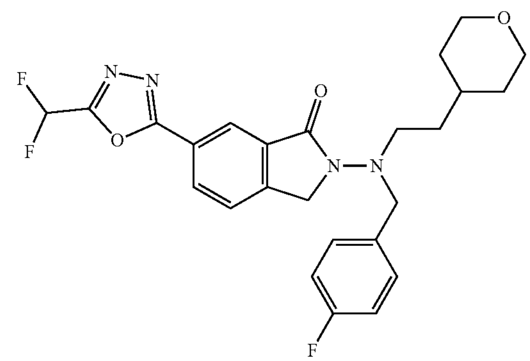 [SMILES: O=C1c2cc(-c3nnc(C(F)F)o3)ccc2CN1N(CCC1CCOCC1)Cc1ccc(F)cc1] | 487.2 |
| 22c | 6-[5-(difluoromethyl)-1,3,4-oxadiazol-2-yl]-2-{[1-(4-fluorophenyl)ethyl]amino}-2,3-dihydro-1H-isoindol-1-one | 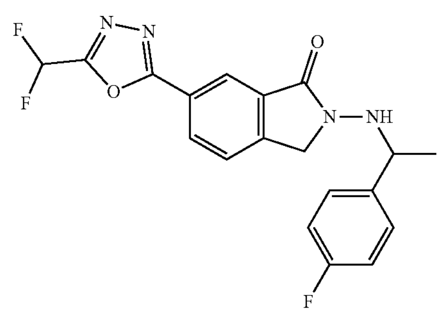 [SMILES: CC(NN1Cc2ccc(-c3nnc(C(F)F)o3)cc2C1=O)c1ccc(F)cc1] | 387.1 |
| 23c | oxan-4-yl {6-[5-(difluoromethyl)-1,3,4-oxadiazol-2-yl]-1-oxo-1,3-dihydro-2H-isoindol-2-yl}[(4-fluorophenyl)methyl]carbamate | 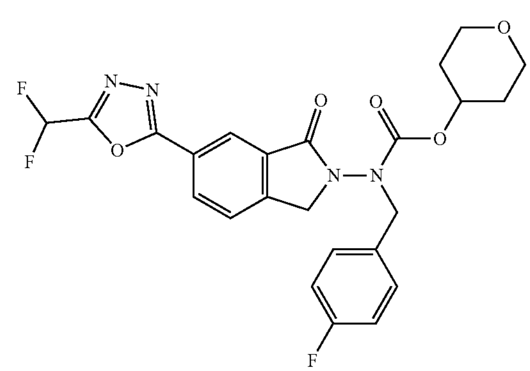 [SMILES: O=C(OC1CCOCC1)N(Cc1ccc(F)cc1)N1Cc2ccc(-c3nnc(C(F)F)o3)cc2C1=O] | 501.2 |

TABLE 3-continued

| Example | IUPAC name | Structure | MS |
|---|---|---|---|
| 24c | 3-methoxycyclohexyl {6-[5-(difluoromethyl)-1,3,4-oxadiazol-2-yl]-1-oxo-1,3-dihydro-2H-isoindol-2-yl}[(4-fluorophenyl)methyl]carbamate | 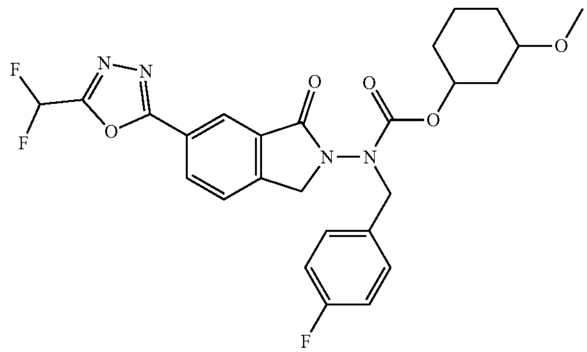 [SMILES: COC1CCCC(OC(=O)N(Cc2ccc(F)cc2)N2Cc3ccc(-c4nnc(C(F)F)o4)cc3C2=O)C1] | 531.2 |
| 25c | (pyridin-2-yl)methyl {6-[5-(difluoromethyl)-1,3,4-oxadiazol-2-yl]-1-oxo-1,3-dihydro-2H-isoindol-2-yl}[(4-fluorophenyl)methyl]carbamate | 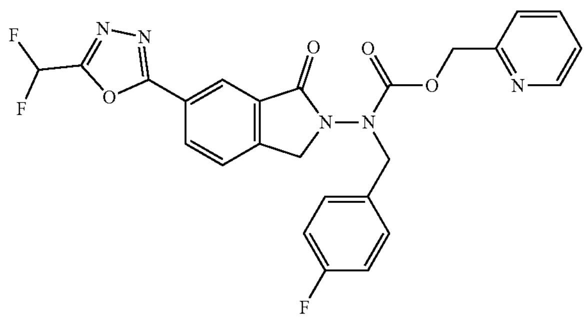 [SMILES: O=C(OCc1ccccn1)N(Cc1ccc(F)cc1)N1Cc2ccc(-c3nnc(C(F)F)o3)cc2C1=O] | 510.1 |
| 26c | oxolan-3-yl {6-[5-(difluoromethyl)-1,3,4-oxadiazol-2-yl]-1-oxo-1,3-dihydro-2H-isoindol-2-yl}[(4-fluorophenyl)methyl]carbamate | 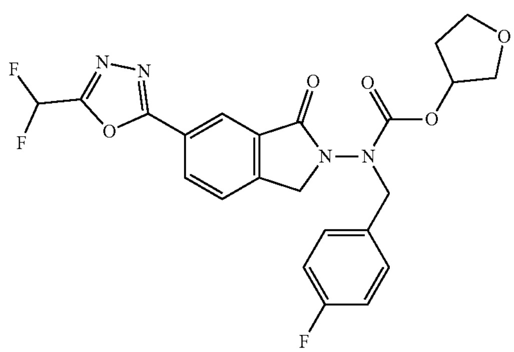 [SMILES: O=C(OC1CCOC1)N(Cc1ccc(F)cc1)N1Cc2ccc(-c3nnc(C(F)F)o3)cc2C1=O] | 489.1 |
| 27c | N-{6-[5-(difluoromethyl)-1,3,4-oxadiazol-2-yl]-1-oxo-1,3-dihydro-2H-isoindol-2-yl}-N-[(4-fluorophenyl)methyl]ethanesulfonamide | 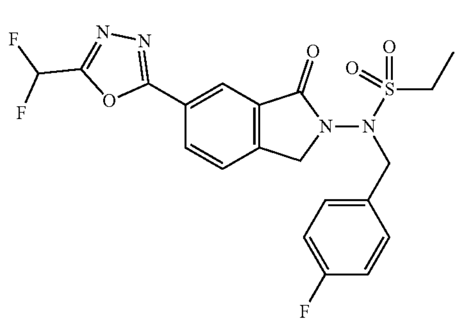 [SMILES: CCS(=O)(=O)N(Cc1ccc(F)cc1)N1Cc2ccc(-c3nnc(C(F)F)o3)cc2C1=O] | 467.2 |

TABLE 3-continued

| Example | IUPAC name | Structure | MS |
|---|---|---|---|
| 28c | 6-[5-(difluoromethyl)-1,3,4-oxadiazol-2-yl]-2-{[(4-fluorophenyl)methyl](methyl)amino}-2,3-dihydro-1H-isoindol-1-one | 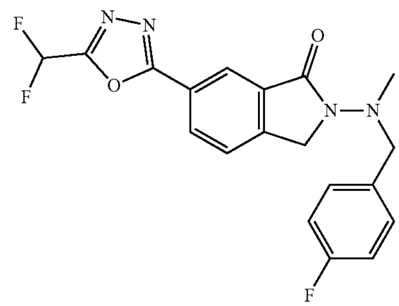 [SMILES: CN(Cc1ccc(F)cc1)N1Cc2ccc(-c3nnc(C(F)F)o3)cc2C1=O] | 389.2 |
| 29c | 2-(cyclohexylamino)-6-[5-(difluoromethyl)-1,3,4-oxadiazol-2-yl]-2,3-dihydro-1H-isoindol-1-one | 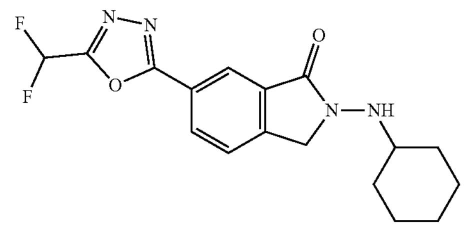 [SMILES: O=C1c2cc(-c3nnc(C(F)F)o3)ccc2CN1NC1CCCCC1] | 349.1 |
| 30c | 6-[5-(difluoromethyl)-1,3,4-oxadiazol-2-yl]-2-(4-fluoroanilino)-2,3-dihydro-1H-isoindol-1-one | 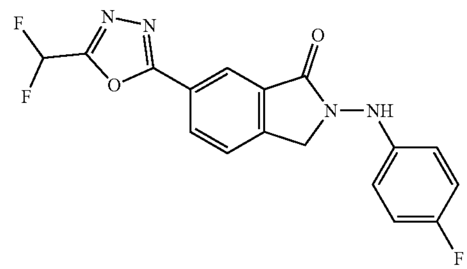 [SMILES: O=C1c2cc(-c3nnc(C(F)F)o3)ccc2CN1Nc1ccc(F)cc1] | 359.2 |
| 31c | 6-[5-(difluoromethyl)-1,3,4-oxadiazol-2-yl]-2-[(2,2,2-trifluoroethyl)amino]-2,3-dihydro-1H-isoindol-1-one | 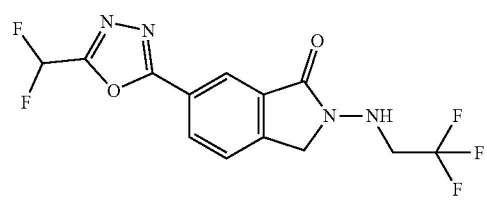 [SMILES: O=C1c2cc(-c3nnc(C(F)F)o3)ccc2CN1NCC(F)(F)F] | 347.1 |
| 32c | 6-[5-(difluoromethyl)-1,3,4-oxadiazol-2-yl]-2-(pentafluoroanilino)-2,3-dihydro-1H-isoindol-1-one | 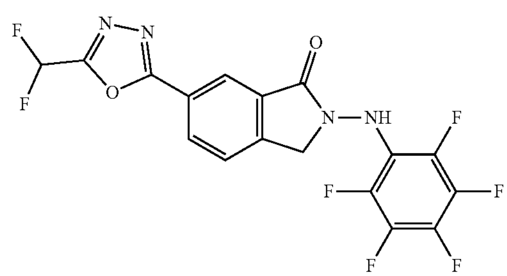 [SMILES: O=C1c2cc(-c3nnc(C(F)F)o3)ccc2CN1Nc1c(F)c(F)c(F)c(F)c1F] | 431.1 |
| 33c | 3-[5-(difluoromethyl)-1,3,4-oxadiazol-2-yl]-6-(pentafluoroanilino)-6,7-dihydro-5H-pyrrolo[3,4-b]pyridin-5-one | 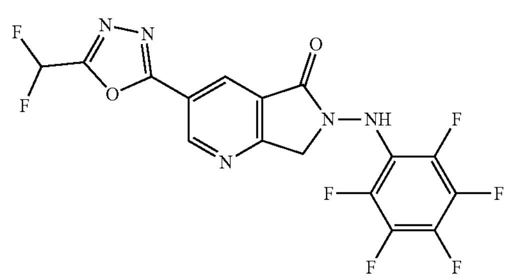 [SMILES: O=C1c2cc(-c3nnc(C(F)F)o3)cnc2CN1Nc1c(F)c(F)c(F)c(F)c1F] | 432.2 |

TABLE 3-continued

| Example | IUPAC name | Structure | MS |
|---------|-----------|-----------|-----|
| 34c | 6-[5-(difluoromethyl)-1,3,4-oxadiazol-2-yl]-2-[(oxan-4-yl)amino]-2,3-dihydro-1H-isoindol-1-one | 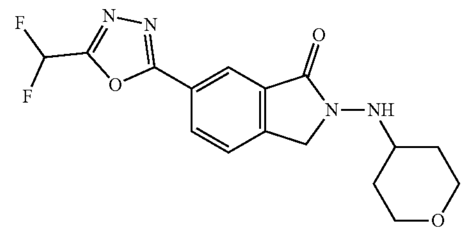 [SMILES: O=C1c2cc(-c3nnc(C(F)F)o3)ccc2CN1NC1CCOCC1] | 351.2 |
| 35c | 2-[(4,4-difluorocyclohexyl)amino]-6-[5-(difluoromethyl)-1,3,4-oxadiazol-2-yl]-2,3-dihydro-1H-isoindol-1-one | 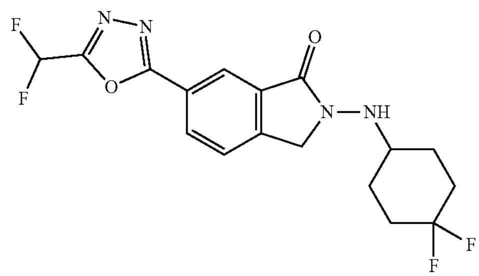 [SMILES: O=C1c2cc(-c3nnc(C(F)F)o3)ccc2CN1NC1CCC(F)(F)CC1] | 383.3 |
| 36c | 2-(3,4-difluoroanilino)-6-[5-(difluoromethyl)-1,3,4-oxadiazol-2-yl]-2,3-dihydro-1H-isoindol-1-one | 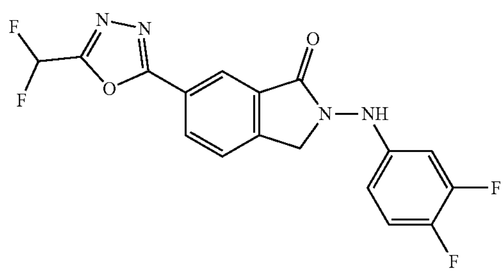 [SMILES: O=C1c2cc(-c3nnc(C(F)F)o3)ccc2CN1Nc1ccc(F)c(F)c1] | 377.2 |
| 37c | 2-(3-chloro-4-fluoroanilino)-6-[5-(difluoromethyl)-1,3,4-oxadiazol-2-yl]-2,3-dihydro-1H-isoindol-1-one | 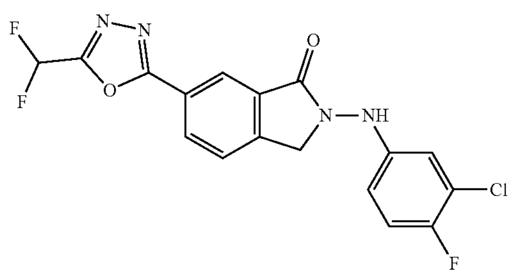 [SMILES: O=C1c2cc(-c3nnc(C(F)F)o3)ccc2CN1Nc1ccc(F)c(Cl)c1] | 393.1 |
| 38c | tert-butyl {6-[5-(difluoromethyl)-1,3,4-oxadiazol-2-yl]-1-oxo-1,3-dihydro-2H-isoindol-2-yl}methylcarbamate | 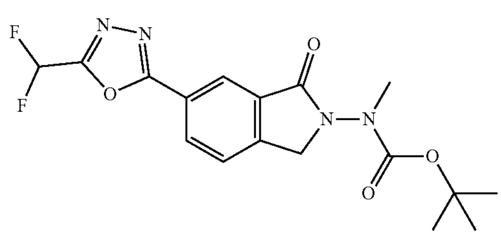 [SMILES: CN(C(=O)OC(C)(C)C)N1Cc2ccc(-c3nnc(C(F)F)o3)cc2C1=O] | 379.2 |
| 39c | 6-[5-(difluoromethyl)-1,3,4-oxadiazol-2-yl]-2-[(5-fluoropyridin-2-yl)amino]-2,3-dihydro-1H-isoindol-1-one | 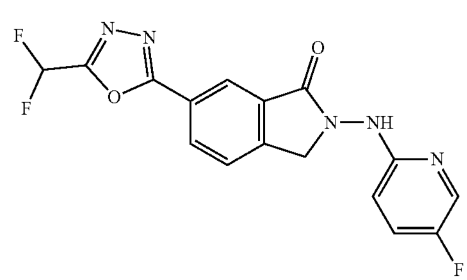 [SMILES: O=C1c2cc(-c3nnc(C(F)F)o3)ccc2CN1Nc1ccc(F)cn1] | 362.2 |

TABLE 3-continued

| Example | IUPAC name | Structure | MS |
|---|---|---|---|
| 40c | 6-[5-(difluoromethyl)-1,3,4-oxadiazol-2-yl]-2-{[(3,4-difluorophenyl)methyl](methyl)amino}-2,3-dihydro-1H-isoindol-1-one | 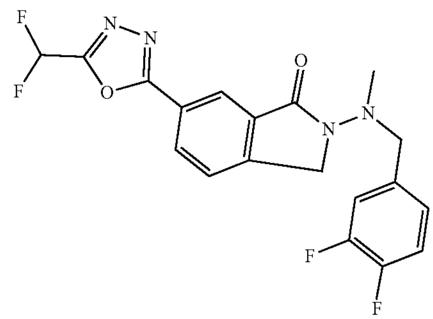 [SMILES: CN(Cc1ccc(F)c(F)c1)N1Cc2ccc(-c3nnc(C(F)F)o3)cc2C1=O] | 407.2 |
| 41c | 6-[5-(difluoromethyl)-1,3,4-oxadiazol-2-yl]-2-{methyl[(oxan-4-yl)methyl]amino}-2,3-dihydro-1H-isoindol-1-one | 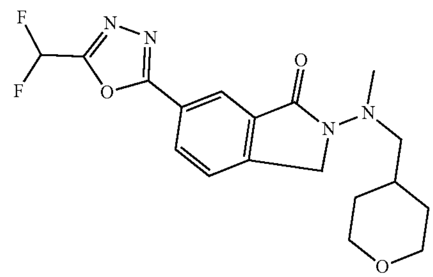 [SMILES: CN(CC1CCOCC1)N1Cc2ccc(-c3nnc(C(F)F)o3)cc2C1=O] | 379.3 |
| 42c | 2-{[(5-chloro-2-hydroxyphenyl)methyl](methyl)amino}-6-[5-(difluoromethyl)-1,3,4-oxadiazol-2-yl]-2,3-dihydro-1H-isoindol-1-one | 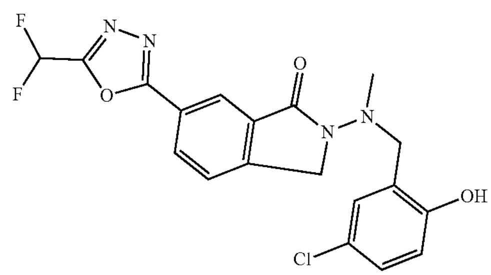 [SMILES: CN(Cc1cc(Cl)ccc1O)N1Cc2ccc(-c3nnc(C(F)F)o3)cc2C1=O] | 421.2 |
| 43c | ethyl 3-[{6-[5-(difluoromethyl)-1,3,4-oxadiazol-2-yl]-1-oxo-1,3-dihydro-2H-isoindol-2-yl}(methyl)amino]-2-methylpropanoate | 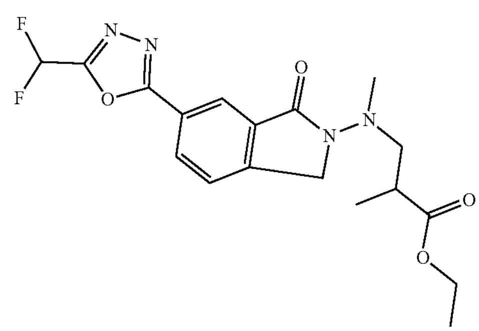 [SMILES: CCOC(=O)C(C)CN(C)N1Cc2ccc(-c3nnc(C(F)F)o3)cc2C1=O] | 395.3 |
| 44c | methyl 2-{[{6-[5-(difluoromethyl)-1,3,4-oxadiazol-2-yl]-1-oxo-1,3-dihydro-2H-isoindol-2-yl}(methyl)amino]methyl}benzoate | 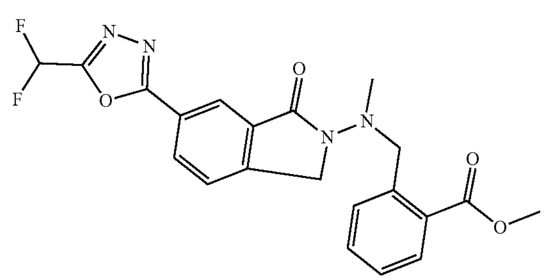 [SMILES: COC(=O)c1ccccc1CN(C)N1Cc2ccc(-c3nnc(C(F)F)o3)cc2C1=O] | 429.3 |

TABLE 3-continued

| Example | IUPAC name | Structure | MS |
| --- | --- | --- | --- |
| 45c | 6-[5-(difluoromethyl)-1,3,4-oxadiazol-2-yl]-2-{[(imidazo[1,2-a]pyridin-6-yl)methyl](methyl)amino}-2,3-dihydro-1H-isoindol-1-one | 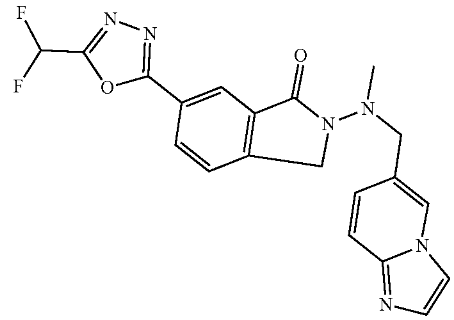 [SMILES: CN(Cc1ccc2nccn2c1)N1Cc2ccc(-c3nnc(C(F)F)o3)cc2C1=O] | 411.2 |
| 46c | ethyl N-{6-[5-(difluoromethyl)-1,3,4-oxadiazol-2-yl]-1-oxo-1,3-dihydro-2H-isoindol-2-yl}-N-methylglycinate | 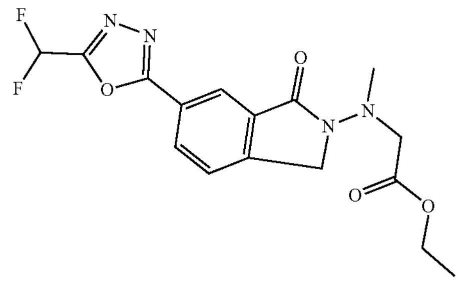 [SMILES: CCOC(=O)CN(C)N1Cc2ccc(-c3nnc(C(F)F)o3)cc2C1=O] | 367.2 |
| 47c | 6-[5-(difluoromethyl)-1,3,4-oxadiazol-2-yl]-2-{[(isoquinolin-5-yl)methyl](methyl)amino}-2,3-dihydro-1H-isoindol-1-one | 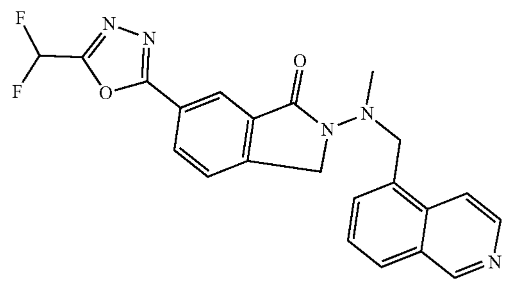 [SMILES: CN(Cc1cccc2cnccc12)N1Cc2ccc(-c3nnc(C(F)F)o3)cc2C1=O] | 422.2 |
| 48c | 2-{[2-(benzyloxy)ethyl](methyl)amino}-6-[5-(difluoromethyl)-1,3,4-oxadiazol-2-yl]-2,3-dihydro-1H-isoindol-1-one | 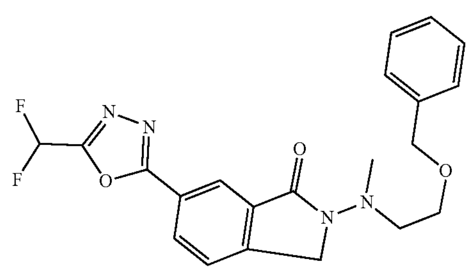 [SMILES: CN(CCOCc1ccccc1)N1Cc2ccc(-c3nnc(C(F)F)o3)cc2C1=O] | 415.3 |
| 49c | 6-[5-(difluoromethyl)-1,3,4-oxadiazol-2-yl]-2-{[(2-fluoro-5-hydroxyphenyl)methyl](methyl)amino}-2,3-dihydro-1H-isoindol-1-one | 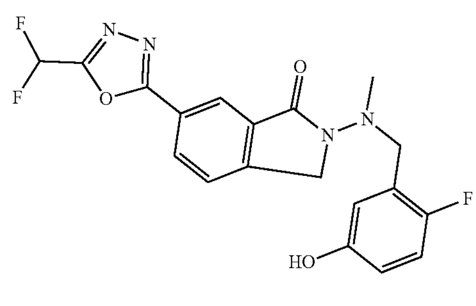 [SMILES: CN(Cc1cc(O)ccc1F)N1Cc2ccc(-c3nnc(C(F)F)o3)cc2C1=O] | 405.2 |

TABLE 3-continued

| Example | IUPAC name | Structure | MS |
|---------|------------|-----------|-----|
| 50c | ethyl 4-[{6-[5-(difluoromethyl)-1,3,4-oxadiazol-2-yl]-1-oxo-1,3-dihydro-2H-isoindol-2-yl}(methyl)amino]butanoate | 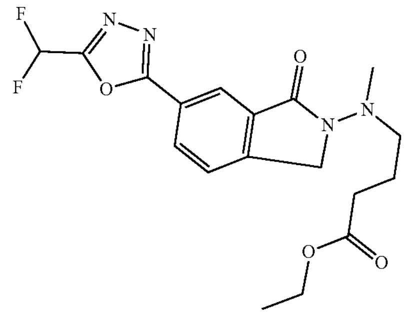 [SMILES: CCOC(=O)CCCN(C)N1Cc2ccc(-c3nnc(C(F)F)o3)cc2C1=O] | 395.2 |
| 51c | 6-[5-(difluoromethyl)-1,3,4-oxadiazol-2-yl]-2-{[(2-fluoropyridin-4-yl)methyl](methyl)amino}-2,3-dihydro-1H-isoindol-1-one | 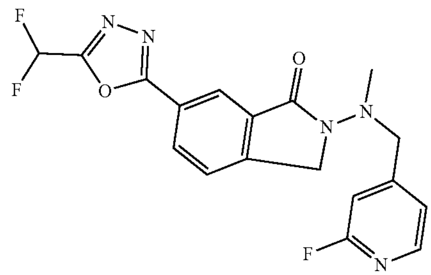 [SMILES: CN(Cc1ccnc(F)c1)N1Cc2ccc(-c3nnc(C(F)F)o3)cc2C1=O] | 390.2 |
| 52c | N-(4-{[{6-[5-(difluoromethyl)-1,3,4-oxadiazol-2-yl]-1-oxo-1,3-dihydro-2H-isoindol-2-yl}(methyl)amino]methyl}phenyl)acetamide | 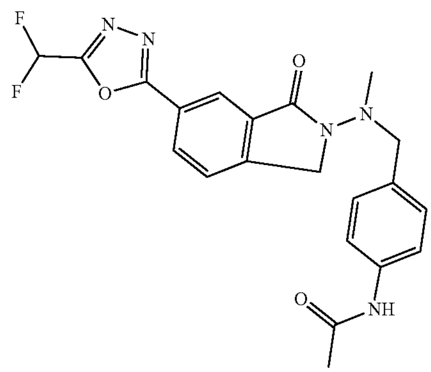 [SMILES: CC(=O)Nc1ccc(CN(C)N2Cc3ccc(-c4nnc(C(F)F)o4)cc3C2=O)cc1] | 426.2 |
| 53c | 6-[5-(difluoromethyl)-1,3,4-oxadiazol-2-yl]-2-(methyl{[3-(pyrazin-2-yl)phenyl]methyl}amino)-2,3-dihydro-1H-isoindol-1-one | 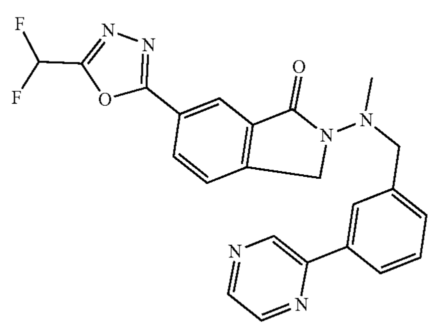 [SMILES: CN(Cc1cccc(-c2cnccn2)c1)N1Cc2ccc(-c3nnc(C(F)F)o3)cc2C1=O] | 449.2 |

TABLE 3-continued

| Example | IUPAC name | Structure | MS |
| --- | --- | --- | --- |
| 54c | 6-[5-(difluoromethyl)-1,3,4-oxadiazol-2-yl]-2-[{[4-(dimethylamino)phenyl]methyl}(methyl)amino]-2,3-dihydro-1H-isoindol-1-one | 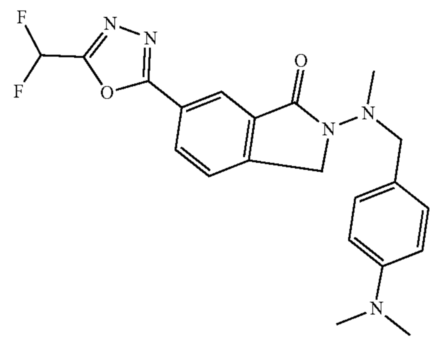 [SMILES: CN(C)c1ccc(CN(C)N2Cc3ccc(-c4nnc(C(F)F)o4)cc3C2=O)cc1] | 412.2 |
| 55c | 6-[5-(difluoromethyl)-1,3,4-oxadiazol-2-yl]-2-[{[4-(2-methoxyethoxy)phenyl]methyl}(methyl)amino]-2,3-dihydro-1H-isoindol-1-one | 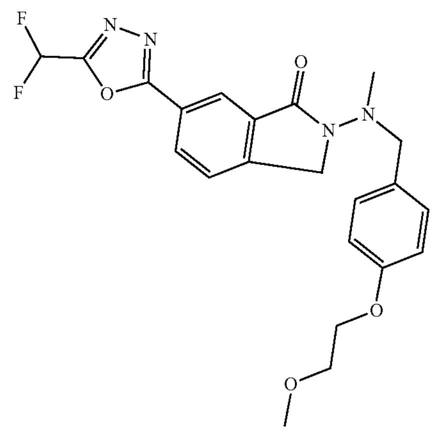 [SMILES: COCCOc1ccc(CN(C)N2Cc3ccc(-c4nnc(C(F)F)o4)cc3C2=O)cc1] | 443.2 |
| 56c | 6-[5-(difluoromethyl)-1,3,4-oxadiazol-2-yl]-2-[{[3-(difluoromethyl)phenyl]methyl}(methyl)amino]-2,3-dihydro-1H-isoindol-1-one | 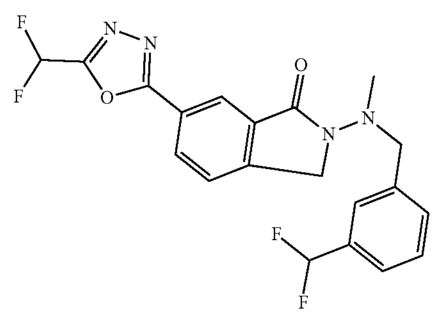 [SMILES: CN(Cc1cccc(C(F)F)c1)N1Cc2ccc(-c3nnc(C(F)F)o3)cc2C1=O] | 421.2 |
| 57c | 6-[5-(difluoromethyl)-1,3,4-oxadiazol-2-yl]-2-[{[4-(difluoromethyl)phenyl]methyl}(methyl)amino]-2,3-dihydro-1H-isoindol-1-one | 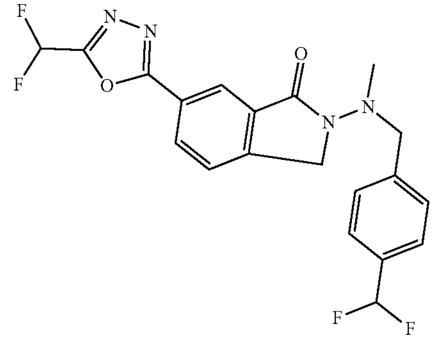 [SMILES: CN(Cc1ccc(C(F)F)cc1)N1Cc2ccc(-c3nnc(C(F)F)o3)cc2C1=O] | 421.2 |

TABLE 3-continued

| Example | IUPAC name | Structure | MS |
| --- | --- | --- | --- |
| 58c | 6-[5-(difluoromethyl)-1,3,4-oxadiazol-2-yl]-2-(methyl{[2-(morpholin-4-yl)phenyl]methyl}amino)-2,3-dihydro-1H-isoindol-1-one | 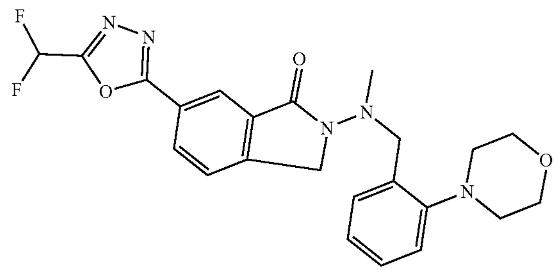 [SMILES: CN(Cc1ccccc1N1CCOCC1)N1Cc2ccc(-c3nnc(C(F)F)o3)cc2C1=O] | 456.2 |
| 59c | 6-[5-(difluoromethyl)-1,3,4-oxadiazol-2-yl]-2-[methyl({2-[(pyrazin-2-yl)oxy]phenyl}methyl)amino]-2,3-dihydro-1H-isoindol-1-one | 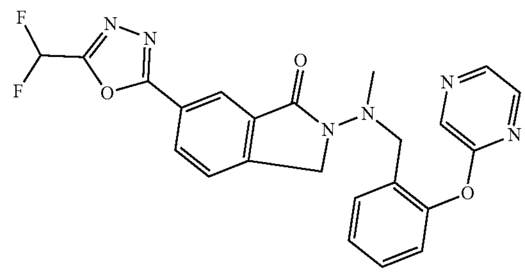 [SMILES: CN(Cc1ccccc1Oc1cnccn1)N1Cc2ccc(-c3nnc(C(F)F)o3)cc2C1=O] | 465.2 |
| 60c | 2-{[(5-chloropyridin-3-yl)methyl](methyl)amino}-6-[5-(difluoromethyl)-1,3,4-oxadiazol-2-yl]-2,3-dihydro-1H-isoindol-1-one | 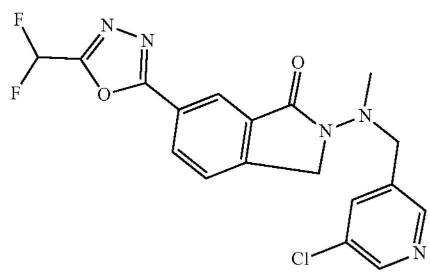 [SMILES: CN(Cc1cncc(Cl)c1)N1Cc2ccc(-c3nnc(C(F)F)o3)cc2C1=O] | 406.2 |
| 61c | 6-[5-(difluoromethyl)-1,3,4-oxadiazol-2-yl]-2-(methyl{[3-(morpholin-4-yl)phenyl]methyl}amino)-2,3-dihydro-1H-isoindol-1-one | 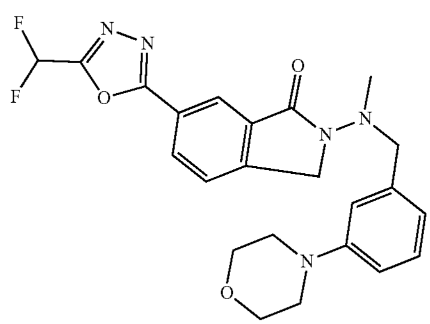 [SMILES: CN(Cc1cccc(N2CCOCC2)c1)N1Cc2ccc(-c3nnc(C(F)F)o3)cc2C1=O] | 456.3 |
| 62c | 2-{[(4,4-difluorocyclohexyl)methyl](methyl)amino}-6-[5-(difluoromethyl)-1,3,4-oxadiazol-2-yl]-2,3-dihydro-1H-isoindol-1-one | 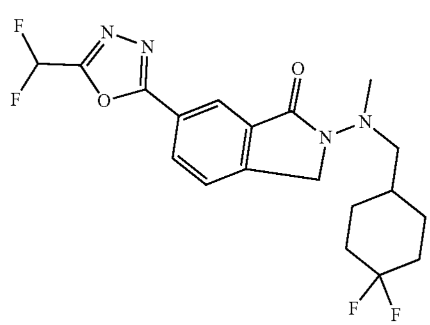 [SMILES: CN(CC1CCC(F)(F)CC1)N1Cc2ccc(-c3nnc(C(F)F)o3)cc2C1=O] | 413.2 |

TABLE 3-continued

| Example | IUPAC name | Structure | MS |
| --- | --- | --- | --- |
| 63c | 6-[5-(difluoromethyl)-1,3,4-oxadiazol-2-yl]-2-{[(3,5-dimethoxyphenyl)methyl](methyl)amino}-2,3-dihydro-1H-isoindol-1-one | 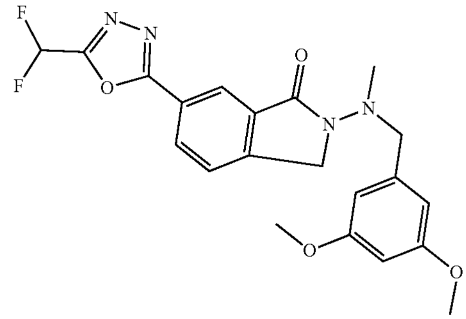 [SMILES: COc1cc(CN(C)N2Cc3ccc(-c4nnc(C(F)F)o4)cc3C2=O)cc(OC)c1] | 431.2 |
| 64c | 2-{[(3,3-difluorocyclobutyl)methyl](methyl)amino}-6-[5-(difluoromethyl)-1,3,4-oxadiazol-2-yl]-2,3-dihydro-1H-isoindol-1-one | 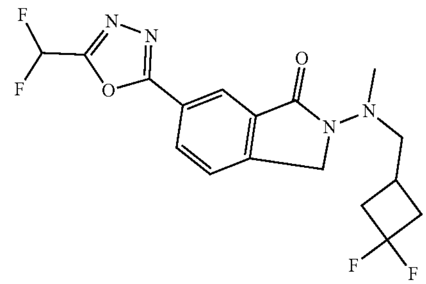 [SMILES: CN(CC1CC(F)(F)C1)N1Cc2ccc(-c3nnc(C(F)F)o3)cc2C1=O] | 385.2 |
| 65c | 6-[5-(difluoromethyl)-1,3,4-oxadiazol-2-yl]-2-[{[2-(difluoromethyl)phenyl]methyl}(methyl)amino]-2,3-dihydro-1H-isoindol-1-one | 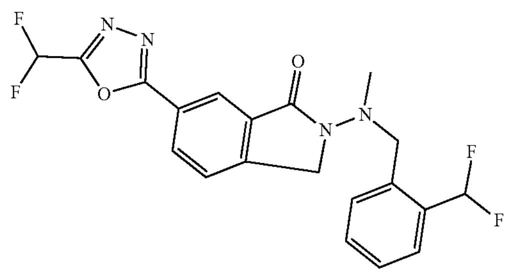 [SMILES: CN(Cc1ccccc1C(F)F)N1Cc2ccc(-c3nnc(C(F)F)o3)cc2C1=O] | 421.2 |
| 66c | 2-[cyclopropyl(methyl)amino]-6-[5-(difluoromethyl)-1,3,4-oxadiazol-2-yl]-2,3-dihydro-1H-isoindol-1-one | 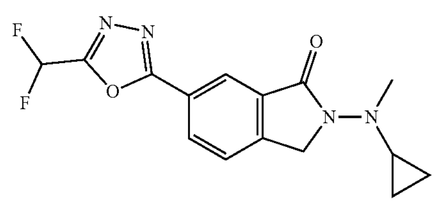 [SMILES: CN(C1CC1)N1Cc2ccc(-c3nnc(C(F)F)o3)cc2C1=O] | 321.1 |
| 68c | tert-butyl {3-[5-(difluoromethyl)-1,3,4-oxadiazol-2-yl]-5-oxo-5,7-dihydro-6H-pyrrolo[3,4-b]pyridin-6-yl}methylcarbamate | 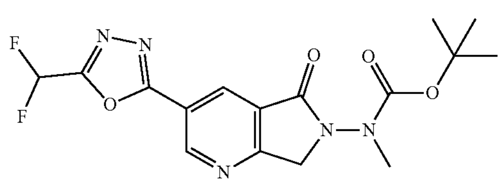 [SMILES: CN(C(=O)OC(C)(C)C)N1Cc2ncc(-c3nnc(C(F)F)o3)cc2C1=O] | 380.2 |
| 69c | 3-[5-(difluoromethyl)-1,3,4-oxadiazol-2-yl]-6-{[(4-fluorophenyl)methyl](methyl)amino}-6,7-dihydro-5H-pyrrolo[3,4-b]pyridin-5-one | 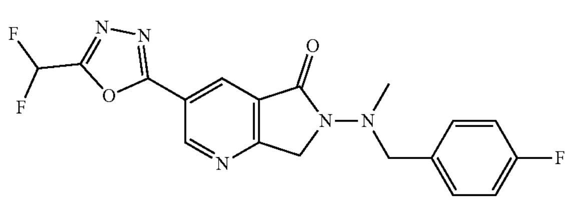 [SMILES: CN(Cc1ccc(F)cc1)N1Cc2ncc(-c3nnc(C(F)F)o3)cc2C1=O] | 390.1 |

TABLE 3-continued

| Example | IUPAC name | Structure | MS |
|---|---|---|---|
| 70c | 6-{[(5-chloropyridin-3-yl)methyl](methyl)amino}-3-[5-(difluoromethyl)-1,3,4-oxadiazol-2-yl]-6,7-dihydro-5H-pyrrolo[3,4-b]pyridin-5-one | 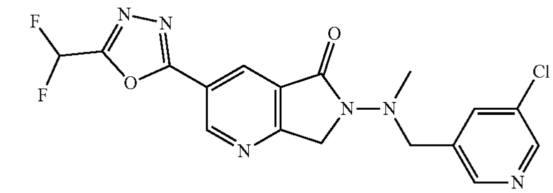 [SMILES: CN(Cc1cncc(Cl)c1)N1Cc2ncc(-c3nnc(C(F)F)o3)cc2C1=O] | 407.1 |
| 71c | 3-[5-(difluoromethyl)-1,3,4-oxadiazol-2-yl]-6-{[(4-fluorophenyl)methyl][(oxan-4-yl)methyl]amino}-6,7-dihydro-5H-pyrrolo[3,4-b]pyridin-5-one | 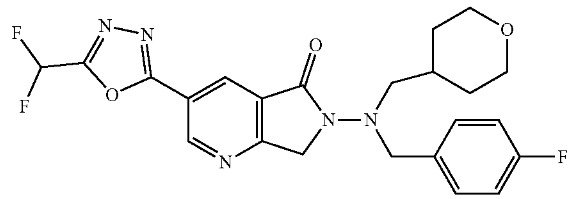 [SMILES: O=C1c2cc(-c3nnc(C(F)F)o3)cnc2CN1N(Cc1ccc(F)cc1)CC1CCOCC1] | 472.2 |

Experimental Example 1

HDAC6 Enzyme Inhibitory Assay

HDAC6 enzyme prepared by transducing full length HDAC6 gene into Sf-9 insect cells and purifying by GST affinity column were purchased from SignalChem. Using this enzyme, HDAC6 enzyme inhibitory activities of the compound of the present invention were evaluated. Enzymes were used after preserved at −70° C. HDAC6 enzyme inhibitory activity of the compound of the present invention was measured using HDAC-Glo™ I/II Assay kit (Promega) according to the following experimental method. The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC6 enzyme solution diluted with assay buffer was added thereto by each 4 μL, and the plate was incubated at room temperature for 60 min. After incubated, HDAC substrate-Developer solution prepared according to Promega protocol attached to the assay kit was added to the 384-well plate by each 2 μL, and the enzyme reaction was started. After reacting at room temperature for 20 min, luminescence level was measured using plate reader Envision (PerkinElmer). The inhibitory activity of each compound of Example was calculated as a relative activity value when luminescence level in wells without enzyme is considered as 100% inhibition. The results are shown in Table 4.

TABLE 4

| Ex. No. | HDAC6 inhibitory rate (%) (10 μM) |
|---|---|
| Compound (I-a) | |
| 1a | 100 |
| 2a | 104 |
| 3a | 99 |
| 4a | 99 |
| 5a | 98 |
| 6a | 99 |
| 7a | 100 |
| 8a | 98 |
| 9a | 79 |
| 10a | 96 |
| 11a | 94 |
| 12a | 99 |

TABLE 4-continued

| Ex. No. | HDAC6 inhibitory rate (%) (10 μM) |
|---|---|
| 13a | 92 |
| 14a | 97 |
| 15a | 92 |
| 16a | 98 |
| 17a | 96 |
| 18a | 98 |
| 19a | 99 |
| 20a | 97 |
| 21a | 93 |
| 22a | 99 |
| 23a | 96 |
| 24a | 98 |
| 25a | 98 |
| 26a | 96 |
| 27a | 95 |
| 28a | 99 |
| 29a | 99 |
| 30a | 98 |
| 31a | 98 |
| 32a | 91 |
| 33a | 86 |
| 34a | 98 |
| 35a | 98 |
| 36a | 101 |
| 37a | 99 |
| 38a | 98 |
| 39a | 98 |
| 40a | 98 |
| 41a | 21 |
| 42a | 68 |
| 43a | 98 |
| 44a | 99 |
| 45a | 100 |
| 46a | 99 |
| 47a | 99 |
| 49a | 99 |
| 53a | 100 |
| 54a | 89 |
| 55a | 97 |
| 56a | 99 |
| 57a | 97 |
| 58a | 98 |
| 59a | 99 |
| 60a | 98 |
| 61a | 98 |
| 62a | 99 |
| 63a | 97 |
| 64a | 98 |
| 65a | 100 |
| 66a | 98 |

TABLE 4-continued

| Ex. No. | HDAC6 inhibitory rate (%) (10 μM) |
|---|---|
| 67a | 99 |
| 68a | 99 |
| 70a | 98 |
| 71a | 100 |
| 72a | 100 |
| 73a | 100 |
| 74a | 99 |
| 75a | 99 |
| 76a | 100 |
| 77a | 99 |
| 78a | 103 |
| 79a | 99 |
| 80a | 104 |
| 81a | 101 |
| 82a | 99 |
| 83a | 100 |
| 84a | 100 |
| 85a | 101 |
| 86a | 100 |
| 87a | 99 |
| 88a | 100 |
| 89a | 97 |
| 90a | 98 |
| 91a | 100 |
| 92a | 100 |
| 93a | 100 |
| 94a | 99 |
| 95a | 100 |
| Compound (I-b) | |
| 1b | 100 |
| 2b | 100 |
| 3b | 101 |
| 4b | 99 |
| 5b | 71 |
| 6b | 99 |
| 7b | 100 |
| 8b | 100 |
| 9b | 96 |
| 10b | 100 |
| 11b | 99 |
| 12b | 98 |
| 13b | 99 |
| 14b | 98 |
| 15b | 88 |
| 16b | 98 |
| 17b | 100 |
| 18b | 99 |
| 19b | 100 |
| 20b | 99 |
| 21b | 99 |
| 22b | 100 |
| 23b | 58 |
| 24b | 99 |
| 25b | 100 |
| 26b | 100 |
| 27b | 56 |
| 28b | 97 |
| 29b | 99 |
| 30b | 100 |
| 31b | 100 |
| 32b | 100 |
| 33b | 100 |
| 34b | 100 |
| 35b | 100 |
| 36b | 62 |
| 37b | 100 |
| 38b | 101 |
| 39b | 76 |
| 40b | 100 |
| 41b | 99 |
| 42b | 93 |
| 43b | 100 |
| 44b | 100 |
| 45b | 100 |
| 46b | 100 |
| 47b | 101 |
| 48b | 101 |
| 49b | 42 |
| 50b | 101 |
| 51b | 99 |
| 52b | 100 |
| 53b | 98 |
| 54b | 75 |
| 55b | 100 |
| 56b | 100 |
| Compound (I-c) | |
| 1c | 99 |
| 2c | 99 |
| 3c | 99 |
| 4c | 100 |
| 5c | 99 |
| 6c | 99 |
| 7c | 100 |
| 8c | 95 |
| 9c | 97 |
| 10c | 97 |
| 11c | 99 |
| 12c | 98 |
| 13c | 99 |
| 14c | 100 |
| 15c | 99 |
| 16c | 100 |
| 17c | 98 |
| 18c | 99 |
| 19c | 98 |
| 21c | 99 |
| 22c | 100 |
| 23c | 101 |
| 24c | 100 |
| 25c | 99 |
| 26c | 99 |
| 27c | 99 |
| 28c | 99 |
| 29c | 95 |
| 30c | 92 |
| 31c | 90 |
| 32c | 95 |
| 33c | 99 |
| 34c | 92 |
| 35c | 93 |
| 36c | 98 |
| 37c | 99 |
| 38c | 97 |
| 39c | 88 |
| 40c | 101 |
| 41c | 99 |
| 42c | 98 |
| 43c | 94 |
| 44c | 102 |
| 45c | 99 |
| 46c | 99 |
| 47c | 100 |
| 48c | 99 |
| 49c | 100 |
| 50c | 98 |
| 51c | 100 |
| 52c | 100 |
| 53c | 101 |
| 54c | 97 |
| 55c | 101 |
| 56c | 99 |
| 57c | 99 |
| 58c | 100 |
| 59c | 101 |
| 60c | 101 |
| 61c | 99 |
| 62c | 100 |
| 63c | 101 |
| 64c | 99 |
| 65c | 101 |
| 66c | 94 |
| 68c | 99 |

TABLE 4-continued

| Ex. No. | HDAC6 inhibitory rate (%) (10 μM) |
|---|---|
| 69c | 100 |
| 70c | 100 |
| 71c | 100 |

As is clear from Table 4, the compound of the present invention has an excellent HDAC6 inhibitory activity.

Formulation Example 1a (Production of Capsule)

| 1) compound of Example 1a | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin.

Formulation Example 2a (Production of Tablet)

| 1) compound of Example 1a | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1a per tablet are obtained.

Formulation Example 1b (Production of Capsule)

| 1) compound of Example 1b | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin.

Formulation Example 2b (Production of Tablet)

| 1) compound of Example 1b | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1b per tablet are obtained.

Formulation Example 1c (Production of Capsule)

| 1) compound of Example 1c | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin.

Formulation Example 2c (Production of Tablet)

| 1) compound of Example 1c | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1c per tablet are obtained.

INDUSTRIAL APPLICABILITY

The compound of the present invention has a HDAC inhibitory activity, and may be useful for the treatment of central nervous system diseases including neurodegenerative diseases (Alzheimer's disease, progressive supranuclear palsy, etc.) and the like.

This application is based on patent application No. 2019-014893 filed on Jan. 30, 2019 in Japan, the contents of which are encompassed in full herein.

The invention claimed is:

1. A compound represented by the formula (I):

(I)

wherein R is
(a) a group represented by the formula:

wherein
$X^a$ is $CR^{2a}$ wherein $R^{2a}$ is a hydrogen atom or a halogen atom, or N, $Y^a$ is $CR^{3a}$ wherein $R^{3a}$ is a hydrogen atom or a halogen atom, or N, Ring $A^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms, Ring $B^a$ is an optionally further substituted ring, $L_a$ is a bond, or a spacer having 1 to 3 atoms in the main chain, and $R^{1a}$ is an optionally substituted $C_{1-6}$ alkyl group or an optionally substituted cyclic group, (b) a group represented by the formula:

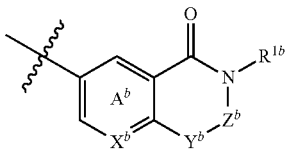

wherein $X^b$ is $CR^{2b}$ wherein $R^{2b}$ is a hydrogen atom or a halogen atom, or N, Ring $A^b$ is (i) a benzene ring optionally further substituted by 1 or 2 halogen atoms, or (ii) a pyridine ring optionally further substituted by 1 or 2 halogen atoms, $Y^b$ is an oxygen atom or an optionally substituted methylene, $Z^b$ is $CR^{3b}R^{4b}$ wherein $R^{3b}$ and $R^{4b}$ are each independently a hydrogen atom, an optionally substituted $C_{1-6}$ alkyl group or an optionally substituted cyclic group, or $NR^{5b}$ wherein $R^{5b}$ is an optionally substituted $C_{1-6}$ alkyl group or an optionally substituted cyclic group, and $R^{1b}$ is a hydrogen atom, an optionally substituted $C_{1-6}$ alkyl group or an optionally substituted cyclic group, or (c) a group represented by the formula:

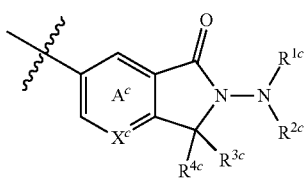

wherein $X^c$ is $CR^{5c}$ wherein $R^{5c}$ is a hydrogen atom or a halogen atom, or N, Ring $A^c$ is (i) a benzene ring optionally further substituted by 1 or 2 halogen atoms, or (ii) a pyridine ring optionally further substituted by 1 or 2 halogen atoms, $R^{1c}$ and $R^{2c}$ are each independently a hydrogen atom or a substituent, and $R^{3c}$ and $R^{4c}$ are each independently a hydrogen atom, an optionally substituted $C_{1-6}$ alkyl group or an optionally substituted $C_{1-6}$ alkoxy group, or a salt thereof.

2. The compound or salt according to claim 1, which is represented by the formula (I-a):

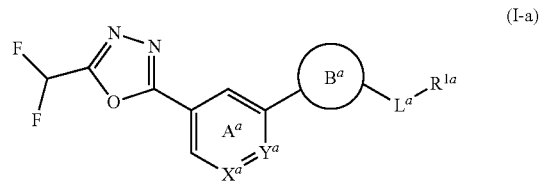

wherein $X^a$ is $CR^{2a}$ wherein $R^{2a}$ is a hydrogen atom or a halogen atom, or N, $Y^a$ is $CR^{3a}$ wherein $R^{3a}$ is a hydrogen atom or a halogen atom, or N, Ring $A^a$ is (i) a benzene ring optionally further substituted by 1 or 2 halogen atoms, (ii) a pyridine ring optionally further substituted by 1 or 2 halogen atoms, or (iii) a pyridazine ring optionally further substituted by 1 or 2 halogen atoms, Ring $B^a$ is an optionally further substituted ring, $L_a$ is a bond, or a spacer having 1 to 3 atoms in the main chain, and $R^{1a}$ is an optionally substituted $C_{1-6}$ alkyl group or an optionally substituted cyclic group.

3. The compound or salt according to claim 2, wherein $X^a$ is CH, CF or N;

$Y^a$ is CH or N;

Ring $A^a$ is a benzene ring optionally substituted by one fluorine atom, or a pyridine ring, which is represented by formula:

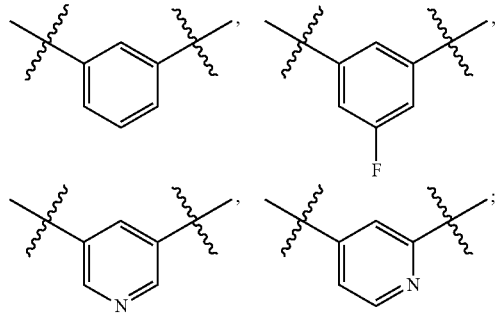

Ring $B^a$ is (1) a 5- or 6-membered monocyclic aromatic heterocycle optionally substituted by 1 to 3 substituents selected from a halogen atom and a cyano group, (2) a 5- or 6-membered non-aromatic heterocycle optionally substituted by 1 to 3 substituents selected from a $C_{1-6}$ alkyl group and an oxo group, or (3) a 9- to 14-membered fused bicyclic non-aromatic heterocycle;

$L_a$ is (1) a bond, (2) —$CH_2$—, (3) —$CH(CH_3)$—, (4) —O—, (5) —$OCH_2$—, (6) —$CH_2C(O)$—, (7) —$OCH_2CH_2$—, (8) —$CH_2C(O)NH$— or (9) —$CH_2CH_2O$—; and $R^{1a}$ is
(1) a $C_{1-6}$ alkyl group optionally substituted by 1 to 3 $C_{1-6}$ alkoxy groups,
(2) a $C_{3-6}$ cycloalkyl group optionally substituted by 1 to 3 halogen atoms,
(3) a $C_{6-10}$ aryl group optionally substituted by 1 to 3 substituents selected from
  (i) a halogen atom,
  (ii) a cyano group,
  (iii) an optionally halogenated $C_{1-6}$ alkyl group,
  (iv) a $C_{1-6}$ alkoxy group, and
  (v) an N-mono-$C_{1-6}$ alkyl-carbamoyl group,
(4) a 5- or 6-membered aromatic heterocyclic group optionally substituted by 1 to 3 substituents selected from
  (i) a halogen atom,
  (ii) a cyano group,
  (iii) a $C_{1-6}$ alkyl group, and
  (iv) a $C_{1-6}$ alkoxy group, or
(5) a 4- to 6-membered non-aromatic heterocyclic group optionally substituted by 1 to 3 substituents selected from
  (i) a $C_{1-6}$ alkyl group,
  (ii) a $C_{1-6}$ alkyl-carbonyl group,
  (iii) a $C_{1-6}$ alkoxy-carbonyl group, and
  (iv) an oxo group.

4. The compound or salt of claim 2 which is
5-[(2-{4-[5-(Difluoromethyl)-1,3,4-oxadiazol-2-yl] pyridin-2-yl}-1H-imidazol-1-yl)methyl]-2-fluorobenzonitrile or a salt thereof,
2-{4-[5-(difluoromethyl)-1,3,4-oxadiazol-2-yl] pyridin-2-yl}-1-[(3-fluorophenyl)methyl]-1H-imidazole-5-carbonitrile or a salt thereof, or
4-[5-(difluoromethyl)-1,3,4-oxadiazol-2-yl]-2-{1-[(3-fluorophenyl)methyl]-1H-1,2,4-triazol-5-yl}pyridine or a salt thereof.

5. The compound or salt according to claim 1, which is represented by the formula (I-b):

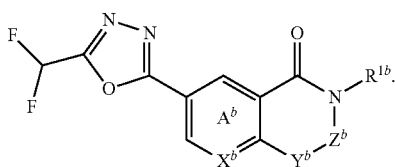

(I-b)

wherein
$X^b$ is $CR^{2b}$ wherein $R^{2b}$ is a hydrogen atom or a halogen atom, or N,
Ring $A^b$ is (i) a benzene ring optionally further substituted by 1 or 2 halogen atoms, or (ii) a pyridine ring optionally further substituted by 1 or 2 halogen atoms,
$Y^b$ is an oxygen atom or an optionally substituted methylene,
$Z^b$ is $CR^{3b}R^{4b}$ wherein $R^{3b}$ and $R^{4b}$ are each independently a hydrogen atom, an optionally substituted $C_{1-6}$ alkyl group or an optionally substituted cyclic group, or $NR^{5b}$ wherein $R^{5b}$ is an optionally substituted $C_{1-6}$ alkyl group or an optionally substituted cyclic group, and
$R^{1b}$ is a hydrogen atom, an optionally substituted $C_{1-6}$ alkyl group or an optionally substituted cyclic group.

6. The compound or salt according to claim 5, wherein
$X^b$ is CH or N;
Ring $A^b$ is (i) a benzene ring, or (ii) a pyridine ring;
$Y^b$ is an oxygen atom or methylene;
(1) a group represented by $CR^{3b'}R^{4b'}$ wherein
  $R^{3b'}$ is
    (a) a hydrogen atom, or
    (b) a $C_{1-6}$ alkyl group optionally substituted by 1 to 3 $C_{1-6}$ alkoxy groups; and
  $R^{4b'}$ is
    (a) a hydrogen atom,
    (b) a $C_{3-6}$ cycloalkyl group,
    (c) a $C_{6-10}$ aryl group optionally substituted by 1 to 3 substituents selected from
      (i) a halogen atom,
      (ii) a cyano group,
      (iii) an optionally halogenated $C_{1-6}$ alkyl group, and
      (iv) an optionally halogenated $C_{1-6}$ alkoxy group, or
    (d) a 5- or 6-membered aromatic heterocyclic group, or
(2) a group represented by $NR^{5b'}$ wherein
  $R^{5b'}$ is
    (a) an optionally halogenated $C_{1-6}$ alkyl group,
    (b) a $C_{3-6}$ cycloalkyl group optionally substituted by 1 to 3 halogen atoms,
    (c) a $C_{6-10}$ aryl group optionally substituted by 1 to 3 halogen atoms, or
    (d) a 5- or 6-membered non-aromatic heterocyclic group; and
$R^{1b}$ is
(1) a hydrogen atom, or
(2) a $C_{1-6}$ alkyl group optionally substituted by 1 to 3 substituents selected from
  (i) a halogen atom,
  (ii) a $C_{3-6}$ cycloalkyl group,
  (iii) a $C_{6-10}$ aryl group, and
  (iv) a $C_{1-6}$ alkoxy group (e.g., methoxy).

7. The compound or salt of claim 5 which is
3-[5-(Difluoromethyl)-1,3,4-oxadiazol-2-yl]-7-(4-fluorophenyl)-6,7-dimethyl-7,8-dihydro-1,6-naphthyridin-5 (6H)-one or a salt thereof,
7-[5-(difluoromethyl)-1,3,4-oxadiazol-2-yl]-3-(4-fluorophenyl)-3,4-dihydrophthalazin-1 (2H)-one or a salt thereof, or
7-[5-(difluoromethyl)-1,3,4-oxadiazol-2-yl]-2-ethyl-3-(4-fluorophenyl)-3,4-dihydrophthalazin-1 (2H)-one or a salt thereof.

8. The compound or salt according to claim 1, which is represented by the formula (I-c):

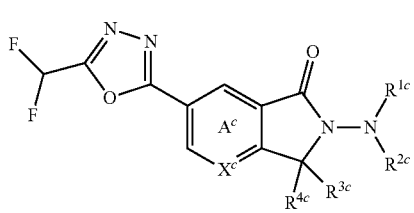

(I-c)

wherein
$X^c$ is $CR^{5c}$ wherein $R^{5c}$ is a hydrogen atom or a halogen atom, or N,
Ring $A^c$ is (i) a benzene ring optionally further substituted by 1 or 2 halogen atoms, or (ii) a pyridine ring optionally further substituted by 1 or 2 halogen atoms, $R^{1c}$ and $R^{2c}$ are each independently a hydrogen atom or a substituent, and $R^{3c}$ and $R^{4c}$ are each independently a hydrogen atom, an optionally substituted $C_{1-6}$ alkyl group or an optionally substituted $C_{1-6}$ alkoxy group.

9. The compound or salt according to claim 8, wherein $X^c$ is CH, or N;

Ring $A^c$ is (i) a benzene ring, or (ii) a pyridine ring;

$R^{1c}$ is (1) a hydrogen atom, (2) a $C_{1-6}$ alkyl group optionally substituted by 1 to 3 substituents selected from
 (i) a $C_{6-10}$ aryl group optionally substituted by 1 to 3 halogen atoms,
 (ii) a 5- or 6-membered aromatic heterocyclic group optionally substituted by 1 to 3 $C_{3-6}$ cycloalkyl groups, and
 (iii) a 5- or 6-membered non-aromatic heterocyclic group, (3) a $C_{1-6}$ alkyl-carbonyl group optionally substituted by 1 to 3 halogen atoms, (4) a $C_{1-6}$ alkoxy-carbonyl group optionally substituted by 1 to 3 substituents selected from
 (i) a halogen atom,
 (ii) a $C_{1-6}$ alkoxy group, and
 (iii) a 5- or 6-membered aromatic heterocyclic group, (5) a $C_{3-6}$ cycloalkoxy-carbonyl group optionally substituted by 1 to 3 $C_{1-6}$ alkoxy groups, (6) a 5- or 6-membered non-aromatic heterocyclyloxy-carbonyl group, or (7) a $C_{1-6}$ alkylsulfonyl group;

$R^{2c}$ is (1) a $C_{1-6}$ alkyl group optionally substituted by 1 to 3 substituents selected from
 (i) a halogen atom,
 (ii) a $C_{3-6}$ cycloalkyl group optionally substituted by 1 to 3 halogen atoms,
 (iii) a $C_{6-10}$ aryl group optionally substituted by 1 to 3 substituents selected from
  (a) a halogen atom,
  (b) a hydroxy group,
  (c) an optionally halogenated $C_{1-6}$ alkyl group,
  (d) a $C_{1-6}$ alkoxy group optionally substituted by 1 to 3 $C_{1-6}$ alkoxy groups,
  (e) a $C_{1-6}$ alkoxy-carbonyl group,
  (f) a di-$C_{1-6}$ alkylamino group,
  (g) a $C_{1-6}$ alkyl-carbonylamino group,
  (h) a 5- or 6-membered aromatic heterocyclic group,
  (i) a 5- or 6-membered non-aromatic heterocyclic group, and
  (j) a 5- or 6-membered aromatic heterocyclyloxy group,
 (iv) a $C_{7-16}$ aralkyloxy group,
 (v) a $C_{1-6}$ alkoxy-carbonyl group,
 (vi) a 5- or 6-membered aromatic heterocyclic group optionally substituted by 1 to 3 substituents selected from
  (a) a halogen atom, and
  (b) a $C_{3-6}$ cycloalkyl group,
 (vii) a 5- or 6-membered non-aromatic heterocyclic group, and
 (viii) a 8- to 14-membered fused polycyclic aromatic heterocyclic group, (2) a $C_{3-6}$ cycloalkyl group optionally substituted by 1 to 3 halogen atoms, (3) a $C_{6-10}$ aryl group optionally substituted by 1 to 5 halogen atoms, (4) a 5- or 6-membered aromatic heterocyclic group optionally substituted by 1 to 3 halogen atoms, (5) a 5- or 6-membered non-aromatic heterocyclic group, or (6) a $C_{1-6}$ alkoxy-carbonyl group; and $R^{3c}$ and $R^{4c}$ are both hydrogen atoms.

10. The compound or salt of claim 8 which is

6-[5-(Difluoromethyl)-1,3,4-oxadiazol-2-yl]-2-{[(4-fluorophenyl)methyl] [(oxan-4-yl)methyl] amino}-2,3-dihydro-1H-isoindol-1-one or a salt thereof, 2-{[(5-chloropyridin-3-yl)methyl] (methyl)amino}-6-[5-(difluoromethyl)-1,3,4-oxadiazol-2-yl]-2,3-dihydro-1H-isoindol-1-one or a salt thereof, or 2-{[(3,3-difluorocyclobutyl)methyl] (methyl)amino}-6-[5-(difluoromethyl)-1,3,4-oxadiazol-2-yl]-2,3-dihydro-1H-isoindol-1-one or a salt thereof.

11. A medicament comprising the compound or salt according to claim 1.

12. The medicament according to claim 11, which is a histone deacetylase 6 inhibitor.

13. The medicament according to claim 11, which is an agent for the treatment of Alzheimer's disease or progressive supranuclear palsy.

14. The compound or salt according to claim 1 for use in the treatment of Alzheimer's disease or progressive supranuclear palsy.

15. A method for inhibiting histone deacetylase 6 in a mammal, which comprises administering an effective amount of the compound or salt according to claim 1 to the mammal.

16. A method for treating Alzheimer's disease or progressive supranuclear palsy in a mammal, which comprises administering an effective amount of the compound or salt according to claim 1 to the mammal.

* * * * *